US012584154B2

(12) United States Patent
Heinisch et al.

(10) Patent No.: US 12,584,154 B2
(45) Date of Patent: Mar. 24, 2026

(54) TEMPLATE-FREE ENZYMATIC SYNTHESIS OF POLYNUCLEOTIDES USING POLY(A) AND POLY(U) POLYMERASES

(71) Applicant: DNA SCRIPT, Le Kremlin-Bicêtre (FR)

(72) Inventors: Tillmann Heinisch, Le Kremlin-Bicêtre (FR); Elise Champion, Paris (FR); Elodie Sune, Le Kremlin-Bicêtre (FR); Mikhael Soskine, Franconville (FR)

(73) Assignee: DNA Script, Le Kremlin-Bicêtre (FR)

( * ) Notice: Subject to any disclaimer, the term of this patent is extended or adjusted under 35 U.S.C. 154(b) by 1090 days.

(21) Appl. No.: 17/629,316

(22) PCT Filed: Jul. 28, 2020

(86) PCT No.: PCT/EP2020/071314
§ 371 (c)(1),
(2) Date: Jan. 21, 2022

(87) PCT Pub. No.: WO2021/018919
PCT Pub. Date: Feb. 4, 2021

(65) Prior Publication Data
US 2022/0403434 A1 Dec. 22, 2022

(30) Foreign Application Priority Data

Jul. 30, 2019 (EP) .................................... 19189192
Apr. 20, 2020 (EP) .................................... 20170323

(51) Int. Cl.
*C12N 9/12* (2006.01)
*C12P 19/34* (2006.01)

(52) U.S. Cl.
CPC ............ *C12P 19/34* (2013.01); *C12N 9/1264* (2013.01); *C12Y 207/07031* (2013.01)

(58) Field of Classification Search
None
See application file for complete search history.

(56) References Cited

U.S. PATENT DOCUMENTS

| | | | |
|---|---|---|---|
| 5,367,066 A | 11/1994 | Urdea et al. | |
| 5,700,642 A | 12/1997 | Monforte et al. | |
| 5,739,386 A | 4/1998 | Holmes | |
| 5,763,594 A | 6/1998 | Hiatt et al. | |
| 5,808,045 A | 9/1998 | Hiatt et al. | |
| 5,830,655 A | 11/1998 | Monforte et al. | |
| 7,057,026 B2 | 6/2006 | Barnes et al. | |
| 2003/0186226 A1 | 10/2003 | Brennan et al. | |
| 2004/0106728 A1 | 6/2004 | McGall et al. | |
| 2005/0037991 A1 | 2/2005 | Bodepudi et al. | |
| 2016/0046974 A1 | 2/2016 | Efeavitch et al. | |
| 2019/0211315 A1 | 7/2019 | Champion et al. | |

FOREIGN PATENT DOCUMENTS

| | | |
|---|---|---|
| WO | WO1991/006678 | 5/1991 |
| WO | 97/09429 A2 | 3/1997 |
| WO | WO2004/005667 | 1/2004 |
| WO | WO2015/159023 | 10/2015 |
| WO | WO2017/216472 | 12/2017 |
| WO | WO2020/077227 | 4/2020 |

OTHER PUBLICATIONS

Singh et al. (Curr. Protein Pept. Sci. 18:1-11, 2017).*
Zhang et al. (Structure 26: 1474-1485, 2018).*
Huttner and Dainat, (Uniprot Accession No. A0A3S4AP69, Jul. 3, 2019).*
Altschul et al., "Gapped BLAST and PSI-BLAST: a new generation of protein database search programs" Nucleic Acids Research, 25(17): 3389-3402 (1997).
Altschul et al., "Protein Database Searches Using Compositionally Adjusted" FEBS J., 272: 5101-5109 (2005).
Bentolila et al., "The Two Isoforms of Mouse Terminal Deoxynucleotidyl Transferase Differ in both the Ability to add N Regions and Subcellular Localization" EMBO J., 14: 4221-4229 (1995).
Boule et al., "High-level expression of murine terminal deoxynucleotidyl transferase in *Escherichia coli* grown at low temperature and overexpressing argU tRNA" Mol. Biotechnology, 10: 199-208 (1998).
Canard et al., "DNA polymerase fluorescent substrates with reversible 3'-tags" Gene, 148: 1-6 (1994).
Corpet et la., "Multiple Sequence Alignment with Hierarchical Clustering" Nucleic Acids Research 16(22): 10881-10890 (1988).
Cuomo et al., "Draft Genome Sequence of the Cellulolytic Fungus Chaetomium globosum" Genome Announc. 3(1): e00021-15 (2015).
Jensen et al., "Template-Independent Enzymatic 11 Oligonucleotide Synthesis (TiEOS): Its History, Prospects, and Challenges" Biochemistry, 57: 1821-1832 (2018).
Kodumal et al., "Total synthesis of long DNA sequences: Synthesis of a contiguous 32-kb polyketide synthase gene cluster" Proc. Natl. Acad. Sci., 101: 15573-15578 (2004).
Meng et al., "Design and Synthesis of a Photocleavable Fluorescent Nucleotide 3'-O-Allyl-dGTP-PC-Bodipy-FL-510 as a Reversible Terminator for DNA Sequencing by Synthesis" J. Org. Chem., 14: 3248-3252 (2006).
Metzker et al., "Termination of DNA synthesis by novel 3'-modified-deoxyribonucleoside 5'-triphosphates" Nucleic Acids Research, 22: 4259-4267 (1994).
Needleman et al., "A General Metho Applicable to the Search for Similarities in the Amino Acid Sequence of Two Proteins" J. Mol. Biol., 48: 443-453 (1970).
Smith et al., "Identification of Common Molecular Subsequences" J. Mol. Biol., 147: 195-197 (1981).
Stemmer et al., "Single-step assembly of a gene and entire plasmid from large Nos. of oligodeoxyribonucleotides" Gene, 164: 49-53 (1995).

(Continued)

*Primary Examiner* — Richard G Hutson
(74) *Attorney, Agent, or Firm* — MORRISON & FOERSTER LLP

(57) ABSTRACT

The present invention is directed to methods and compositions for template-free enzymatic synthesis of a polyribonucleotide of a predetermined sequence from 3'-O-reversibly blocked nucleoside triphosphates using poly(A) and poly(U) polymerases.

7 Claims, 5 Drawing Sheets

Specification includes a Sequence Listing.

(56)                        References Cited

OTHER PUBLICATIONS

Zavgorodny et al., "1-Alkylthioalkylation of Nucleoside Hydroxyl
Functions and Its Synthetic Applications: A New Versatile Method
in Nucleoside Chemistry", Tetrahedron Letters, 32(51): 7593-7596
(1991).

* cited by examiner

| additions | 0 | 1 | 2 | 3 | 1 (A) | 2 (AU) | 1 (U) | 2 (UA) |
|---|---|---|---|---|---|---|---|---|
| "+5" | | | | 8 | | | | |
| "+4" | | | | 20 | | | | |
| "+3" | | | 15 | 57 | | 10 | | |
| "+2" | | | 76 | 9 | | 58 | 6 | 54 |
| "+1" | 13 | 98 | 9 | 6 | 97 | 30 | 90 | 43 |
| "0" | 87 | 2 | | | 3 | 2 | 4 | 4 |

| Temperature | 37 | | | | | | | | | 65 | 37 |
|---|---|---|---|---|---|---|---|---|---|---|---|
| Time (min) | 15 | 15 | 15 | 15 | 60 | 60 | 60 | 60 | 60 | | |
| pH | 7 | 8 | 9 | 7 | 7 | 8 | 9 | 7 | 8 | | water |
| [TCEP] mM | 100 | 100 | 100 | 200 | 100 | 100 | 100 | 200 | 100 | | |
| Tris, NaCl | | yes | | | | yes | | | yes | | |
| "+2" | 88.5 | 91.3 | 90.4 | 91.5 | 91.1 | 92.5 | 89.1 | 91.4 | 100 | | |
| "+1" | 11.5 | 8.7 | 9.6 | 8.5 | 8.9 | 7.5 | 10.9 | 8.6 | | | 9 |
| "0" | | | | | | | | | | | 91 |

| M310X | - | F | F | M | M | V* | M* | V | Q* | M | M | M | Q | A | M | Y | Thermo (M) |
|---|---|---|---|---|---|---|---|---|---|---|---|---|---|---|---|---|---|
| +1% | 0 | 98 | 83 | 43 | 97 | 20 | 58 | 32 | 0 | 54 | 91 | 35 | 93 | 13 | 84 | 98 | 99 |

*mutants contain one additional mutation besides M310X

G     U     A     C     no
                        ext

TEMPLATE-FREE ENZYMATIC SYNTHESIS OF POLYNUCLEOTIDES USING POLY(A) AND POLY(U) POLYMERASES

CROSS-REFERENCE TO RELATED APPLICATIONS

This application is a 371 of International Application Serial No. PCT/EP2020/071314, filed on Jul. 28, 2020, which application claims priority to EP20170323.8, filed on Apr. 20, 2020, and EP19189192.8, filed on Jul. 30, 2019, the disclosures of which are incorporated herein by reference in their entirety.

INCORPORATION BY REFERENCE OF SEQUENCE LISTING PROVIDED AS A TEXT FILE

A Sequence Listing is provided herewith in a text file "DNAS-010_SEQ_LIST(RevJul2022)_ST25" created on Jul. 11, 2022 and having a size of 200,178 bytes. The contents of the text file are incorporated herein by reference in their entirety.

BACKGROUND

Interest has arisen in supplementing or replacing chemically-based synthesis methods by enzymatically-based methods using template-free polymerases, such as, terminal deoxynucleotidyl transferase (TdT), because of the proven efficiency of such enzymes and the benefit of mild non-toxic reaction conditions, e.g. Ybert et al, International patent publication WO2015/159023; Hiatt et al, U.S. Pat. No. 5,763,594; Jensen et al, Biochemistry, 57: 1821-1832 (2018); and the like. Most approaches in enzyme-based synthesis are limited to DNA synthesis and require the use of reversibly blocked nucleoside triphosphates in order to obtain a desired sequence in the polynucleotide product. Unfortunately, natural TdTs incorporate such modified nucleoside triphosphates with reduced efficiency as compared to unmodified nucleoside triphosphates. Thus, a great deal of work has been directed to developing new TdT variants with better incorporation efficiencies for modified nucleoside triphosphates to synthesize DNA, e.g. Champion et al, U.S. patent publication US2019/0211315; Ybert et al, International patent publication WO2017/216472, and the like.

In view of the above, the field of template-free enzymatically-based polynucleotide synthesis would be advanced if new template-free polymerases were available for synthesize DNA and RNA with improved incorporation of reversibly blocked nucleoside triphosphates.

SUMMARY OF THE INVENTION

The present invention is directed to methods, kits and compositions for template-free enzymatic synthesis of polynucleotides using poly(A) and poly(U) polymerases and variants thereof. In some embodiments, methods employing poly(A) and poly(U) polymerases are used to synthesize RNA products of a predetermined sequence. In other embodiments, methods employing poly(A) and poly(U) polymerases are used to synthesize DNA products of a predetermined sequence.

In some embodiments, the invention is directed to methods of synthesizing a polynucleotide having a predetermined sequence comprising the steps of: a) providing an initiator having a 3'-terminal nucleotide having a free 3'-hydroxyl; and b) repeating, until the polynucleotide is formed, cycles of (i) contacting under elongation conditions the initiator or elongated fragments having free 3'-hydroxyls with a 3'-O-blocked-nucleoside triphosphate and a template-free polymerase so that the initiator or elongated fragments are elongated by incorporation of a 3'-O-blocked-nucleoside triphosphate to form 3'-O-blocked-elongated fragments, and (ii) deblocking the elongated fragments to form elongated fragments having free 3'-hydroxyls; wherein the template-free polymerase is a poly(A) polymerase (PAP) or a poly(U) polymerase. In further embodiments, the initiator may be attached to a support by a 5' end. In further embodiments, the support may be a solid support.

In some embodiments, the above method may include a step of cleaving the polynucleotide from the initiator.

In some embodiments, the polynucleotide is a poly-2'-deoxyribonucleotide and the 3'-0-blocked-nucleoside triphosphate is a 3'-O-blocked-2'-deoxyribonucleoside triphosphate. In further embodiments, the 3'-O-blocked-2'-deoxyribonucleotide triphosphate is a 3'-O-azidomethyl-2'-deoxyribonucleoside triphosphate or a 3'-O-amino-2'-deoxyribonucleoside triphosphate. In further embodiments, the polynucleotide is a polyribonucleotide and said 3'-O-blocked-nucleoside triphosphate is a 3'-O-blocked-ribonucleoside triphosphate. In some embodiments, the 3'-O-blocked-ribonucleoside triphosphate is a 3'-O-azidomethyl-ribonucleoside triphosphate. In further embodiments, the 3'-azidomethyl-O-ribonucleoside triphosphate is selected from the group consisting of 3'-azidomethyl-O-adenosine triphosphate, 3'-azidomethyl-O-guanosine triphosphate, and 3'-azidomethyl-O-cytidine triphosphate, 3'-azidomethyl-O-uridine triphosphate.

In some embodiments, the poly(A) polymerase employed in the method of the invention is a poly(A) polymerase variant comprising an amino acid sequence that is at least 90 percent identical to an amino acid sequence selected from SEQ ID NO: 1, 2, 3, 8, 9, 10, 11, 12, 13, 14, 15, 16, 17, 18, 19, 20, 21, 22, 23, 24, 25, 26 or 27 with a substitution of methionine at position 310 with respect to SEQ ID NO: 1, at position 318 with respect to SEQ ID NO: 2, at position 318 with respect to SEQ ID NO: 3, at position 316 with respect to SEQ ID NO: 8, at position 309 with respect to SEQ ID NO: 9, at position 316 with respect to SEQ ID NO: 10, at position 272 with respect to SEQ ID NO: 11, at position 316 with respect to SEQ ID NO: 12, at position 307 with respect to SEQ ID NO: 13, at position 313 with respect to SEQ ID NO: 14, at position 312 with respect to SEQ ID NO: 15, at position 317 with respect to SEQ ID NO: 16, at position 316 with respect to SEQ ID NO: 17, at position 316 with respect to SEQ ID NO: 18, at position 312 with respect to SEQ ID NO: 19, at position 310 with respect to SEQ ID NO: 20, at position 309 with respect to SEQ ID NO: 21, at position 317 with respect to SEQ ID NO: 22, at position 314 with respect to SEQ ID NO: 23, at position 307 with respect to SEQ ID NO: 24, at position 315 with respect to SEQ ID NO: 25, at position 316 with respect to SEQ ID NO: 26, and at position 311 with respect to SEQ ID NO: 27. In particular, said substitution of said methionine at said position may be selected from F, Y, V, E or T. Said amino acid sequence selected from said SEQ ID NO: 1, 2, 3, 8, 9, 10, 11, 12, 13, 14, 15, 16, 17, 18, 19, 20, 21, 22, 23, 24, 25, 26 or 27 may further comprise a substitution of valine at position 234 with respect to SEQ ID NO: 1, at position 240 with respect to SEQ ID NO: 2, at position 240 with respect to SEQ ID NO: 3, at position 232 with respect to SEQ ID NO: 9, at position 240 with respect to SEQ ID NO: 10, at position 196 with respect to SEQ ID NO: 11, at position 240 with respect to SEQ ID NO: 12, at position 229 with respect to SEQ ID NO: 13, at position 236 with respect to SEQ ID NO: 14, at position 236 with respect to SEQ ID NO: 15, at position 241 with respect to SEQ ID NO: 16, at position 233 with respect to SEQ ID NO: 17, at position 240 with respect to SEQ ID NO: 18, at position 240 with respect to SEQ ID NO: 19, at position 234 with respect to SEQ ID NO: 20, at position 233 with respect to SEQ ID NO: 21, at position 237 with respect to SEQ ID NO: 22, at position 238 with respect to SEQ ID NO: 23, at position 231 with respect to SEQ ID NO: 24, at position 239 with respect to SEQ ID NO: 25, at position 240 with respect to SEQ ID NO: 26, and at position 235 with respect to SEQ ID NO: 27. In particular, said substitution of said valine at said position may be alanine or glycine.

In further embodiments of the above composition, the amino acid sequence at least 90 percent identical to SEQ ID NO: 2 or 3 further comprises a substitution of alanine at position 410 with respect to SEQ ID NO: 2 or 3. In some embodiments, the substitution of alanine at position 410 is valine.

In one aspect, the invention is directed to methods and kits for synthesizing a polyribonucleotide having a predetermined sequence comprising the steps of: a) providing an initiator having a 3'-terminal nucleotide having a free 3'-hydroxyl; and b) repeating cycles of (i) contacting under elongation conditions the initiator or elongated fragments having free 3'-O-hydroxyls with a 3'-O-blocked ribonucleoside triphosphate and a poly(A) polymerase so that the initiator or elongated fragments are elongated by incorporation of a 3'-O-blocked ribonucleoside triphosphate to form 3'-O-blocked elongated fragments, and (ii) deblocking the elongated fragments to form elongated fragments having free 3'-hydroxyls, until the polynucleotide is formed. In some embodiments, methods of the invention further include a step of cleaving the polynucleotide from the initiator. In some embodiments, the 3'-O-blocked ribonucleoside triphosphate is a 3'-O-azidomethyl-ribonucleoside triphosphate.

In another aspect, the invention is directed to a kit for performing template-free synthesis of a polyribonucleotide having a predetermined sequence, the kit comprising a poly(A) polymerase, an initiator attached to a solid support, and 3'-O-blocked ribonucleoside triphosphate monomers. Said 3'-O-protected ribonucleoside triphosphate monomers may comprise one or more of 3'-O-azidomethyl-riboadenosine triphosphate, 3'-O-azidomethyl-riboguanosine triphosphate, 3'-O-azidomethyl-ribocytidine triphosphate, 3'-O-azidomethyl-ribothymidine triphosphate and 3'-O-amino-ribouridine triphosphate. Said poly(A) polymerase may comprise a poly(A) polymerase variant having an amino acid sequence that is at least 90 percent identical to SEQ ID NO: 1 and having a substitution at M310, or at least 90 percent identical to SEQ ID NO: 3 and having a substitution at M318; wherein the poly(A) polymerase variant is capable of (a) synthesizing a ribonucleic acid fragment without a template and (b) incorporating said 3'-O-azidomethyl-ribonucleoside triphosphate onto a ribonucleic acid fragment.

In another aspect, the invention is directed to poly(A) polymerase variants comprising an amino acid sequence that is at least 90 percent identical to an amino acid sequence selected from SEQ ID NO: 1, 2, 3, 8, 9, 10, 11, 12, 13, 14, 15, 16, 17, 18, 19, 20, 21, 22, 23, 24, 25, 26 or 27 with a substitution of methionine at position 310 with respect to SEQ ID NO: 1, at position 318 with respect to SEQ ID NO: 2, at position 318 with respect to SEQ ID NO: 3, at position 316 with respect to SEQ ID NO: 8, at position 309 with respect to SEQ ID NO: 9, at position 316 with respect to SEQ ID NO: 10, at position 272 with respect to SEQ ID NO: 11, at position 316 with respect to SEQ ID NO: 12, at position 307 with respect to SEQ ID NO: 13, at position 313 with respect to SEQ ID NO: 14, at position 312 with respect to SEQ ID NO: 15, at position 317 with respect to SEQ ID NO: 16, at position 316 with respect to SEQ ID NO: 17, at position 316 with respect to SEQ ID NO: 18, at position 312 with respect to SEQ ID NO: 19, at position 310 with respect to SEQ ID NO: 20, at position 309 with respect to SEQ ID NO: 21, at position 317 with respect to SEQ ID NO: 22, at position 314 with respect to SEQ ID NO: 23, at position 307 with respect to SEQ ID NO: 24, at position 315 with respect to SEQ ID NO: 25, at position 316 with respect to SEQ ID NO: 26, and at position 311 with respect to SEQ ID NO: 27, wherein the PAP variant is capable of (a) synthesizing a ribonucleic acid fragment without a template and (b) incorporating a 3'-O-azidomethyl-ribonucleoside triphosphate onto a ribonucleic acid fragment or a 3'-O-azidomethyl-2'-deoxyribonucleoside triphosphate into a deoxyribonucleic acid fragment. In particular, said substitution of said methionine at said position may be selected from F, Y, V, E or T. Poly(A) polymerase variants may further comprise a substitution of valine at position 234 with respect to SEQ ID NO: 1, at position 240 with respect to SEQ ID NO: 2, at position 240 with respect to SEQ ID NO: 3, at position 232 with respect to SEQ ID NO: 9, at position 240 with respect to SEQ ID NO: 10, at position 196 with respect to SEQ ID NO: 11, at position 240 with respect to SEQ ID NO: 12, at position 229 with respect to SEQ ID NO: 13, at position 236 with respect to SEQ ID NO: 14, at position 236 with respect to SEQ ID NO: 15, at position 241 with respect to SEQ ID NO: 16, at position 233 with respect to SEQ ID NO: 17, at position 240 with respect to SEQ ID NO: 18, at position 240 with respect to SEQ ID NO: 19, at position 234 with respect to SEQ ID NO: 20, at position 233 with respect to SEQ ID NO: 21, at position 237 with respect to SEQ ID NO: 22, at position 238 with respect to SEQ ID NO: 23, at position 231 with respect to SEQ ID NO: 24, at position 239 with respect to SEQ ID NO: 25, at position 240 with respect to SEQ ID NO: 26, and at position 235 with respect to SEQ ID NO: 27. In particular, said substitution of valine at said position may be alanine or glycine.

In another aspect, the invention is directed to poly(U) polymerase (PUP) variants each comprising an amino acid sequence that is at least 90 percent identical to an amino acid sequence selected from SEQ ID NO: 4, 28, 29, 30, 31, 32, 33, 34, 35, 36, 37, 38, 39, 40, 41, 42, 43, 44, 45, 46 or 47 with a substitution of tyrosine at position 212 with respect to SEQ ID NO: 4, at position 189 with respect to SEQ ID NO: 28, at position 184 with respect to SEQ ID NO: 29, at position 227 with respect to SEQ ID NO: 30, at position 478 with respect to SEQ ID NO: 31, at position 192 with respect to SEQ ID NO: 32, at position 186 with respect to SEQ ID NO: 33, at position 243 with respect to SEQ ID NO: 34, at position 196 with respect to SEQ ID NO: 35, at position 253 with respect to SEQ ID NO: 36, at position 284 with respect to SEQ ID NO: 37, at position 182 with respect to SEQ ID NO: 38, at position 187 with respect to SEQ ID NO: 39, at position 203 with respect to SEQ ID NO: 40, at position 224 with respect to SEQ ID NO: 41, at position 204 with respect to SEQ ID NO: 42, at position 337 with respect to SEQ ID NO: 43, at position 296 with respect to SEQ ID NO: 44, at position 291 with respect to SEQ ID NO: 45, at position 218 with respect to SEQ ID NO: 46, and at position 366 with respect to SEQ ID NO: 47, wherein the PUP variant is capable of (a) synthesizing a ribonucleic acid fragment without a template and (b) incorporating a 3'-O-azidom-ethyl-ribonucleoside triphosphate onto a ribonucleic acid fragment or a 3'-O-azidomethyl-2'-deoxyribonucleoside triphosphate into a deoxyribonucleic acid fragment. In particular, said substitution of said tyrosine at said position may be alanine or glycine.

The present invention advantageously overcomes the above problems in the field of enzymatic polynucleotide synthesis by providing template-free polymerases and 3'-O-modified ribonucleoside triphosphates that provide higher rates of ribonucleotide incorporation into a growing RNA fragment.

DETAILED DESCRIPTION OF THE INVENTION

Figure 1:
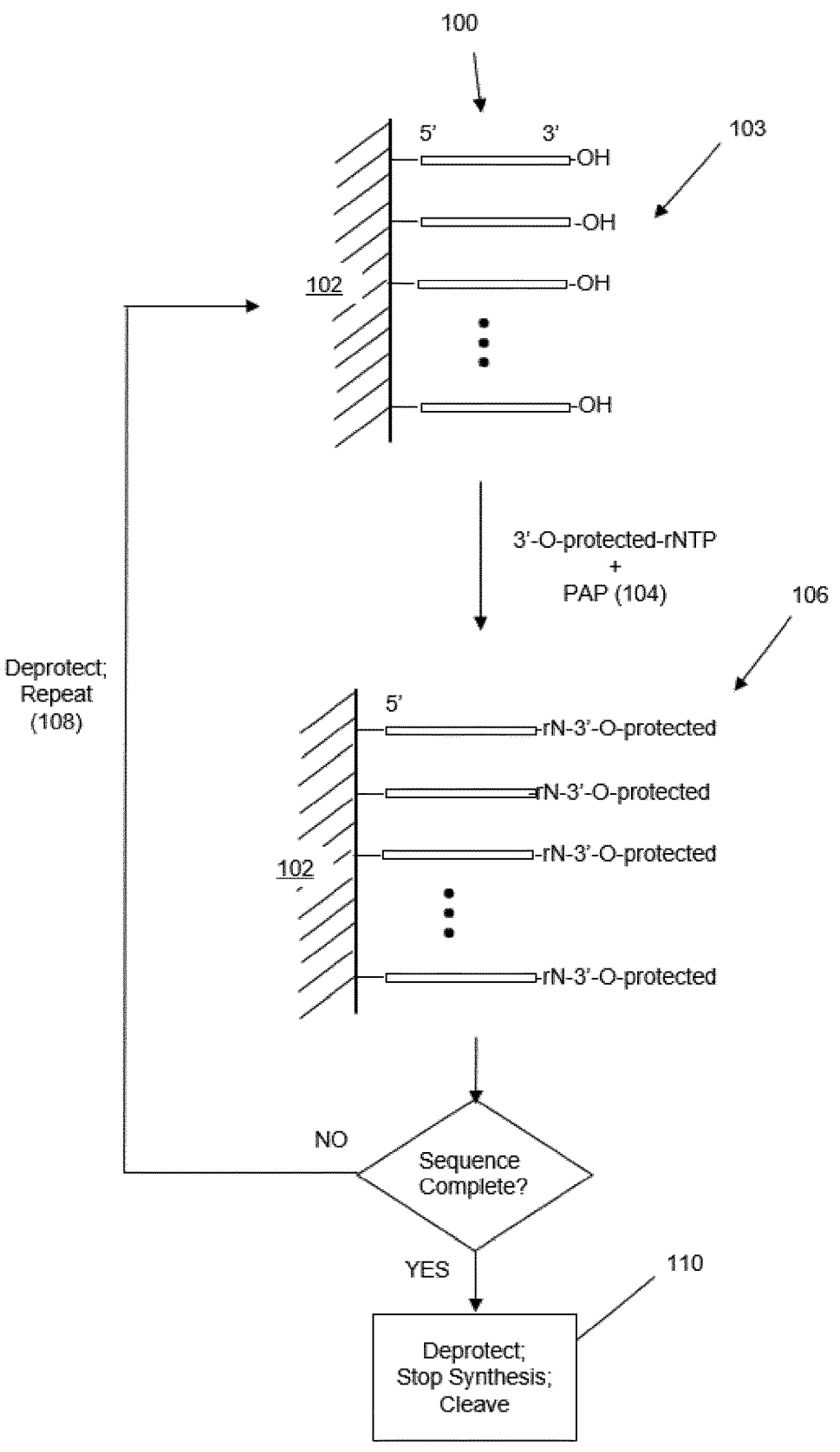
FIG. 1 illustrates steps of an embodiment of the method of the invention.

The general principles of the invention are disclosed in more detail herein particularly by way of examples, such as those shown in the drawings and described in detail. It should be understood, however, that the intention is not to limit the invention to the particular embodiments described. The invention is amenable to various modifications and alternative forms, specifics of which are shown for several embodiments. The intention is to cover all modifications, equivalents, and alternatives falling within the principles and scope of the invention.

The practice of the present invention may employ, unless otherwise indicated, conventional techniques and descriptions of organic chemistry, molecular biology (including recombinant techniques), cell biology, and biochemistry, which are within the skill of the art. Such conventional techniques may include, but are not limited to, preparation and use of synthetic peptides, synthetic polynucleotides, monoclonal antibodies, nucleic acid cloning, amplification, sequencing and analysis, and related techniques. Protocols for such conventional techniques can be found in product literature from manufacturers and in standard laboratory manuals, such as Genome Analysis: A Laboratory Manual Series (Vols. I-IV); PCR Primer: A Laboratory Manual; and Molecular Cloning: A Laboratory Manual (all from Cold Spring Harbor Laboratory Press); Lutz and Bornscheuer, Editors, Protein Engineering Handbook (Wiley-VCH, 2009); Hermanson, Bioconjugate Techniques, Second Edition (Academic Press, 2008); and like references.

The invention is directed to methods and compositions for synthesizing polynucleotides, either polyribonucleic acids or polydeoxyribonucleic acids, using a poly(A) polymerase (PAP), poly(U) polymerase (PUP) or both PAPs and PUPs in the same synthesis. In some embodiments, PAPs and/or PUPs are used to synthesize a polyribonucleic acid using 3'-O-reversibly protected-rNTP precursors, wherein a single PUP or PAP variant may be employed for coupling all ribonucleoside triphosphate monomers, or in alternative embodiments, wherein different PUPs and PAPs may be employed for coupling different kinds ribonucleoside triphosphate monomers in the synthesis of a particular RNA. Likewise, in other embodiments, PAPs and/or PUPs be used to synthesize a polydeoxyribonucleic acid using 3'-O-reversibly protected-dNTP precursors, wherein a single PUP or PAP is employed for coupling all deoxyribonucleoside triphosphate (dNTP) monomers, or in an alternative embodiment, wherein different PUP and PAP polymerases may be employed for coupling different kinds of deoxyribonucleoside triphosphate monomers. In some embodiments, methods of the invention employ PAP and/or PUP variants that have been modified by genetic engineering to improve efficiency of coupling 3'-O-blocked-ribonucleoside triphosphates and 3'-O-blocked-2'-deoxyribonucleoside triphosphates to growing polynucleotide chains in a synthesis.

Methods of the invention, whether for synthesizing RNA or DNA, comprise repeated cycles of steps, such as are illustrated in FIG. 1, in which a predetermined ribonucleotide monomer for RNA synthesis (or 2'-deoxyribonucleotide monomer for DNA synthesis) is added in each cycle. Initiator polynucleotides (100) are provided, for example, attached to solid support (102), which have free 3'-hydroxyl groups (103). For synthesizing RNA, typically initiators are polyribonucleotides, and for synthesizing DNA, typically initiators are polydeoxyribonucleotides. To the initiator polynucleotides (100) (or elongated initiator polynucleotides in subsequent cycles) are added a 3'-O-reversibly protected-rNTP (or 3'-O-reversibly protected-dNTP in case of DNA synthesis) and a PAP or PUP under conditions (104) effective for the enzymatic incorporation of the 3'-O-protected-rNTP (or 3'-O-protected dNTP) onto the 3' end of the initiator polynucleotides (100) (or elongated initiator polynucleotides). This reaction produces elongated initiator polynucleotides whose 3'-hydroxyls are protected (106). If the elongated initiator polynucleotide contains a completed sequence, then the 3'-O-protection group is removed, or deprotected, and the desired sequence is cleaved from the original initiator polynucleotide. Such cleavage may be carried out using any of a variety of single strand cleavage techniques, for example, by inserting a cleavable nucleotide at a predetermined location within the original initiator polynucleotide. An exemplary cleavable nucleotide may be a uracil nucleotide which is cleaved by uracil DNA glycosylase. Additionally a wide variety of cleavable linkages or cleavable nucleotides may be used for this purpose. In some embodiments, cleaving the desired polynucleotide leaves a natural free 5'-hydroxyl on a cleaved strand; however, in alternative embodiments, a cleaving step may leave a moiety, e.g. a 5'-phosphate, that may be removed in a subsequent step, e.g. by phosphatase treatment. Cleaving steps may be carried out chemically, thermally, enzymatically or by photochemical methods. In some embodiments, cleavable nucleotides may be nucleotide analogs such as deoxyuridine or 8-oxo-deoxyguanosine that are recognized by specific glycosylases (e.g. uracil deoxyglycosylase followed by endonuclease VIII, and 8-oxoguanine DNA glycosylase, respectively). In some embodiments, cleavage may be accomplished by providing initiators with a deoxyinosine as the penultimate 3' nucleotide, which may be cleaved by endonuclease V at the 3' end of the initiator leaving a 5'-phosphate on the released polynucleotide. Further methods for cleaving single stranded polynucleotides are disclosed in the following references, which are incorporated by reference: U.S. Pat. Nos. 5,739,386, 5,700,642 and 5,830,655; and U.S. Patent Publication Nos. 2003/0186226 and 2004/0106728; and in Urdea and Horn, U.S. Pat. No. 5,367,066.

If the elongated initiator polynucleotide does not contain a completed sequence, then the 3'-O-protection groups are removed to expose free 3'-hydroxyls (103) and the elongated initiator polynucleotides are subjected to another cycle of ribonucleotide addition and deprotection.

In some embodiments, the method of synthesizing an oligoribonucleotide comprises the steps of (a) providing an initiator having a free 3'-hydroxyl; (b) reacting under extension conditions the initiator or an extension intermediate (i.e. an elongated initiator polynucleotide) having a free 3'-hydroxyl with a PAP in the presence of a 3'-O-blocked ribonucleoside triphosphate to produce a 3'-O-blocked extension intermediate; (c) deblocking the extension intermediate to produce an extension intermediate with a free 3'-hydroxyl; and (d) repeating steps (b) and (c) until the polyribonucleotide is synthesized. (The term "an extension intermediate" may also be referred to herein as an "elongation fragment" or an "elongated initiator polynucleotide".) In some embodiments, as noted above, an initiator is provided as an oligonucleotide attached to a solid support, e.g. by its 5' end. The above method may also include washing steps after the reaction, or extension, step, as well as after the de-blocking step. For example, the step of reacting may include a sub-step of removing unincorporated ribonucleoside triphosphates, e.g. by washing, after a predetermined incubation period, or reaction time. Such predetermined incubation periods or reaction times may be a few seconds, e.g. 30 sec, to several minutes, e.g. 30 min.

In some embodiments, the method of synthesizing an oligoribonucleotide comprises the steps of (a) providing an initiator having a free 3'-hydroxyl; (b) reacting under extension conditions the initiator or an extension intermediate (i.e. an elongated initiator polynucleotide) having a free 3'-hydroxyl with a PAP or a PUP in the presence of a 3'-O-blocked ribonucleoside triphosphate to produce a 3'-O-blocked extension intermediate; (c) deblocking the extension intermediate to produce an extension intermediate with a free 3'-hydroxyl; and (d) repeating steps (b) and (c) until the polyribonucleotide is synthesized. (The term "an extension intermediate" may also be referred to herein as an "elongation fragment" or an "elongated initiator polynucleotide".) In some embodiments, as noted above, an initiator is provided as an oligonucleotide attached to a solid support, e.g. by its 5' end. The above method may also include washing steps after the reaction, or extension, step, as well as after the de-blocking step. For example, the step of reacting may include a sub-step of removing unincorporated ribonucleoside triphosphates, e.g. by washing, after a predetermined incubation period, or reaction time. Such predetermined incubation periods or reaction times may be a few seconds, e.g. 30 sec, to several minutes, e.g. 30 min.

In some embodiments, the method of synthesizing a polynucleotide comprises the steps of (a) providing an initiator having a free 3'-hydroxyl; (b) reacting under extension conditions the initiator or an extension intermediate (i.e. an elongated initiator polynucleotide) having a free 3'-hydroxyl with a PAP or a PUP in the presence of a 3'-O-blocked nucleoside triphosphate to produce a 3'-O-blocked extension intermediate; (c) deblocking the extension intermediate to produce an extension intermediate with a free 3'-hydroxyl; and (d) repeating steps (b) and (c) until the polynucleotide is synthesized. (The term "an extension intermediate" may also be referred to herein as an "elongation fragment" or an "elongated initiator polynucleotide".)

In some embodiments, as noted above, an initiator is provided as an oligonucleotide attached to a solid support, e.g. by its 5' end. The above method may also include washing steps after the reaction, or extension, step, as well as after the de-blocking step. For example, the step of reacting may include a sub-step of removing unincorporated ribonucleoside triphosphates, e.g. by washing, after a predetermined incubation period, or reaction time. Such predetermined incubation periods or reaction times may be a few seconds, e.g. 30 sec, to several minutes, e.g. 30 min.

The above method may also include capping step(s) as well as washing steps after the reacting, or extending, step, as well as after the deblocking step. As mentioned above, in some embodiments, capping steps may be included in which non-extended free 3'-hydroxyls are reacted with compounds that prevents any further extensions of the capped strand. In some embodiments, such compound may be a dideoxynucleoside triphosphate. In other embodiments, non-extended strands with free 3'-hydroxyls may be degraded by treating them with a 3'-exoribonuclease activity, e.g. RNase R (Epicentre). Likewise, in some embodiments, strands that fail to be deblocked may be treated to either remove the strand or render it inert to further extensions.

In some embodiments that comprise serial synthesis of oligoribonucleotides, capping steps may be undesirable as capping may prevent the production of equal molar amounts of a plurality of oligonucleotides. Without capping, sequences will have a uniform distribution of deletion errors, but each of a plurality of oligoribonucleotides will be present in equal molar amounts. This would not be the case where non-extended fragments are capped.

In some embodiments, reaction conditions for an extension or elongation step using PAP or PUP may comprising the following: Reaction conditions 1 (for primer+AM-rATP): 250 uM AM-rATP, 0.1 uM ATTO488-(rA)5, 1 uM PAP, 1×ATP buffer (20 mM Tris-HCl, 0.6 mM MnCl2, 0.02 mM EDTA, 0.1% BSA, 10% glycerol, 100 mM imidazole, pH 7-8), 37 C, 30 min. Reaction condition 2 (for primer+AM-rGTP): 250 uM rGTP, 0.1 uM ATTO488-(rA)5, 1 uM PAP, 1×GTP buffer (0.6 mM MnCl2, 0.1% BSA, 10 mM imidazole, pH 6), 37 C, 30 min. In the foregoing, "AM-rNTP" refers to 3'-azidomethyl-O-ribonucleoside triphosphate.

Depending on particular applications, the steps of deblocking and/or cleaving may include a variety of chemical or physical conditions, e.g. light, heat, pH, presence of specific reagents, such as enzymes, which are able to cleave a specified chemical bond. Guidance in selecting 3'-O-blocking groups and corresponding de-blocking conditions may be found in references, such as Wuts, Green's Protection Groups in Organic Chemistry, 5th Edition (Wiley 2014). In some embodiments, the cleaving agent (also sometimes referred to as a de-blocking reagent or agent) is a chemical cleaving agent, such as, for example, dithiothreitol (DTT). In alternative embodiments, a cleaving agent may be an enzymatic cleaving agent, such as, for example, a phosphatase, which may cleave a 3'-phosphate blocking group. It will be understood by the person skilled in the art that the selection of deblocking agent depends on the type of 3'-nucleotide blocking group used, whether one or multiple blocking groups are being used, whether initiators are attached to living cells or organisms or to solid supports, and the like, that necessitate mild treatment. For example, a phosphine, such as tris(2-carboxyethyl)phosphine (TCEP) can be used to cleave a 3'O-azidomethyl group, palladium complexes can be used to cleave 3'O-allyl group and 3'-O-propargyl group, or sodium nitrite can be used to cleave a 3'O-amino group.

As noted above, in some embodiments it is desirable to employ two or more blocking groups that may be removed using orthogonal de-blocking conditions. The following exemplary pairs of blocking groups may be used in parallel synthesis embodiments in which two or more sequences are synthesized in the same reaction mixture. It is understood that other blocking group pairs, or groups containing more than two, may be available for use in these embodiments of the invention.

| | |
|---|---|
| 3'-O-NH2 | 3'-O-azidomethyl |
| 3'-O-NH2 | 3'-O-allyl, 3'O-propargyl |
| 3'-O-NH2 | 3'-O-phosphate |
| 3'-O-azidomethyl | 3'-O-allyl, 3'O-propargyl |
| 3'-O-azidomethyl | 3'-O-phosphate |
| 3'-O-allyl, 3'O-propargyl | 3'-O-phosphate |

As used herein, an "initiator" (or equivalent terms, such as, "initiating fragment," "initiator nucleic acid," "initiator oligonucleotide," or the like) refers to a short oligonucleotide sequence with a free 3'-end, which can be further elongated by a template-free polymerase, such as PAP or PUP. In one embodiment, the initiating fragment is a DNA or RNA initiating fragment. In an alternative embodiment, the initiating fragment is an RNA initiating fragment. In one embodiment, the initiating fragment possesses between 3 and 100 nucleotides, in particular between 3 and 20 nucleotides. In one embodiment, the initiating fragment is single-stranded. In an alternative embodiment, the initiating fragment is double-stranded. In a particular embodiment, an initiator oligonucleotide synthesized with a 5'-primary amine may be covalently linked to magnetic beads using the manufacturer's protocol. Likewise, an initiator oligonucleotide synthesized with a 3'-primary amine may be covalently linked to magnetic beads or agarose beads using the manufacturer's protocol. A variety of other attachment chemistries amenable for use with embodiments of the invention are well-known in the art, e.g. Integrated DNA Technologies brochure, "Strategies for Attaching Oligonucleotides to Solid Supports," v.6 (2014); Hermanson, Bioconjugate Techniques, Second Edition (Academic Press, 2008); and like references.

Many of the 3'-O-blocked rNTPs employed in the invention may be purchased from commercial vendors (e.g. Jena Bioscience, MyChemLabs, or the like) or synthesized using published techniques, e.g. U.S. Pat. No. 7,057,026; International patent publications WO2004/005667, WO91/06678; Canard et al, Gene (cited above); Metzker et al, Nucleic Acids Research, 22: 4259-4267 (1994); Meng et al, J. Org. Chem., 14: 3248-3252 (3006); U.S. patent publication 2005/037991; Zavgorodny et al, Tetrahedron Letters, 32(51): 7593-7596 (1991).

In a further particular embodiments, the 3'-blocked nucleotide triphosphate is blocked by either 3'-O-propargyl, a 3'-O-azidomethyl, 3'-O—NH2 or 3'-O-allyl group.

In still other embodiments, 3'-O-blocking groups of the invention include 3'-O-methyl, 3'-O-(2-nitrobenzyl), 3'-O-allyl, 3'-O-amine, 3'-O-azidomethyl, 3'-O-tert-butoxy ethoxy, 3'-O-(2-cyanoethyl), and 3'-O-propargyl.

Poly(A) Polymerases and Useful Variants

A wide variety of PAPs may be used with the method of the invention, including PAP variants that have been engineered for improved characteristics, such as, higher incorporation rates of 3'-O-protected-rNTPs (including for particular protection groups, such as, 3'-O-azidomethyl), greater stability and shelf life, thermostability, solubility, and the like. In particular, a yeast PAP with a mutation at M310 (SEQ ID NO: 1), or a functionally equivalent residue in other PAPs, such as PAPs from various different species, shows improved incorporation of 3'-O-protected rNTPs with respect to a wildtype PAP. In some embodiments, a yeast PAP variant of the invention has an amino acid sequence of SEQ ID NO: 1 except for a substitution at M310. In some embodiments, such substitution is selected from M310F/Y/V/E/T. In particular, substitutions M310F/Y allow the incorporation of 3'-O-amino-rATPs and substitutions M310V/E/T improve the rate of incorporation of 3'-O-protected-rGTPs. In other embodiments, a yeast PAP variant of the invention has an amino acid sequence with at least 90 percent identity of SEQ ID NO: 1 except for a substitution at M310.

PAP variants for use with the invention include those listed in Table 1 below. In some embodiments PAP variants of the invention comprise at least a substitution at the second position indicated in Table 1. In other embodiments, embodiments of PAP variants of the invention comprise at least a substitution at the first position indicated in Table 1.

TABLE 1

| PAP Variants: Positions of Substitutions | | | |
|---|---|---|---|
| SEQ ID NO | Organism | First Position | Second Position |
| 1 | yeast | V234 | M310 |
| 2 | Myceliophthora | V240 | M318 |
| 3 | Thielavia | V240 | M318 |
| 8 | Pyronema | I237 | M316 |
| 9 | Tilletia | V232 | M309 |
| 10 | Clathrospora | V240 | M316 |
| 11 | Drechslerella | V196 | M272 |
| 12 | Magnaporthiopsis | V240 | M316 |
| 13 | Cryptococcus | V229 | M307 |
| 14 | Golovinomyces | V236 | M313 |
| 15 | Hortaea | V236 | M312 |
| 16 | Valsa | V241 | M317 |
| 17 | Wallemia | V233 | M316 |
| 18 | Xylaria | V240 | M316 |
| 19 | Chaetomium | V240 | M312 |
| 20 | Lachancea | V234 | M310 |
| 21 | Schizosaccharomyces | V233 | M309 |
| 22 | Exophiala | V237 | M317 |
| 23 | Scedosporium | V238 | M314 |
| 24 | Trichoderma | V231 | M307 |
| 25 | Aspergillus | V239 | M315 |
| 26 | Sodiomyces | V240 | M316 |
| 27 | Neohortaea | V235 | M311 |

In some embodiments, a substitution at a first position as indicated in Table 1 is A or G (thus, for example, for SEQ ID NO:1, the substitution may be written V234A/G). In some embodiments, a substitution at a second position as indicated in Table 1 is F, Y, V, E, or T (thus, for example, for SEQ ID NO: 1, the substitution may be written M310F/Y/V/E/T)

In some embodiments, a PAP variant of the invention has one or more of the substitutions of Table 1 and a percent identity value of at least 80 percent identity with the indicated SEQ ID NO; in some embodiments, the above percent identity value is at least 90 percent identity with the indicated SEQ ID NO; in some embodiments, the above percent identity value is at least 95 percent identity with the indicated SEQ ID NO; in some embodiments, the above percent identity value is at least 97 percent identity; in some embodiments, the above percent identity value is at least 98 percent identity; in some embodiments, the above percent identity value is at least 99 percent identity.

In some embodiments, a thermostable PAP is employed so that the method may be practiced at a temperature that reduces or eliminates the formation of secondary structures in the RNA or DNA being synthesized. In some embodiments, the temperature range within which the highest incorporation rate occurs for the thermostable PAP is higher than 40° C. In some embodiments, the temperature range within which the highest incorporation rate occurs for the thermostable PAP is higher than 50° C. In some embodiments, the temperature range within which the highest incorporation rate occurs for the thermostable PAP is between 40° C. and 85° C. In some embodiments, the temperature range within which the highest incorporation rate occurs for the thermostable PAP is between 50° C. and 85° C.

Poly(U) Polymerases and Useful Variants

As with PAPs, a wide variety of PUPs may be used with the method of the invention, including PUP variants that have been engineered for improved characteristics, such as, higher incorporation rates of 3'-O-protected-rNTPs (including for particular protection groups, such as, 3'-O-azidomethyl), greater stability and shelf life, thermostability, solubility, and the like. PUP variants for use with the invention include those listed in Table 2 below. In some embodiments PUP variants of the invention comprise at least a substitution at the first position indicated in Table 2. In other embodiments, embodiments of PAP variants of the invention comprise at least a substitution at the second position indicated in Table 2.

TABLE 2

PUP Variants: Positions of Substitutions

| SEQ ID NO | Organism | First Position | Second Position |
|---|---|---|---|
| 4 | S. pombe | Y212 | H336 |
| 28 | T. brucei | Y189 | L303 |
| 29 | S. pombe | Y184 | H308 |
| 30 | T. boudieri | Y227 | H364 |
| 31 | D. stenobrocha | Y478 | H613 |
| 32 | Phytomonas | Y192 | L306 |
| 33 | B. saltans | Y186 | L326 |
| 34 | A. deanei | Y243 | L392 |
| 35 | P. lactucaedebilis | Y196 | H330 |
| 36 | S. culicis | Y253 | L392 |
| 37 | B. meristosporus | Y284 | H408 |
| 38 | N. californiae | Y182 | H310 |
| 39 | Perkinsela | Y187 | L394 |
| 40 | S. complicate | Y203 | H331 |
| 41 | S. ochraceum | Y224 | F349 |
| 42 | G. androsaceus | Y204 | Y332 |
| 43 | T. equiperdum | Y337 | L473 |
| 44 | M. conica | Y296 | H431 |
| 45 | P. murina | Y291 | H423 |
| 46 | S. japonicus | Y218 | H340 |
| 47 | A. nigricans | Y366 | H509 |

In some embodiments, a substitution at a first position as indicated in Table 2 is A or G (thus, for example, for SEQ ID NO:4, the substitution may be written Y212A/G). In some embodiments, a substitution at a second position as indicated in Table 2 is F, Y, V, E, or T (thus, for example, for SEQ ID NO: 4, the substitution may be written H336F/Y/V/E/T)

In some embodiments, a PUP variant of the invention has one or more of the substitutions of Table 2 and a percent identity value of at least 80 percent identity with the indicated SEQ ID NO; in some embodiments, the above percent identity value is at least 90 percent identity with the indicated SEQ ID NO; in some embodiments, the above percent identity value is at least 95 percent identity with the indicated SEQ ID NO; in some embodiments, the above percent identity value is at least 97 percent identity; in some embodiments, the above percent identity value is at least 98 percent identity; in some embodiments, the above percent identity value is at least 99 percent identity.

In some embodiments, a thermostable PUP is employed so that the method may be practiced at a temperature that reduces or eliminates the formation of secondary structures in the RNA or DNA being synthesized. In some embodiments, the temperature range within which the highest incorporation rate occurs for the thermostable PUP is higher than 40° C. In some embodiments, the temperature range within which the highest incorporation rate occurs for the thermostable PUP is higher than 50° C. In some embodiments, the temperature range within which the highest incorporation rate occurs for the thermostable PUP is between 40° C. and 85° C. In some embodiments, the temperature range within which the highest incorporation rate occurs for the thermostable PUP is between 50° C. and 85° C.

Production of PAP and PUP Variants

Variants of the invention may be produced by mutating known reference or wild type PAP-coding or PUP-coding polynucleotides, then expressing it using conventional molecular biology techniques. For example, a desired gene or DNA fragment encoding a polypeptide of desired sequence may be assembled from synthetic fragments using conventional molecular biology techniques, e.g. using protocols described by Stemmer et al, Gene, 164: 49-53 (1995); Kodumal et al, Proc. Natl. Acad. Sci., 101: 15573-15578 (2004); or the like, or such gene or DNA fragment may be directly cloned from cells of a selected species using conventional protocols.

An isolated gene encoding a desired PAP or PUP variant may be inserted into an expression vector to give an expression vector which then may be used to make and express variant PAP or PUP proteins using conventional protocols. Vectors with the correct sequence may be transformed in E. coli producer strains.

The following procedures are described for PAP variants, but similar procedures may be applied by one of ordinary skill in the art to PUP variants. Transformed strains are cultured using conventional techniques to pellets from which PAP protein is extracted. For example, previously prepared pellets are thawed in 30 to 37° C. water bath. Once fully thawed, pellets are resuspended in lysis buffer composed of 50 mM tris-HCL (Sigma) pH 7.5, 150 mM NaCl (Sigma), 0.5 mM mercaptoethanol (Sigma), 5% glycerol (Sigma), 20 mM imidazole (Sigma) and 1 tab for 100 mL of protease cocktail inhibitor (Thermofisher). Careful resuspension is carried out in order to avoid premature lysis and remaining of aggregates. Resuspended cells are lysed through several cycles of French press, until full color homogeneity is obtained. Usual pressure used is 14,000 psi. Lysate is then centrifuged for 1 h to 1 h30 at 10,000 rpm. Centrifugate is pass through a 0.2 µm filter to remove any debris before column purification.

PAP protein may be purified from the centrifugate in a one-step affinity procedure. For example, Ni-NTA affinity column (GE Healthcare) may be used to bind the PAP polymerases. Initially the column is washed and equilibrated with 15 column volumes of 50 mM tris-HCL (Sigma) pH 7.5, 150 mM NaCl (Sigma) and 20 mM imidazole (Sigma). PAP polymerases are bound to the column after equilibration; then, a washing buffer, for example, composed of 50 mM tris-HCL (Sigma) pH 7.5, 500 mM NaCl (Sigma) and 20 mM imidazole (Sigma), may be applied to the column for 15 column volumes. After such washing, the PAP polymerases are eluted with 50 mM tris-HCL (Sigma) pH 7.5, 500 mM NaCl (Sigma) and 0.5M imidazole (Sigma). Fractions corresponding to the highest concentration of PAP polymerases of interest are collected and pooled in a single sample. The pooled fractions are dialyzed against the dialysis buffer (20 mM Tris-HCl, pH 6.8, 200 mM Na Cl, 50 mM MgOAc, 100 mM [NH4]2SO4). The dialysate is subsequently concentrated with the help of concentration filters (Amicon Ultra-30, Merk Millipore). Concentrated enzyme is distributed in small aliquots, 50% glycerol final is added, and those aliquots are then frozen at −20° C. and stored for long term. 5 μL of various fraction of the purified enzymes are analyzed in SDSPAGE gels.

In some embodiments, a PAP variant may be operably linked to a linker moiety including a covalent or non-covalent bond; amino acid tag (e.g., poly-amino acid tag, poly-His tag, 6His-tag, or the like); chemical compound (e.g., polyethylene glycol); protein-protein binding pair (e.g., biotin-avidin); affinity coupling; capture probes; or any combination of these. The linker moiety can be separate from or part of a PAP variant. An exemplary His-tag for use with PAP variants of the invention is MASSHHHHHHSSGSENLYFQTGSSG-(SEQ ID NO: 5)). The tag-linker moiety does not interfere with the nucleotide binding activity, or catalytic activity of the PAP variant.

The above processes, or equivalent processes, result in an isolated PAP or PUP variant that may be mixed with a variety of reagents, such as, salts, pH buffers, carrier compounds, and the like, that are necessary or useful for activity and/or preservation.

Measurement of Nucleotide Incorporation Activity

The efficiency of nucleotide incorporation by variants of the invention may be measured by an extension, or elongation, assay, e.g. as described in Boule et al (cited below); Bentolila et al (cited below); and Hiatt et al, U.S. Pat. No. 5,808,045, the latter of which is incorporated herein by reference. Briefly, in one form of such an assay, a fluorescently labeled oligonucleotide having a free 3'-hydroxyl is reacted under PAP extension conditions with a PAP variant to be tested for a predetermined duration in the presence of a reversibly blocked ribonucleoside triphosphate, after which the extension reaction is stopped and the amounts of extension products and unextended initiator oligonucleotide are quantified after separation by gel electrophoresis. By such assays, the incorporation efficiency of a PAP variant may be readily compared to the efficiencies of other variants or to that of wild type or reference PAPs, or other polymerases. In some embodiments, a measure of PAP variant efficiency may be a ratio (given as a percentage) of amount of extended product using the PAP variant over the amount of extended product using wild type PAP in an equivalent assay. The reagents are added in the tube, starting from water, and then in the order of Table 3.

TABLE 3

| Extension Activity Assay Reagents | | |
| --- | --- | --- |
| Reagent | Concentration | Volume |
| H₂O | — | 12 μL |
| Activity buffer | 10× | 2 μL |
| rNTP | 250 μM | 2 μL |
| Purified enzyme | 20 μM | 2 μL |
| Fluorescent primer | 500 μM | 2 μL |

The product of the assay may be analyzed by conventional polyacrylamide gel electrophoresis. For example, products of the above assay may be analyzed in a 16 percent polyacrylamide denaturing gel (Bio-Rad). Gels are made just before the analysis by pouring polyacrylamide inside glass plates and let it polymerize. The gel inside the glass plates is mounted on an adapted tank filed with TBE buffer (Sigma) for the electrophoresis step. The samples to be analyzed are loaded on the top of the gel. A voltage of 500 to 2,000V is applied between the top and bottom of the gel for 3 to 6 h at room temperature. After separation, gel fluorescence is scanned using, for example, a Typhoon scanner (GE Life Sciences). The gel image is analyzed using ImageJ software (imagej.nih.gov/ij/), or its equivalent, to calculate the percentage of incorporation of the modified nucleotides.

Kits

The invention includes kits for carrying out methods of the invention. In some embodiments, a kit of the invention comprises a poly(A) polymerase and 3'-O-blocked ribonucleoside triphosphates of one or more of adenosine, guanosine, uridine and cytidine. In other embodiments, such kit may further include a poly(U) polymerase. In some embodiments, a kit of the invention comprises a poly(A) polymerase and 3'-O-blocked-2'-deoxyribonucleoside triphosphates of one or more of deoxyadenosine, deoxyguanosine, deoxythymidine and deoxycytidine. In other embodiments, such kit may further include a poly(U) polymerase. In some embodiments, kits of the invention may include an initiator with a free 3'-hydroxyl attached to a support by a 5' end. In some embodiments, such support is a solid support. Such solid support may comprise beads, such as magnetic beads or agarose beads, a planar solid, such as a glass slide, or a membrane, or the like. In some embodiments, a kit of the invention may further include a de-blocking agent which is capable of removing 3' blocking groups from incorporated 3'-O-blocked nucleotides. In some embodiments, a kit may include an M310 mutant of a yeast PAP, such as, the yeast PAP of SEQ ID NO: 1, or a functionally equivalent residue to M310 in a PAP from a different species. In some embodiments, a kit may include a PAP variant comprising an amino acid sequence that is at least 90 percent identical to an amino acid sequence selected from SEQ ID NO: 1, 2 or 3 with a substitution of methionine at position 310 with respect to SEQ ID NO: 1, or methionine at position 318 with respect to SEQ ID NOs 2 and 3, wherein the variant capable of (a) synthesizing a ribonucleic acid fragment without a template and (b) incorporating a 3'-O-azidomethyl-ribonucleoside triphosphate onto a ribonucleic acid fragment or a 3'-O-azidomethyl-2'-deoxyribonucleoside triphosphate into a deoxyribonucleic acid fragment.

In some embodiments, in PAP variants of the foregoing kits the substitution of the methionine at position 310 of SEQ ID NO: 1 or the methionine at position 318 of SEQ ID NOs 2 or 3 is selected from M310F/Y/V/E/T. In some embodiments, in PAP variants of the foregoing kits there is a substitution of valine at position 234 with respect to SEQ ID NO: 1 and valine at position 240 with respect to SEQ ID NOs 2 and 3. In some embodiments, in PAP variants of the foregoing kits, the substitution of valine at position 234 of SEQ ID NO: 1 and position 240 with respect to SEQ ID NOs 2 and 3 is alanine. In some embodiments, in PAP variants of the foregoing kits, there is a substitution of alanine at position 410 with respect to SEQ ID NOs 2 or 3.

In some embodiments, a kit of the invention may comprise a PAP variant having an amino acid sequence at least 80 percent identical to a sequence selected from SEQ ID NOs 1-3 and 8-27 of Table 1 which has a substitution in the first position or a substitution in the second position or a substitution in both positions of such selected sequence as indicated in Table 1. In some embodiments, such percent identity of the selected sequence is at least 90 percent identity. In some embodiments, a kit of the invention may comprise a PUP variant having an amino acid sequence at least 80 percent identical to a sequence selected from SEQ ID NOs 4 and 28-47 of Table 2 which has a substitution in the first position or a substitution in the second position or a substitution in both positions of such selected sequence as indicated in Table 2. In some embodiments, such percent identity of the selected sequence is at least 90 percent identity.

Example 1

One-to-Five Ribonucleotide Additions to Initiator Polynucleotides Immobilized on a Solid Support 2-3 cycle extension of Cp-RNA primer with 3'-O-azidomethyl-ribonucleoside triphosphates (AM-NTPs) in presence of PAP (Thermo). Experimental procedure: 1) preparation of Cp-beads: 100 uL Cp-beads (~1 uM concentration of Cp primer on bead)+1 uL 100 uM SynRDA_DNA-SynRDA_RNA; incubate for 30 min at room temp, wash beads with 3×200 uL binding buffer (BB), (200 mM caco, LiCl), resuspend beads in 25 uL BB; 2)+1 addition reaction: 250 uM 3'O-terminated nucleotide; 3.2 uM Cp-SynRDA_DNA-SynRDA_RNA; 1×PAP_yeast Thermo reaction buffer; 100 U/uL PAP_yeast (Thermo); 20 uL final volume; in Eppendorf tubes; 30 min, 37° C., thermomixer, 1500 rpm, 3) wash+1 product: 3×200 uL BB 4) TCEP deprotection: resuspend beads in 50 uL 200 uM TCEP, pH 7.0 (dilution from freshly opened ampula), 37 C, 15 min, thermomixer, 1500 rpm; 5) wash deprotected+1 product: 3×200 uL binding buffer, 6)+2/deprotect/+3 addition: see 1)-5), 8) Elution+ gel: add 20 uL B-blue, vortex, elute, apply on gel. The Cp-RNA beads used were prepared the following way: i) covalent functionalization of commercial Dynabeads M-270 that display a terminal carboxylic acid group (purchased from Thermo Fisher) with a DNA oligo (TCATTTCACTCT-CACA-NH2)(SEQ ID NO: 6). These beads are named Cp-beads. Cp-beads were then incubated with a DNA-RNA hybrid primer of sequence ATTO488-TGTGAGAGT-GAAATGAGGrUrGrUrGrArGrArGrUr-GrArArArUr-GrArGrG (named SynRDA_DNA-SynRDA_RNA) (SEQ ID NO: 7).

Figure 2A:
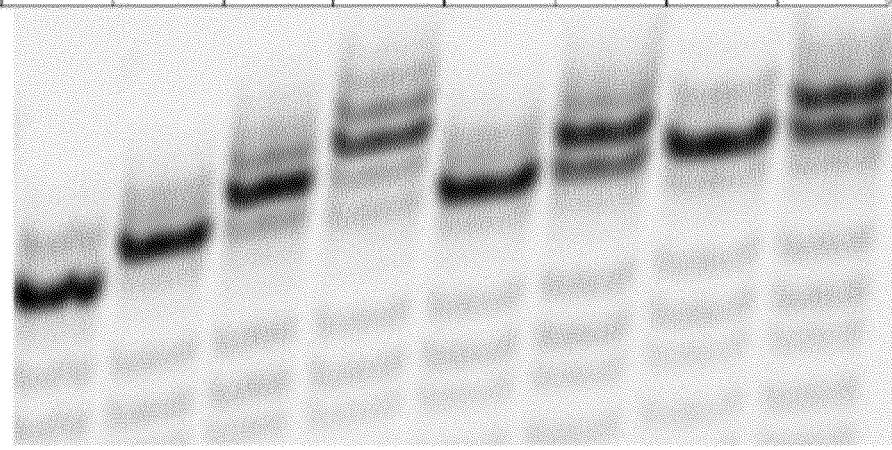
FIGS. 2A-2C shows data for extensions of from 1-5 ribonucleotides in accordance with the method of the invention.
Figure 2B:
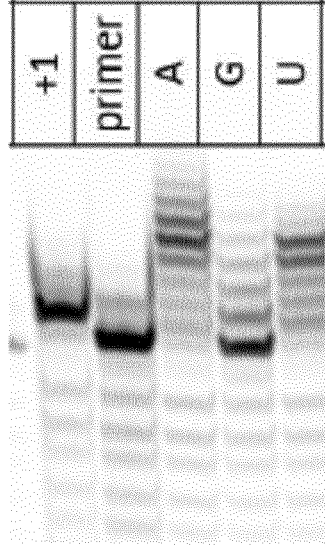
Figures 2C, 3A:
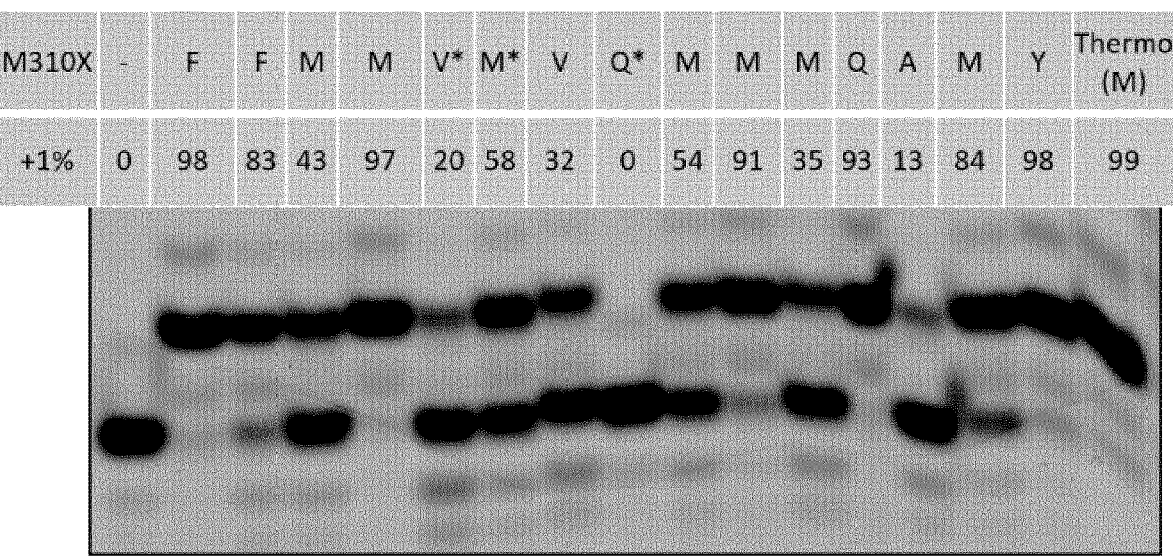
FIGS. 3A-3B show data for extensions with a single 3'-O-protected-rATP (3A) and of a polyguanylation using rGTP (3B) in presence of mutations M310F/Y/Q/A/V/E/T.

Results are shown in FIG. 2A-2C. This data show: i) with 3'-O-AM-rATP and 3'-O-AM-rUTP at least 5 cycles of addition/deprotection can be achieved with same nucleotide; ii) at least 2 cycles of addition/deprotection can be achieved with two different 3'-O-AM-rNTPs (A and U); and iii) at least >95% deprotection of 3'-O-AM-protected RNA can be achieved.

Example 2

Figure 3B:
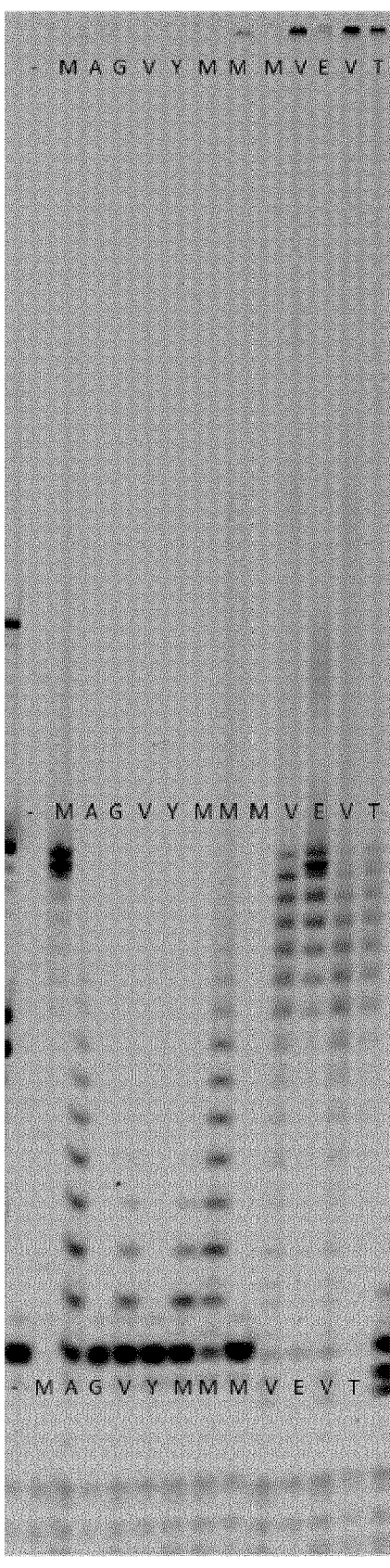

Effect of PAP M310 Mutations on Activities AM-rATP Elongation and Riboguanylation In this experiment, the effects of mutations in PAP position M310 on activities of AM-rATP elongation of an RNA primer (FIG. 3A) and riboguanylation of a RNA primer (FIG. 3B) are examined. AM-rATP elongation of an RNA primer (FIG. 3A) was carried out in presence of 0.1 uM ATTO488-(rA)$_5$ primer, 0.5 uM PAP mutant, 250 uM AM-rATP in elongation AM-rATP buffer (20 mM Tris-HCl, 0.6 mM MnCl2, 0.02 mM EDTA, 0.1% BSA, 10% glycerol, 100 mM imidazole, pH 7-8) for 30 min. at 37 C in a total reaction volume of 20 uL. Riboguanylation of an RNA primer (FIG. 3B) was carried out in presence of 0.1 uM ATTO488-(rA)$_5$ primer, 0.5 uM PAP mutant, 250 uM AM-rATP in rGTP polymerization buffer (0.6 mM MnCl2, 0.1% BSA, 10 mM imidazole, pH 6.2) for 30 min. at 37 C in a total reaction volume of 20 uL.

Example 3

Effect of *Thielavia* PAP Variant on AM-rNTP Incorporation

*Thielavia* PAP (SEQ ID NO: 3) was engineered to have three substitutions (V240A, M318T and A410V) using conventional techniques, after which the modified polypeptide was expressed and purified. The ability of wild type *Thielavia* PAP and the mutated PAP to incorporate AM-NTPs was compared by performing the assay described in Example 2 except for the following conditions: 0.1 μM Atto488-(rA)$_7$, 3.0 μM PAP, 250 μM AM-NTP. The reaction results are given in Table 4 below.

TABLE 4

| PAP | Melting temp (degrees C.) | Purity + 1 product (%) AM-ATP | Purity + 1 product (%) AM-UTP | Purity + 1 product (%) AM-GTP | Purity + 1 product (%) AM-CTP |
|---|---|---|---|---|---|
| Thelavia variant | 46 | 100 | 100 | 97 | 95 |
| Thelavia wild type | 48 | 100 | 100 | 23 | 31 |

The data shows that the *Thielavia* PAP variant incorporates AM-rGTP and AM-rCTP monomers much more efficiently than the corresponding wild type PAP.

Example 4

Incorporation of AM-NTPs by PUP

Figure 4:
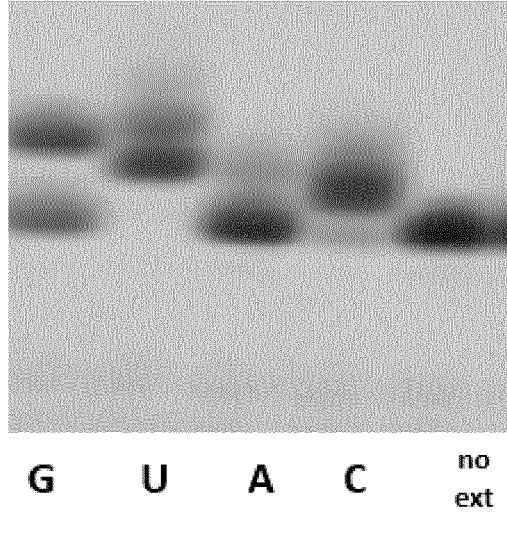
FIG. 4 is an electropherogram of incorporation products produced by *Schizosaccharomyces pombe* PUP. "No ext" means that the indicated column shows the band corresponding to the primer without any extension.

In this experiment, *Schizosaccharomyces pombe* PUP (SEQ ID NO: 4) was used to incorporate AM-NTPs into an initiator using the experimental protocol of Example 3. The extension products were separated by gel electrophoresis to give the electropherogram shown in FIG. 4.

Definitions

Amino acids are represented by either their one-letter or three-letters code according to the following nomenclature: A: alanine (Ala); C: cysteine (Cys); D: aspartic acid (Asp); E: glutamic acid (Glu); F: phenylalanine (Phe); G: glycine (Gly); H: histidine (His); I: isoleucine (Ile); K: lysine (Lys); L: leucine (Leu); M: methionine (Met); N: asparagine (Asn); P: proline (Pro); Q: glutamine (Gln); R: arginine (Arg); S: serine (Ser); T: threonine (Thr); V: valine (Val); W: tryptophan (Trp) and Y: tyrosine (Tyr).

"Functionally equivalent" in reference to a substituted residue means the substituted residue of a variant PAP has an identical functional role as a residue in a sequence of another PAP having a sequence homologous to SEQ ID NO: 1. Functionally equivalent residues may be identified by using sequence alignments, for example, using the Mutalin line alignment software (http://multalin.toulouse.inra.fr/multalin/multalin.html; 1988, Nucl. Acids Res., 16 (22), 25 10881-10890). After alignment, the functionally equivalent residues are at homologous positions on the different sequences considered. Sequence alignments and identification of functionally equivalent residues may be determined between any PAP and their natural variants, including inter-species.

"Isolated" in reference to protein means such a compound which has been identified and separated and/or recovered from a component of its natural environment or from a heterogeneous reaction mixture. Contaminant components of a natural environment or reaction mixture are materials which would interfere with a protein's function, and may include enzymes, hormones, and other proteinaceous or nonproteinaceous solutes. In some embodiments, a protein of the invention is purified (1) to greater than 95% by weight of protein as determined by the Lowry method, and most preferably more than 99% by weight, (2) to a degree sufficient to obtain at least 15 residues of N-terminal or internal amino acid sequence by use of a spinning cup sequenator, or (3) to homogeneity by SDS-PAGE under reducing or nonreducing conditions using Coomassie blue or, preferably, silver stain. When manufactured by recombinant methodologies, an isolated protein of the invention may include the protein of the invention in situ within recombinant cells since at least one component of the protein's natural environment will not be present. Ordinarily, an isolated protein of the invention is prepared by at least one purification step.

"Kit" refers to any delivery system for delivering materials or reagents for carrying out a method of the invention. In the context of reaction assays, such delivery systems include systems and/or compounds (such as dilutants, surfactants, carriers, or the like) that allow for the storage, transport, or delivery of reaction reagents (e.g., PAP enzymes, protected rNTP monomers, etc. in the appropriate containers) and/or supporting materials (e.g., buffers, written instructions for performing the assay etc.) from one location to another. For example, kits include one or more enclosures (e.g., boxes) containing the relevant reaction reagents and/or supporting materials. Such contents may be delivered to the intended recipient together or separately. For example, a first container may contain an enzyme, while a second or more containers contain rNTP monomers, buffers, solid supports with initiators, or the like.

"Mutant" or "variant," which are used interchangeably, refer to polypeptides derived from SEQ ID NO: 1 and comprising a modification or an alteration, i.e., a substitution, insertion, and/or deletion, at one or more positions and having both a template-free polymerase activity and ability to incorporate one or more reversibly blocked nucleoside triphosphate precursors. The variants may be obtained by various techniques well known in the art. In particular, examples of techniques for altering the DNA sequence encoding the wild-type protein, include, but are not limited to, site-directed mutagenesis, random mutagenesis and synthetic oligonucleotide construction. Mutagenesis activities consist in deleting, inserting or substituting one or several amino-acids in the sequence of a protein or in the case of the invention of a polymerase. The following terminology is used to designate a substitution: L238A denotes that amino acid residue (Leucine, L) at position 238 of a reference, or wild type, sequence is changed to an Alanine (A). A132V/I/M denotes that amino acid residue (Alanine, A) at position 132 of the parent sequence is substituted by one of the following amino acids: Valine (V), Isoleucine (I), or Methionine (M). The substitution can be a conservative or non-conservative substitution. Examples of conservative substitutions are within the groups of basic amino acids (arginine, lysine and histidine), acidic amino acids (glutamic acid and aspartic acid), polar amino acids (glutamine, asparagine and threonine), hydrophobic amino acids (methionine, leucine, isoleucine, cysteine and valine), aromatic amino acids (phenylalanine, tryptophan and tyrosine), and small amino acids (glycine, alanine and serine).

"Polynucleotide" or "oligonucleotide" are used interchangeably and each mean a linear polymer of nucleotide monomers or analogs thereof. Monomers making up polynucleotides and oligonucleotides are capable of specifically binding to a natural polynucleotide by way of a regular pattern of monomer-to-monomer interactions, such as Watson-Crick type of base pairing, base stacking, Hoogsteen or reverse Hoogsteen types of base pairing, or the like. Such monomers and their internucleosidic linkages may be naturally occurring or may be analogs thereof, e.g. naturally occurring or non-naturally occurring analogs. Non-naturally occurring analogs may include PNAs, phosphorothioate internucleosidic linkages, bases containing linking groups permitting the attachment of labels, such as fluorophores, or haptens, and the like. Whenever the use of an oligonucleotide or polynucleotide requires enzymatic processing, such as extension by a polymerase, ligation by a ligase, or the like, one of ordinary skill would understand that oligonucleotides or polynucleotides in those instances would not contain certain analogs of internucleosidic linkages, sugar moieties, or bases at any or some positions. Polynucleotides typically range in size from a few monomeric units, e.g. 5-40, when they are usually referred to as "oligonucleotides," to several thousand monomeric units. Whenever a polynucleotide or oligonucleotide is represented by a sequence of letters (upper or lower case), such as "ATGCCTG," it will be understood that the nucleotides are in 5'→3' order from left to right and that "A" denotes deoxyadenosine, "C" denotes deoxycytidine, "G" denotes deoxyguanosine, and "T" denotes thymidine, "I" denotes deoxyinosine, "U" denotes uridine, unless otherwise indicated or obvious from context. Corresponding ribonucleotides may be designated "rA", "rC", "rG", and "rT." Unless otherwise noted the terminology and atom numbering conventions will follow those disclosed in Strachan and Read, Human Molecular Genetics 2 (Wiley-Liss, New York, 1999). Usually polynucleotides comprise the four natural nucleosides (e.g. deoxyadenosine, deoxycytidine, deoxyguanosine, deoxythymidine for DNA or their ribose counterparts for RNA) linked by phosphodiester linkages; however, they may also comprise non-natural nucleotide analogs, e.g. including modified bases, sugars, or internucleosidic linkages. It is clear to those skilled in the art that where an enzyme has specific oligonucleotide or polynucleotide substrate requirements for activity, e.g. single stranded DNA, RNA/DNA duplex, or the like, then selection of appropriate composition for the oligonucleotide or polynucleotide substrates is well within the knowledge of one of ordinary skill, especially with guidance from treatises, such as Sambrook et al, Molecular Cloning, Second Edition (Cold Spring Harbor Laboratory, New York, 1989), and like references. Likewise, the oligonucleotide and polynucleotide may refer to either a single stranded form or a double stranded form (i.e. duplexes of an oligonucleotide or polynucleotide and its respective complement). It will be clear to one of ordinary skill which form or whether both forms are intended from the context of the terms usage.

"Primer" means an oligonucleotide, either natural or synthetic that is capable, upon forming a duplex with a polynucleotide template, of acting as a point of initiation of nucleic acid synthesis and being extended from its 3' end along the template so that an extended duplex is formed. Extension of a primer is usually carried out with a nucleic acid polymerase, such as a DNA or RNA polymerase. The sequence of nucleotides added in the extension process is determined by the sequence of the template polynucleotide. Usually primers are extended by a DNA polymerase. Primers usually have a length in the range of from 14 to 40 nucleotides, or in the range of from 18 to 36 nucleotides. Primers are employed in a variety of nucleic amplification reactions, for example, linear amplification reactions using a single primer, or polymerase chain reactions, employing two or more primers. Guidance for selecting the lengths and sequences of primers for particular applications is well known to those of ordinary skill in the art, as evidenced by the following references that are incorporated by reference: Dieffenbach, editor, PCR Primer: A Laboratory Manual, 2nd Edition (Cold Spring Harbor Press, New York, 2003).

"Sequence identity" refers to the number (or fraction, usually expressed as a percentage) of matches (e.g., identical amino acid residues) between two sequences, such as two polypeptide sequences or two polynucleotide sequences. The sequence identity is determined by comparing the sequences when aligned so as to maximize overlap and identity while minimizing sequence gaps. In particular, sequence identity may be determined using any of a number of mathematical global or local alignment algorithms, depending on the length of the two sequences. Sequences of similar lengths are preferably aligned using a global alignment algorithm (e.g. Needleman and Wunsch algorithm; Needleman and Wunsch, 1970) which aligns the sequences optimally over the entire length, while sequences of substantially different lengths are preferably aligned using a local alignment algorithm (e.g. Smith and Waterman algorithm (Smith and Waterman, 1981) or Altschul algorithm (Altschul et al., 1997; Altschul et al., 2005)). Alignment for purposes of determining percent amino acid sequence identity can be achieved in various ways that are within the skill in the art, for instance, using publicly available computer software available on internet web sites such as http://blast.ncbi.nlm.nih.gov/ or http://www.ebi.ac.uk/Tools/emboss/. Those skilled in the art can determine appropriate parameters for measuring alignment, including any algorithm needed to achieve maximal alignment over the full length of the sequences being compared. For purposes herein, % amino acid sequence identity values refer to values generated using the pair wise sequence alignment program EMBOSS Needle, that creates an optimal global alignment of two sequences using the Needleman-Wunsch algorithm, wherein all search parameters are set to default values, i.e. Scoring matrix=BLOSUM62, Gap open=10, Gap extend=0.5, End gap penalty=false, End gap open=10 and End gap extend=0.5.

"Substitution" means that an amino acid residue is replaced by another amino acid residue. Preferably, the term "substitution" refers to the replacement of an amino acid residue by another selected from the naturally-occurring standard 20 amino acid residues, rare naturally occurring amino acid residues (e.g. hydroxyproline, hydroxylysine, allohydroxylysine, 6-N-methylysine, N-ethylglycine, N-methylglycine, N-ethylasparagine, allo-isoleucine, N-methylisoleucine, N-methylvaline, pyroglutamine, aminobutyric acid, ornithine, norleucine, norvaline), and non-naturally occurring amino acid residue, often made synthetically, (e.g. cyclohexyl-alanine). Preferably, the term "substitution" refers to the replacement of an amino acid residue by another selected from the naturally-occurring standard 20 amino acid residues. The sign "+" indicates a combination of substitutions. The amino acids are herein represented by their one-letter or three-letters code according to the following nomenclature: A: alanine (Ala); C: cysteine (Cys); D: aspartic acid (Asp); E: glutamic acid (Glu); F: phenylalanine (Phe); G: glycine (Gly); H: histidine (His); I: isoleucine (Ile); K: lysine (Lys); L: leucine (Leu); M: methionine (Met); N: asparagine (Asn); P: proline (Pro); Q: glutamine (Gln); R: arginine (Arg); S: serine (Ser); T: threonine (Thr); V: valine (Val); W: tryptophan (Trp) and Y: tyrosine (Tyr). In the present document, the following terminology is used to designate a substitution: L238A denotes that amino acid residue (Leucine, L) at position 238 of the parent sequence is changed to an Alanine (A). A132V/I/M denotes that amino acid residue (Alanine, A) at position 132 of the parent sequence is substituted by one of the following amino acids: Valine (V), Isoleucine (I), or Methionine (M). The substitution can be a conservative or non-conservative substitution. Examples of conservative substitutions are within the groups of basic amino acids (arginine, lysine and histidine), acidic amino acids (glutamic acid and aspartic acid), polar amino acids (glutamine, asparagine and threonine), hydrophobic amino acids (methionine, leucine, isoleucine, cysteine and valine), aromatic amino acids (phenylalanine, tryptophan and tyrosine), and small amino acids (glycine, alanine and serine).

This disclosure is not intended to be limited to the scope of the particular forms set forth, but is intended to cover alternatives, modifications, and equivalents of the variations described herein. Further, the scope of the disclosure fully encompasses other variations that may become obvious to those skilled in the art in view of this disclosure. The scope of the present invention is limited only by the appended claims.

The invention claimed is:

1. A kit for performing template-free synthesis of a polyribonucleotide having a predetermined sequence, the kit comprising a poly (A) polymerase (PAP), an initiator attached to a solid support, and 3'-O-blocked ribonucleoside triphosphate monomers, wherein the PAP comprises a PAP variant having an amino acid sequence that is at least 90 percent identical to the amino acid sequence of SEQ ID NO: 3, wherein the PAP variant comprises a substitution of the methionine at position 318 and a substitution of the valine at position 240 with respect to SEQ ID NO: 3, and wherein the PAP variant is capable of (a) synthesizing a ribonucleic acid fragment without a template and (b) incorporating a 3'-O-azidomethyl-ribonucleoside triphosphate into a ribonucleic acid fragment or a 3'-O-azidomethyl-2'-deoxyribonucleoside triphosphate into a deoxyribonucleic acid fragment.

2. The kit of claim 1, wherein said 3'-O-protected ribonucleoside triphosphate monomers comprise one or more of 3'-O-azidomethyl-riboadenosine triphosphate, 3'-O-azidomethyl-riboguanosine triphosphate, 3'-O-azidomethyl-ribocytidine triphosphate, 3'-O-azidomethyl-ribothymidine triphosphate and 3'-O-amino-ribouridine triphosphate.

3. A poly (A) polymerase (PAP) variant comprising an amino acid sequence that is at least 90 percent identical to SEQ ID NO: 3 wherein the PAP variant comprises a substitution of the methionine at position 318 and a substitution of the valine at position 240 with respect to SEQ ID NO: 3, wherein the PAP variant is capable of (a) synthesizing a ribonucleic acid fragment without a template and (b) incorporating a 3'-O-azidomethyl-ribonucleoside triphosphate into a ribonucleic acid fragment or a 3'-O-azidomethyl-2'-deoxyribonucleoside triphosphate into a deoxyribonucleic acid fragment.

4. The PAP variant of claim 3, wherein said substitution of the methionine at position 318 is selected from F, Y, V, E or T.

5. The PAP variant of claim 3 wherein said substitution of the valine at position 240 is alanine or glycine.

6. The PAP variant of claim 3, wherein said substitution of the methionine at position 318 is T and said substitution of the valine at position 240 is A.

7. The PAP variant of claim 6, further comprising a substitution of the alanine at position 410 relative to SEQ ID NO: 3.

* * * * *

SEQUENCE LISTING

<160> NUMBER OF SEQ ID NOS: 47

<210> SEQ ID NO 1
<211> LENGTH: 552
<212> TYPE: PRT
<213> ORGANISM: Unknown
<220> FEATURE:
<223> OTHER INFORMATION: Yeast cell of the domain Eukaryota and the
      kingdom Fungi

<400> SEQUENCE: 1

```
Met Ala Ser Gln Lys Val Phe Gly Ile Thr Gly Pro Val Ser Thr Val
1               5                   10                  15

Gly Ala Thr Ala Ala Glu Asn Lys Leu Asn Asp Ser Leu Ile Gln Glu
                20                  25                  30

Leu Lys Lys Glu Gly Ser Phe Glu Thr Glu Gln Glu Thr Ala Asn Arg
            35                  40                  45

Val Gln Val Leu Lys Ile Leu Gln Glu Leu Ala Gln Arg Phe Val Tyr
        50                  55                  60

Glu Val Ser Lys Lys Lys Asn Met Ser Asp Gly Met Ala Arg Asp Ala
65                  70                  75                  80

Gly Gly Lys Ile Phe Thr Tyr Gly Ser Tyr Arg Leu Gly Val His Gly
                85                  90                  95

Pro Gly Ser Asp Ile Asp Thr Leu Val Val Val Pro Lys His Val Thr
                100                 105                 110

Arg Glu Asp Phe Phe Thr Val Phe Asp Ser Leu Leu Arg Glu Arg Lys
            115                 120                 125

Glu Leu Asp Glu Ile Ala Pro Val Pro Asp Ala Phe Val Pro Ile Ile
        130                 135                 140

Lys Ile Lys Phe Ser Gly Ile Ser Ile Asp Leu Ile Cys Ala Arg Leu
145                 150                 155                 160

Asp Gln Pro Gln Val Pro Leu Ser Leu Thr Leu Ser Asp Lys Asn Leu
                165                 170                 175

Leu Arg Asn Leu Asp Glu Lys Asp Leu Arg Ala Leu Asn Gly Thr Arg
            180                 185                 190

Val Thr Asp Glu Ile Leu Glu Leu Val Pro Lys Pro Asn Val Phe Arg
        195                 200                 205

Ile Ala Leu Arg Ala Ile Lys Leu Trp Ala Gln Arg Arg Ala Val Tyr
        210                 215                 220

Ala Asn Ile Phe Gly Phe Pro Gly Gly Val Ala Trp Ala Met Leu Val
225                 230                 235                 240

Ala Arg Ile Cys Gln Leu Tyr Pro Asn Ala Cys Ser Ala Val Ile Leu
            245                 250                 255

Asn Arg Phe Phe Ile Ile Leu Ser Glu Trp Asn Trp Pro Gln Pro Val
            260                 265                 270

Ile Leu Lys Pro Ile Glu Asp Gly Pro Leu Gln Val Arg Val Trp Asn
            275                 280                 285

Pro Lys Ile Tyr Ala Gln Asp Arg Ser His Arg Met Pro Val Ile Thr
        290                 295                 300

Pro Ala Tyr Pro Ser Met Cys Ala Thr His Asn Ile Thr Glu Ser Thr
305                 310                 315                 320

Lys Lys Val Ile Leu Gln Glu Phe Val Arg Gly Val Gln Ile Thr Asn
                325                 330                 335

Asp Ile Phe Ser Asn Lys Lys Ser Trp Ala Asn Leu Phe Glu Lys Asn
                340                 345                 350
```

-continued

```
Asp Phe Phe Phe Arg Tyr Lys Phe Tyr Leu Glu Ile Thr Ala Tyr Thr
        355                 360             365

Arg Gly Ser Asp Glu Gln His Leu Lys Trp Ser Gly Leu Val Glu Ser
    370                 375             380

Lys Val Arg Leu Leu Val Met Lys Leu Glu Val Leu Ala Gly Ile Lys
385                 390             395                 400

Ile Ala His Pro Phe Thr Lys Pro Phe Glu Ser Ser Tyr Cys Cys Pro
                405             410                 415

Thr Glu Asp Asp Tyr Glu Met Ile Gln Asp Lys Tyr Gly Ser His Lys
            420             425             430

Thr Glu Thr Ala Leu Asn Ala Leu Lys Leu Val Thr Asp Glu Asn Lys
        435             440             445

Glu Glu Glu Ser Ile Lys Asp Ala Pro Lys Ala Tyr Leu Ser Thr Met
    450             455             460

Tyr Ile Gly Leu Asp Phe Asn Ile Glu Asn Lys Lys Glu Lys Val Asp
465             470             475                 480

Ile His Ile Pro Cys Thr Glu Phe Val Asn Leu Cys Arg Ser Phe Asn
                485             490                 495

Glu Asp Tyr Gly Asp His Lys Val Phe Asn Leu Ala Leu Arg Phe Val
            500             505             510

Lys Gly Tyr Asp Leu Pro Asp Glu Val Phe Asp Glu Asn Glu Lys Arg
        515             520             525

Pro Ser Lys Lys Ser Lys Arg Lys Asn Leu Ser Ser Gly Glu Asn Leu
    530             535             540

Tyr Phe Gln Gly Ser Ser Gly Ser
545             550
```

```
<210> SEQ ID NO 2
<211> LENGTH: 674
<212> TYPE: PRT
<213> ORGANISM: Myceliophthora sp.

<400> SEQUENCE: 2
```

```
Met Ala Glu Arg Ile Tyr Gly Val Thr Pro Pro Ile Ser Thr Ala Leu
1               5               10              15

Pro Thr Glu Glu Glu Lys Arg Leu Asn Asn Ala Leu His Gln Glu Leu
            20              25              30

Arg Ala Gln Gly Thr Phe Glu Ser Pro Ala Glu Thr Glu Lys Arg Lys
        35              40              45

Glu Val Leu Arg Gln Leu Glu Lys Ile Thr Asn Val Phe Val Gln Arg
    50              55              60

Ala Ala Ala Glu Lys Glu Pro Lys Asn Thr Ile Leu Ile Arg Asp Ala
65              70              75              80

Ile Gly Arg Val Phe Thr Tyr Gly Ser Tyr Arg Leu Gly Val Tyr Gly
                85              90              95

Pro Gly Ser Asp Met Asp Thr Leu Val Val Ala Pro Lys Tyr Val Thr
            100             105             110

Val Glu Gln Tyr Phe Arg Ile Phe Pro Glu Val Leu Val Glu Met Ala
        115             120             125

Pro Pro Gly Ala Ile Thr Asp Leu Thr Pro Val Pro Glu Ala Phe Val
    130             135             140

Pro Ile Ile Lys Phe Glu Phe Ser Gly Ile Ser Ile Asp Leu Ile Phe
145             150             155             160

Cys Ser Ile Gln Thr Leu Lys Gln Leu Pro Ala Asp Lys Asn Trp Ser
                165             170             175
```

-continued

```
Leu Ala Asp Asn Asn Leu Leu Arg Gly Leu Ser Glu Asn Glu Val Arg
        180                     185                 190

Ser Leu Asn Gly Thr Arg Val Thr Asp Asp Ile Leu Asn Leu Val Pro
        195                 200                 205

Glu Pro Ala Thr Phe Lys Leu Ala Leu Arg Ala Ile Lys Leu Trp Ala
    210                 215                 220

Gln Arg Lys Ala Ile Tyr Ala Asn Ile Met Gly Tyr Pro Gly Gly Val
225                 230                 235                 240

Ala Trp Ala Met Leu Val Ala Arg Val Cys Gln Leu Tyr Pro Lys Ala
            245                 250                 255

Thr Ser Ala Val Ile Val Asn Lys Phe Phe His Ile Met Leu Lys Trp
            260                 265                 270

Pro Trp Pro Leu Pro Val Leu Leu Lys Asp Ile Glu Tyr Gly Cys Pro
        275                 280                 285

Val Thr Arg Val Ala Val Trp Asn Pro Lys Ile Tyr Ala Ser Asp Arg
        290                 295                 300

Asn His Arg Met Pro Ile Ile Thr Pro Ser Tyr Pro Ser Met Cys Ala
305                 310                 315                 320

Thr His Asn Val Gly Arg Ser Ser Met Ala Val Ile Lys Asp Glu Leu
            325                 330                 335

Glu Lys Gly Val Gln Val Thr Glu Asp Ile Met Arg Gly Lys Arg Pro
            340                 345                 350

Trp Lys Asp Leu Phe Thr Lys His Thr Phe Phe Thr Ser Gly Phe Arg
        355                 360                 365

Tyr Tyr Leu Thr Val Ile Ser Ser Ser Arg Thr Lys Lys Ala Gln Asn
    370                 375                 380

Val Trp Ser Gly Phe Val Glu Ser Arg Val Arg Leu Leu Val Asn Lys
385                 390                 395                 400

Leu Glu Met His Pro Ser Ile Ser Leu Ala Arg Pro Phe Asn Lys Gly
            405                 410                 415

Tyr Asp Arg Glu His Arg Cys Lys Asn Asn Ala Gln Leu Glu Glu Val
        420                 425                 430

Val Ser Leu Gly Ser Leu Ala Tyr Met Tyr Lys Pro Ala Thr Gly Glu
        435                 440                 445

Ala Lys Ala Glu Ala Lys Lys Glu Val Lys Thr Glu Val Lys His Glu
    450                 455                 460

Ser Gly Ala Ser Val Lys Asn Glu Ala Pro Glu Ala Lys Gly Glu Asp
465                 470                 475                 480

Gly Val Arg Ala Lys Arg Glu Asn Gly Asp Glu Ala Gln Leu Pro Pro
            485                 490                 495

Ala Thr Gly Ile Lys Pro Glu Pro Thr Asp Gly Ala Gly Ala Asp Val
        500                 505                 510

Lys Leu Glu Asp Ile Pro Val Lys Lys Asp Glu Pro Glu Glu Met Thr
        515                 520                 525

Ile Tyr Thr Thr Asn His Tyr Ile Gly Leu Gln Leu Val Glu Gly Ala
    530                 535                 540

Lys Thr Leu Asp Leu Ser Arg Glu Val Asn Asp Trp Lys Ala Met Cys
545                 550                 555                 560

Thr Ser Asn Glu Leu Tyr Glu Glu Gly Thr Met Phe Leu Ser Ile Gln
            565                 570                 575

His Val Arg Asn Thr Ala Leu Pro Asp Asp Val Phe Glu Pro Gly Glu
            580                 585                 590
```

```
Thr Arg Pro Arg Pro Ala Lys Lys Ser Leu Lys Arg Val Ala Ser Glu
        595             600             605

Asp Pro Gly Asn Lys Gln Thr Gln Pro Pro Ala Lys Lys Gln Val Gln
        610             615             620

Asp Lys Ala Pro Pro Ala Ala Gln Gln Gln Gln Gln Gln Gln His Gln
625             630             635             640

Gln Gln Gln Gln Pro Ala Ser Thr Ala Ala Ala Ala Gly Ser Ser
                645             650             655

Gly Glu Asn Leu Tyr Phe Gln Gly Ser Ser Gly Ser His His His His
        660             665             670

His His

<210> SEQ ID NO 3
<211> LENGTH: 672
<212> TYPE: PRT
<213> ORGANISM: Thielavia sp.

<400> SEQUENCE: 3

Met Ala Glu Arg Thr Tyr Gly Val Thr Pro Pro Ile Ser Thr Ala Leu
1               5               10              15

Pro Thr Glu Gln Glu Lys Ala Leu Asn Lys Ala Leu His Asp Glu Leu
        20              25              30

Arg Ala Gln Gly Thr Phe Glu Ser Arg Ala Glu Thr Glu Lys Arg Lys
        35              40              45

Glu Val Leu Ala Gln Leu Glu Lys Ile Thr Asn Ala Phe Val Gln Arg
    50              55              60

Ala Ala Arg Glu Lys His Gly Lys Asn Ala Ile Leu Ile Arg Asp Ala
65              70              75              80

Ile Gly Arg Val Phe Thr Tyr Gly Ser Tyr Arg Leu Gly Val Tyr Gly
                85              90              95

Pro Gly Ser Asp Met Asp Thr Leu Val Val Ala Pro Lys Tyr Val Thr
        100             105             110

Val Glu Gln Tyr Phe Arg Ile Phe Pro Glu Val Leu Val Glu Met Ala
        115             120             125

Pro Pro Ala Ala Ile Thr Asp Leu Thr Pro Val Pro Glu Ala Phe Val
        130             135             140

Pro Ile Ile Lys Phe Glu Phe Ser Gly Ile Ser Ile Asp Leu Ile Phe
145             150             155             160

Cys Ser Ile Gln Thr Leu Ile Gln Leu Pro Ala Asp Lys Ser Trp Ser
                165             170             175

Leu Ala Asp Asn Asn Leu Leu Arg Gly Leu Ser Glu Asn Ala Val Arg
        180             185             190

Ser Leu Asn Gly Thr Arg Val Thr Asp Glu Ile Leu His Leu Val Pro
        195             200             205

Glu Pro Ala Thr Phe Lys Leu Ala Leu Arg Ala Ile Lys Leu Trp Ala
        210             215             220

Gln Arg Lys Ala Ile Tyr Ala Asn Ile Met Gly Tyr Pro Gly Gly Val
225             230             235             240

Ala Trp Ala Met Leu Val Ala Arg Val Cys Gln Leu Tyr Pro Lys Ala
                245             250             255

Thr Ser Ala Val Ile Val Asn Lys Phe Phe Asn Ile Met Leu Lys Trp
        260             265             270

Pro Trp Pro Leu Pro Val Leu Leu Lys Asp Ile Glu Tyr Asn Gly Pro
        275             280             285
```

-continued

```
Val Thr Arg Val Pro Val Trp Asn Pro Lys Leu Tyr Ala Ser Asp Arg
    290             295             300

Asn His Lys Met Pro Ile Ile Thr Pro Ala Tyr Pro Ser Met Cys Ala
305             310             315             320

Thr His Asn Val Gly Arg Ser Ser Met Val Val Ile Gln Gln Glu Leu
            325             330             335

Lys Lys Gly Ala Glu Val Thr Glu Glu Ile Met Leu Gly Arg Arg Pro
            340             345             350

Trp Lys Asp Leu Phe Thr Lys His Thr Phe Phe Thr Ser Gly Phe Lys
            355             360             365

Tyr Tyr Leu Thr Val Ile Ser Ser Ser Arg Thr Lys Lys Ala Gln Asn
    370             375             380

Val Trp Ser Gly Phe Ile Glu Ser Arg Val Arg Leu Leu Val Asn Lys
385             390             395             400

Ile Glu Met His Pro Ser Ile Ala Leu Ala Arg Pro Phe Asn Lys Gly
                405             410             415

Tyr Asp Arg Met His Arg Cys Lys Asn Asp Ala Gln Val Glu Glu Val
            420             425             430

Val Ser Ala Gly Ser Leu Ala Tyr Val Tyr Thr Pro Pro Ala Phe Gly
            435             440             445

Asp Glu Lys Val Lys Ser Glu Thr Lys Ser Glu Val Lys Gln Glu Val
    450             455             460

Lys Gln Glu Val Arg Gln Asp Asp Val Ile Gln Asp Gly Val Pro Val
465             470             475             480

Lys Gln Glu Lys Ala Glu Val Arg Ala Glu Asp Gly Val Arg Ile Lys
            485             490             495

Arg Glu Leu Ser Glu Glu Val Gln Leu Pro Pro Pro Thr Asn Val Lys
            500             505             510

Pro Glu Pro His Asp Asp Glu Ala Lys Val Lys Leu Glu Asp Ile Pro
            515             520             525

Glu Lys Glu Ala Gln Pro Glu Asp Met Glu Ile Tyr Thr Thr Asn His
    530             535             540

Tyr Ile Gly Leu Gln Leu Val Glu Gly Ala Lys Ser Leu Asp Leu Ser
545             550             555             560

Arg Glu Val Asn Asp Trp Lys Ala Met Cys Met Ser Asn Glu Leu Tyr
            565             570             575

Glu Glu Gly Leu Met Phe Leu Ser Ile Gln His Leu Lys Asn Thr Ala
            580             585             590

Leu Pro Asp Asp Val Phe Glu Pro Gly Glu Val Lys Pro Arg Pro Gly
            595             600             605

Lys Lys Val Leu Lys Arg Gly Ala Ser Glu Glu Pro Ser Lys Gln Gln
            610             615             620

Pro Pro Ala Lys Arg Gln Ala His Val Gln Pro Arg Ala Pro Ala Ala
625             630             635             640

Gln Gln Pro Ser Ser Thr Ala Thr Ala Ala Ala Gly Ser Ser Gly Glu
            645             650             655

Asn Leu Tyr Phe Gln Gly Ser Ser Gly Ser His His His His His
            660             665             670
```

<210> SEQ ID NO 4
<211> LENGTH: 405
<212> TYPE: PRT
<213> ORGANISM: Schizosaccharomyces pombe -continued

```
<400> SEQUENCE: 4

Met Asn Ile Ser Ser Ala Gln Phe Ile Pro Gly Val His Thr Val Glu
1               5                   10                  15

Glu Ile Glu Ala Glu Ile His Lys Asn Leu His Ile Ser Lys Ser Cys
            20                  25                  30

Ser Tyr Gln Lys Val Pro Asn Ser His Lys Glu Phe Thr Lys Phe Cys
        35                  40                  45

Tyr Glu Val Tyr Asn Glu Ile Lys Ile Ser Asp Lys Glu Phe Lys Glu
    50                  55                  60

Lys Arg Ala Ala Leu Asp Thr Leu Arg Leu Cys Leu Lys Arg Ile Ser
65                  70                  75                  80

Pro Asp Ala Glu Leu Val Ala Phe Gly Ser Leu Glu Ser Gly Leu Ala
                85                  90                  95

Leu Lys Asn Ser Asp Met Asp Leu Cys Val Leu Met Asp Ser Arg Val
            100                 105                 110

Gln Ser Asp Thr Ile Ala Leu Gln Phe Tyr Glu Glu Leu Ile Ala Glu
        115                 120                 125

Gly Phe Glu Gly Lys Phe Leu Gln Arg Ala Arg Ile Pro Ile Ile Lys
    130                 135                 140

Leu Thr Ser Asp Thr Lys Asn Gly Phe Gly Ala Ser Phe Gln Cys Asp
145                 150                 155                 160

Ile Gly Phe Asn Asn Arg Leu Ala Ile His Asn Thr Leu Leu Leu Ser
            165                 170                 175

Ser Tyr Thr Lys Leu Asp Ala Arg Leu Lys Pro Met Val Leu Leu Val
            180                 185                 190

Lys His Trp Ala Lys Arg Lys Gln Ile Asn Ser Pro Tyr Phe Gly Thr
            195                 200                 205

Leu Ser Ser Tyr Gly Tyr Val Leu Met Val Leu Tyr Tyr Leu Ile His
    210                 215                 220

Val Ile Lys Pro Pro Val Phe Pro Asn Leu Leu Leu Ser Pro Leu Lys
225                 230                 235                 240

Gln Glu Lys Ile Val Asp Gly Phe Asp Val Gly Phe Asp Asp Lys Leu
            245                 250                 255

Glu Asp Ile Pro Pro Ser Gln Asn Tyr Ser Ser Leu Gly Ser Leu Leu
            260                 265                 270

His Gly Phe Phe Arg Phe Tyr Ala Tyr Lys Phe Glu Pro Arg Glu Lys
        275                 280                 285

Val Val Thr Phe Arg Arg Pro Asp Gly Tyr Leu Thr Lys Gln Glu Lys
    290                 295                 300

Gly Trp Thr Ser Ala Thr Glu His Thr Gly Ser Ala Asp Gln Ile Ile
305                 310                 315                 320

Lys Asp Arg Tyr Ile Leu Ala Ile Glu Asp Pro Phe Glu Ile Ser His
            325                 330                 335

Asn Val Gly Arg Thr Val Ser Ser Ser Gly Leu Tyr Arg Ile Arg Gly
            340                 345                 350

Glu Phe Met Ala Ala Ser Arg Leu Leu Asn Ser Arg Ser Tyr Pro Ile
        355                 360                 365

Pro Tyr Asp Ser Leu Phe Glu Glu Ala Pro Ile Pro Pro Arg Arg Gln
    370                 375                 380
```

-continued

```
Lys Lys Thr Asp Glu Gln Ser Asn Lys Lys Leu Leu Asn Glu Thr Asp
385                 390                 395                 400

Gly Asp Asn Ser Glu
                405

<210> SEQ ID NO 5
<211> LENGTH: 25
<212> TYPE: PRT
<213> ORGANISM: Artificial Sequence
<220> FEATURE:
<223> OTHER INFORMATION: His purification tag

<400> SEQUENCE: 5

Met Ala Ser Ser His His His His His His Ser Ser Gly Ser Glu Asn
1               5                   10                  15

Leu Tyr Phe Gln Thr Gly Ser Ser Gly
            20                  25

<210> SEQ ID NO 6
<211> LENGTH: 16
<212> TYPE: DNA
<213> ORGANISM: Artificial Sequence
<220> FEATURE:
<223> OTHER INFORMATION: Primer

<400> SEQUENCE: 6
tcatttcact ctcaca                                                       16

<210> SEQ ID NO 7
<211> LENGTH: 36
<212> TYPE: DNA
<213> ORGANISM: Artificial Sequence
<220> FEATURE:
<223> OTHER INFORMATION: primer

<400> SEQUENCE: 7
tgtgagagtg aaatgaggug ugagagugaa augagg                                 36

<210> SEQ ID NO 8
<211> LENGTH: 566
<212> TYPE: PRT
<213> ORGANISM: Pyronema omphalodes

<400> SEQUENCE: 8

Met Ser Ala Pro Pro Lys Gln Tyr Gly Thr Thr Pro Pro Ile Asn Thr
1               5                   10                  15

Asn Pro Pro Thr Lys Glu Asp Met Glu Arg Asn Ser Glu Leu Val Gln
            20                  25                  30

Glu Leu Lys Asn Gln Asn Cys Phe Glu Glu Lys Ala Glu Ser Asp Lys
        35                  40                  45

Arg Val Lys Val Leu Glu Ile Leu Gln Thr Leu Gly Glu Ala Phe Val
    50                  55                  60

Lys Lys Ala Cys Ala Ala Lys Gly Leu Pro Asp His Leu Val Asn Asn
65                  70                  75                  80

Ser Gly Gly Lys Ile Phe Thr Phe Gly Ser Tyr Arg Leu Gly Ala Tyr
                85                  90                  95

Gly Pro Gly Ser Asp Ile Asp Thr Leu Leu Val Val Pro Ala His Ile
            100                 105                 110

Glu Arg Ala Asp Phe Phe Gln His Val Pro Lys Met Leu Ser Glu Leu
        115                 120                 125
```

```
Asn Pro Pro Ala Glu Glu Val Ser Pro Val Pro Asp Ala Phe Val Pro
    130                 135             140

Ile Ile Lys Phe Glu Leu Gln Ser Ile Ser Ile Asp Leu Ile Phe Ala
145                 150             155                 160

Lys Val Pro Ser Val Asn Ser Ile Pro Arg Asp Met Thr Leu Glu Asn
                165             170             175

Lys Asp Ile Leu Lys Gly Cys Asp Glu Ala Asn Leu Arg Gly Leu Asn
            180             185             190

Gly Val Arg Leu Thr Asp Glu Leu Leu Gly Leu Val Pro His Pro Val
            195             200             205

Asn Phe Arg Met Ala Leu Arg Ala Ile Lys Leu Trp Ala Lys Ser Arg
    210             215             220

Ala Ile Tyr Ala Asn Val Met Gly Phe Pro Gly Gly Ile Ala Trp Ala
225             230             235             240

Met Leu Val Ala Lys Ile Cys Gln Leu Tyr Pro Met Ala Val Ser Ala
            245             250             255

Val Ile Val Cys Lys Phe Phe Thr Ile Tyr Thr Lys Trp Lys Trp Pro
            260             265             270

Gln Pro Val Leu Leu Lys Asp Ile Leu Asp Glu Gly Gly Gln Gly Ala
    275             280             285

Gly Leu Arg Val Trp Asn Pro Lys Ile Tyr Ala Ser Asp Arg Gly His
    290             295             300

Leu Met Pro Val Ile Thr Pro Asn Tyr Pro Cys Met Cys Ser Thr His
305             310             315             320

Asn Ile Thr Lys Ser Thr Lys Ala Val Ile Leu Arg Glu Met Asp Arg
            325             330             335

Ser Leu Asn Ile Ile His Glu Ile Met Asp Gly Lys Ser Pro Trp Ser
            340             345             350

Lys Leu Phe Ala Pro His Thr Phe Phe Thr Gln Asp Tyr Arg Tyr Tyr
            355             360             365

Leu Arg Val Ile Ser Ala Ala Arg Thr Lys Asp Glu Gln Leu Leu Trp
    370             375             380

Ser Gly Leu Val Glu Ser Lys Leu Arg His Leu Val Ser Lys Leu Glu
385             390             395             400

Met Leu Asp Asn Ile Gln Leu Ala His Pro Phe Asn Lys Gly Phe Glu
            405             410             415

Tyr Glu Val Glu Cys Asn Asn Glu Asp Glu Val Met Arg Val Ile Arg
            420             425             430

Gly Glu Asn Ile Asp Gln Ser Glu Ala Asn Gly Thr Ala Val Asp Ser
            435             440             445

Asn Gly Lys Ser Ser Lys Val Lys Ala Tyr Thr Thr Ser Phe Tyr Val
    450             455             460

Gly Leu Val Leu Asp Thr Ser Lys Ser Lys Gln Phe Asp Ile Ser Trp
465             470             475             480

Ala Cys His Glu Phe Tyr Asp Ile Cys Lys Thr Trp Asn Leu Tyr Asn
            485             490             495

Asp Asp Met His Ser Ile His Val Val Asn Thr Arg Asn Phe Glu Leu
            500             505             510

Pro Asp Asn Val Phe Lys Pro Gly Glu Thr Lys Pro Thr Lys Lys Thr
            515             520             525

Lys Thr Ile Lys Arg Lys Ile Pro Asn Ala Ala Gly Lys Lys Arg Gly
    530             535             540
```

-continued

```
Ala Asp Glu Ile Ser Ala Pro Asp Ser Lys Arg Ala His Ile Asn Glu
545                 550                 555                 560

Val Pro Pro Asn Ala Asn
                565

<210> SEQ ID NO 9
<211> LENGTH: 598
<212> TYPE: PRT
<213> ORGANISM: Tilletia indica

<400> SEQUENCE: 9

Met Thr Lys His Leu Gly Val Thr Pro Ile Val Ser Asp Ala Ser Pro
1               5                   10                  15

Thr Ala His Glu Ile Ala Leu Glu Thr Gln Leu Val Thr Glu Leu Thr
                20                  25                  30

Thr Gln Asn Cys Phe Glu Ser Pro Gln Asp Ser Arg Leu Arg Glu Val
            35                  40                  45

Val Leu Gly Lys Ala Asp Lys Leu Val Lys Glu Phe Val Tyr Arg Ala
        50                  55                  60

Ala Ile Ala Arg Gly Leu Pro Glu Ser Ala Ala Arg Glu Leu Gly Gly
65                  70                  75                  80

Lys Ile Phe Thr Phe Gly Ser Tyr Arg Leu Gly Val His Gly Pro Gly
                85                  90                  95

Ser Asp Ile Asp Thr Leu Cys Val Val Pro Lys His Val Gln Arg Glu
                100                 105                 110

Asp Phe Phe Thr Ile Phe Glu Gln Met Leu Arg Gln Arg Glu Asp Val
            115                 120                 125

Thr Asp Val Ala Pro Val Pro Glu Ala Tyr Val Pro Leu Ile Ala Val
        130                 135                 140

Asn Phe Met Gly Ile Ala Ile Asp Phe Leu Phe Ala Arg Leu Ser Leu
145                 150                 155                 160

Ser Arg Ile Asp Asp Ser Leu Asp Leu Ser Asp Asn Thr Ile Leu Lys
                165                 170                 175

Asn Met Asp Asp Gln Asp Ile Arg Ser Val Gly Gly Ser Arg Val Thr
            180                 185                 190

Asp Glu Ile Leu Arg Leu Val Pro Asn Val Glu Thr Phe His Thr Ala
        195                 200                 205

Leu Arg Ala Ile Lys Leu Trp Ala Gln Arg Arg Ala Ile Tyr Lys Asn
        210                 215                 220

Met Val Gly Phe Pro Gly Gly Val Ala Trp Ala Met Leu Val Ala Arg
225                 230                 235                 240

Ile Cys Gln Leu Tyr Pro Asn Gly Asn Ala Ala Val Ile Ile Glu Arg
                245                 250                 255

Phe Phe Ile Ile Met Phe Gln Trp Asn Trp Pro Gln Pro Val Met Leu
            260                 265                 270

Lys His His Ile Tyr Glu Ala Asp Pro Ile Leu Lys Val Trp Asn Pro
        275                 280                 285

Arg Leu Tyr Ala Ala Asp Arg Ser His Arg Met Pro Ile Ile Thr Pro
        290                 295                 300

Ala Tyr Pro Gly Met Cys Ala Thr His Asn Ile Thr Ala Ser Thr Gln
305                 310                 315                 320

Ala Val Leu Thr Leu Glu Phe Lys Arg Gly Ile Glu Ile Met Ser Ala
                325                 330                 335
```

-continued

```
Met Ser Ala Ser Ile Thr Asn Pro Ala Leu Pro Gln Thr Thr Trp Ala
            340             345             350

Thr Leu Phe Glu Ser Arg Arg Phe Phe Glu Glu Tyr Lys Tyr Tyr Leu
            355             360             365

Gln Ile Ile Ala Ser Ser Gly Ser Ala Asp Leu Gln Leu Lys Trp Ala
            370             375             380

Gly Thr Val Glu Ser Lys Leu Arg His Leu Val Leu Ser Thr Glu Ala
385             390             395             400

Gln Pro Gly Val Lys Ile Ala His Pro Tyr Thr Arg Glu Ile Asp Leu
            405             410             415

Val Ser Glu Cys His Thr Asp Glu Glu Val Arg Arg Val Ala Thr Gly
            420             425             430

Asp Val Pro Pro Glu Val Ala Ala Arg Ala Arg Thr Val Glu Gly Glu
            435             440             445

Gly Val Leu Pro Glu Ser Lys Glu Val Asp Lys Leu Lys Glu Ile Glu
            450             455             460

Ser Lys Glu Glu Glu Ala Arg Lys Lys Gly Arg Arg Thr Ile Trp Thr
465             470             475             480

Thr Thr Phe Tyr Ile Gly Leu Ala Leu His Asp Gly Ser Asp Asp Lys
            485             490             495

Thr Gly Gln Ser Ala Pro Lys Arg Leu Asp Leu Val Gly Pro Ile Gln
            500             505             510

Asp Phe Lys Gly Arg Cys Thr Glu Trp Ala Thr Tyr Asp Glu Ser Thr
            515             520             525

Met Gly Val Val Val Arg His Val Lys Arg Ser Gln Leu Pro Asp Ser
            530             535             540

Val Phe Pro Asp Gly Lys Arg Pro Ala Ala Pro Val Lys Lys Val Val
545             550             555             560

Lys Lys Arg Lys Arg Asn Ala Gly Met Ala Glu Ala Ala Ala Glu Thr
            565             570             575

Lys Glu Glu Glu Gly Ala Asp Glu Gln Glu Ala Lys Arg Ala Arg Thr
            580             585             590

Asn Gly Asp Ser Ala Ala
            595
```

```
<210> SEQ ID NO 10
<211> LENGTH: 574
<212> TYPE: PRT
<213> ORGANISM: Clathrospora elynae

<400> SEQUENCE: 10

Met Asn Gly Pro Pro Lys Thr Gln Tyr Gly Val Thr Ser Ala Ile Ser
1               5               10              15

Glu Ala Ala Pro Thr Glu Glu Asp Arg Leu Leu Asn Asp Lys Leu Ile
            20              25              30

Glu Thr Leu Lys Arg Glu Asn Val Phe Glu Thr Pro Glu Gly Asn Ala
            35              40              45

Lys Arg Glu Glu Val Ile Leu His Leu Gln Lys Val Val Glu Glu Phe
            50              55              60

Val Arg Arg Val Gly Lys Gln Lys Gly Val Pro Gln Ser Thr Ile Asp
65              70              75              80

Ala Ala Gly Gly Lys Val Phe Thr Phe Gly Ser Tyr Ala Leu Gly Val
            85              90              95
```

-continued

```
His Gly Pro Ser Ser Asp Ile Asp Thr Leu Val Val Ala Pro Lys Phe
            100             105             110

Val Thr Ile Asp Glu Phe Phe Gln Thr Phe Pro Pro Thr Phe Lys Glu
            115             120             125

Met Ser Arg Val Glu Asp Ile Lys Glu Phe Val Pro Val Glu Asp Ala
        130             135             140

Phe Val Pro Ile Ile Lys Met Glu Tyr Arg Gly Val Ser Ile Asp Leu
145             150             155             160

Leu Phe Ala Ser Leu Pro Arg Met Ala Ser Ile Pro Lys Asp Met Asp
            165             170             175

Thr Ile Asp Lys Lys Asn Leu Glu Gly Leu Gly Glu Ser Ala Thr Arg
        180             185             190

Ser Val Asn Gly Thr Arg Val Thr Lys Glu Leu Leu Ala Ala Val Pro
        195             200             205

Gln Asn Asn Ser Phe Arg His Ala Leu Arg Ala Ile Lys Leu Trp Ser
        210             215             220

Ser Arg Arg Gly Ile Tyr Gly Ala Val Phe Gly Tyr Pro Gly Gly Val
225             230             235             240

Ala Trp Ala Ile Met Val Ala Arg Ile Cys Gln Leu Tyr Pro Phe Ala
            245             250             255

Asn Gly Ala Thr Ile Val Ser Lys Phe Phe Ser Leu Met Tyr Lys Trp
            260             265             270

Thr Trp Pro Arg Pro Val Met Leu Lys His Ile Glu Glu Gly Ala Met
        275             280             285

Gly Leu Arg Val Trp Asn Pro Gln Ile Tyr Gly Gly Asp Arg Ala His
        290             295             300

Leu Met Pro Ile Ile Thr Pro Ala Phe Pro Ser Met Cys Ala Thr His
305             310             315             320

Thr Val Met Pro Ser Thr Leu Arg Ile Met Lys Glu Glu Phe Gly Arg
            325             330             335

Ala Asp Lys Ile Leu Gln His Val Phe Ala Gly Thr Lys Lys Trp Asp
            340             345             350

Ala Leu Phe Glu Arg His Ser Phe Phe Thr Lys Asp His Lys Tyr Tyr
        355             360             365

Leu Ser Val Val Ala Ala Ser Arg Thr Lys Glu Ala Asn Ser Thr Phe
        370             375             380

Ser Gly Leu Val Gln Ser Lys Ile Arg His Ile Val Lys Gly Ile Asp
385             390             395             400

Asp Gly Gln Thr Gly Val Asp Ile Ala Arg Pro Tyr Ile Asp Tyr Phe
            405             410             415

Glu Arg Tyr His Arg Cys Lys Asp Glu Asp Gln Ile Phe Gln Val Cys
            420             425             430

Gln Gly Lys Leu Asp His Met Ile Pro Ala Ser Glu Leu Pro Ala Glu
        435             440             445

Gly Thr Ala Pro Ala Asn Gly Asp Ser His Ile Met Tyr Thr Thr Thr
        450             455             460

Phe Tyr Ile Gly Leu Thr Leu Pro Leu Gly Thr Ala Thr Glu Gly Thr
465             470             475             480

Lys Ser Leu Asp Ile Ser Tyr Pro Val Ser Gln Phe Lys Asn Phe Ile
            485             490             495

Thr Asp Ala Asp Lys Phe Asp Lys Glu Thr Met Ser Val Lys Val Val
            500             505             510
```

-continued

```
His Thr Arg Ser Ser Ala Leu Pro Asp Asp Val Phe Val Gln Gly Glu
        515             520             525

Thr Arg Pro Lys Lys Pro Val Lys Glu Lys Lys Lys Lys Glu Ala Lys
        530             535             540

Ser Ala Lys Arg Gln Phe Ala Asp Thr Gly Leu Asp Val Arg Asp Ser
545             550             555             560

Arg Leu Thr Lys Pro Ser Gln Arg Ser Ser Ala Ser Arg Glu
                565             570

<210> SEQ ID NO 11
<211> LENGTH: 546
<212> TYPE: PRT
<213> ORGANISM: Drechslerella brochopaga

<400> SEQUENCE: 11

Met Pro Ala Ser Val Asp Val Leu Lys Arg Leu Gln Lys Ile Thr Glu
1               5               10              15

Glu Phe Val Arg Gln Val Tyr Thr Ser Lys Asn Gln Asn Glu Leu Thr
        20              25              30

Thr Asn Ser Ala Gly Gly Lys Val Phe Thr Tyr Gly Ser Tyr Arg Leu
        35              40              45

Gly Val Val Gly Pro Gly Ser Asp Ile Asp Thr Leu Val Val Ala Pro
    50              55              60

Lys Leu Val Thr Arg Glu Asp Phe Phe Lys Phe Tyr Pro Pro Leu Leu
65              70              75              80

Lys Ala Leu Asn Lys Ala Asn Glu Pro Pro Val Ile Glu Glu Leu Ala
                85              90              95

Pro Val Pro Asp Ala Phe Val Pro Ile Ile Lys Phe Val Met Ser Gly
        100             105             110

Ile Ser Ile Asp Leu Ile Phe Cys Arg Leu Gly Val Ala Gln Val Pro
        115             120             125

Ala Asp Met Thr Leu Glu Asp Lys Asn Leu Leu Arg Gly Leu Asp Glu
    130             135             140

Lys Glu Leu Arg Ser Leu Asn Gly Thr Arg Val Thr Asp Glu Ile Leu
145             150             155             160

Thr Leu Val Pro Val Pro Ala Val Phe Lys His Ala Leu Arg Ala Ile
                165             170             175

Lys Ile Trp Ala Lys Cys Arg Ala Ile Tyr Gly Asn Val Tyr Gly Phe
        180             185             190

Pro Gly Gly Val Ala Trp Ala Met Leu Val Ala Arg Ile Cys Gln Leu
        195             200             205

Tyr Pro Ser Ala Val Ser Ala Val Ile Val Ser Lys Phe Phe Arg Ile
        210             215             220

Leu Gly Gln Trp Asn Trp Pro Gln Pro Val Leu Leu Lys Pro Ile Glu
225             230             235             240

Asp Gly Pro Leu Asn Val Arg Val Trp Asn Pro Lys Leu Tyr Pro Ser
                245             250             255

Asp Arg Asn His Leu Met Pro Ile Ile Thr Pro Ala Tyr Pro Ser Met
                260             265             270

Cys Ser Thr His Asn Ile Thr Pro Ser Thr Lys Ala Val Ile Leu Gly
        275             280             285

Glu Met Ala Lys Ala Ala Asp Ile Val Asp Arg Ile Ile Thr Gly Asn
        290             295             300

Gly Asn Trp Asn Gln Leu Phe Gln Arg His Thr Phe Phe Thr Lys Asp
305             310             315             320
```

-continued

```
Tyr Lys Tyr Tyr Leu Thr Val Lys Ala Ser Ala Arg Asp Gln Glu Gln
        325                 330                 335

Ser Val Lys Trp Ser Gly Leu Val Glu Ser Lys Ile Arg His Leu Val
        340                 345                 350

Met Lys Leu Glu Met Leu Ser Asp Val Ile Ala Ser Ala Arg Pro Tyr
        355                 360                 365

Val Lys Pro Phe Glu Lys Val Gln Tyr Cys Arg Asn Gln Glu Glu Ala
    370                 375                 380

His Lys Ile Ala Met Gly Gln His Val Pro Asp Ser Pro Pro Ala Glu
385                 390                 395                 400

Ala Ala Asn Ala Ala Thr Gly Glu Thr Ala Gly Glu Val Ser Glu Gln
                405                 410                 415

Glu Lys Glu Gly Gly Val Pro Val Trp Ile Thr Thr Phe His Ile Gly
            420                 425                 430

Ile Glu Leu Thr Pro Gly Met Val Gly Gln Val Asn Ile Ser Trp Pro
        435                 440                 445

Ala Gln Glu Phe Tyr Ile Met Cys His Asn Trp Glu Gly Tyr Glu Glu
    450                 455                 460

Asn Met His Cys Val Lys Leu Glu Leu Leu Arg Asn Trp Asn Leu Pro
465                 470                 475                 480

Asp Glu Cys Phe Asp Phe Ser Lys Gly Asp Ala Lys Pro Ser Arg Pro
                485                 490                 495

Ile Val Lys Arg Lys Val Ile Arg Lys Val Val Ser Ser Ser Glu Val
            500                 505                 510

Ser Gln Ser Gly Met Lys Arg Thr His Ala Glu Glu Asn Pro Asn Ala
        515                 520                 525

Asp Glu Gly Asp Val Lys Arg Thr Lys Val Asn Ala Pro Val Thr Val
    530                 535                 540

Gln Gly
545

<210> SEQ ID NO 12
<211> LENGTH: 632
<212> TYPE: PRT
<213> ORGANISM: Magnaporthiopsis poae

<400> SEQUENCE: 12

Met Ala Glu Arg Gln Leu Gly Val Thr Pro Pro Val Ser Val Ser Leu
1               5                   10                  15

Pro Ser Glu Phe Glu Leu Gln Ala Thr Asp Ala Leu Leu Ala Glu Leu
                20                  25                  30

Arg Ala Gln Asn Ser Phe Glu Ser Pro Leu Glu Thr Gln Lys Arg His
        35                  40                  45

Arg Val Leu Ala Ser Leu Gln Thr Ile Ala Asp Ala Phe Val Lys Val
        50                  55                  60

Val Ala Gln Glu Arg Glu Pro His Asn Ala Val Leu Ile Lys Asp Ala
65                  70                  75                  80

Arg Ala Lys Val Phe Ala Tyr Gly Ser Leu Arg Leu Gly Val Trp Gly
                85                  90                  95

Pro Gly Ser Asp Ile Asp Thr Leu Val Val Gly Pro Arg Tyr Val Thr
            100                 105                 110

Arg Glu Asp Tyr Phe Lys His Phe Pro Asp Leu Leu Val Lys Met Ala
        115                 120                 125
```

-continued

```
Pro Pro Gly Ala Ile Thr Asp Leu Ala Val Val Gln Glu Ala Phe Val
    130             135             140

Pro Ile Ile Lys Phe Glu Tyr His Gly Ile Ser Ile Asp Leu Ile Phe
145             150             155             160

Ser Arg Ile Ala Thr Leu Lys Gln Leu Pro Ser Asp Pro Ala Trp Asp
                165             170             175

Leu Lys Asp Asn Asn Leu Leu Arg Gly Leu Asp Glu Lys Glu Leu Arg
            180             185             190

Ser Val Asn Gly Thr Arg Val Thr Asp Glu Ile Leu Ser Leu Val Pro
            195             200             205

Glu Gln Asn Ile Phe Arg Thr Ala Leu Arg Ala Ile Lys Leu Trp Ala
    210             215             220

Gln Arg Arg Ala Val Tyr Gly Asn Ile Met Gly Phe Pro Gly Gly Val
225             230             235             240

Ala Trp Ala Met Leu Val Ala Arg Val Cys Gln Leu Tyr Pro Lys Ala
                245             250             255

Thr Ser Ser Val Ile Val Asn Lys Phe Tyr Ser Ile Leu Leu Gln Trp
            260             265             270

Pro Trp Pro Gln Pro Val Leu Leu Lys Pro Ile Gly Asp Gly Pro Leu
        275             280             285

Gln Val Arg Val Trp Asn Pro Arg Leu Tyr Lys Gly Asp Ser Tyr His
    290             295             300

Leu Met Pro Val Ile Thr Pro Ala Tyr Pro Ser Met Cys Ala Thr Phe
305             310             315             320

Asn Val Thr Arg Ser Ser Met Thr Val Ile Tyr Arg Glu Leu Gln Leu
            325             330             335

Ala Ala Glu Val Thr Asn Asn Ile Met Cys Ser Thr Lys Pro Trp Lys
            340             345             350

Asp Leu Phe Thr Lys His Thr Phe Phe Thr Lys Asp Phe Lys Tyr Tyr
        355             360             365

Met Gln Val Ile Ser Ala Ser Arg Asp Lys Glu Ala His Lys Ile Trp
    370             375             380

Ser Gly Phe Val Glu Ser Lys Val Arg Met Leu Val Gln Ser Leu Glu
385             390             395             400

Arg His Asp Ser Ile Ala Val Ala Arg Pro Phe Ile Lys Gly Phe Glu
            405             410             415

Arg Phe His Arg Tyr Arg Asn Glu Glu Gln Phe Ala Gln Ile Leu Asp
            420             425             430

Gly Asn Leu Gln His Met Val Lys Ala Gly Gly Asp Ala Ser Pro Ser
    435             440             445

Gln Asp Gly Ile Gln Ala Lys Lys Glu Asp Asn Ser Ser Val Lys Ala
    450             455             460

Glu Glu Asp Ala Lys Val Lys Gln Glu Asn Gly Glu Thr Pro Val Lys
465             470             475             480

Gln Glu Asn Gly Val Lys Val Lys Gly Glu Glu Ser Glu Glu Ala Pro
            485             490             495

Leu Ala Ser Ile Pro Glu His Ser Pro Val Asp Thr Lys Gly Asp Ser
            500             505             510

Lys Ala Gly Asp Glu Ala Leu Glu Met Tyr Thr Thr Thr His Tyr Ile
    515             520             525

Gly Leu Glu Leu Asn Pro Ala Ala Lys Ser Leu Asp Leu Ser Phe Gln
    530             535             540
```

-continued

```
Val Asn Asp Phe Arg Ala Leu Cys His Asn Trp Glu Lys Tyr Lys Asp
545                 550                 555                 560

Glu Leu Ser Asp Arg Cys Tyr Val Asn Ile Lys Asp Leu Arg Asn Phe
                565                 570                 575

Ala Leu Pro Glu Asp Leu Phe Glu Pro Gly Glu Val Lys Pro Val Lys
            580                 585                 590

Ser Val Lys Lys Arg Pro Ala Ala Gly Ala Asn Ala Thr Gly Asp Lys
        595                 600                 605

Lys Arg Pro Ala Asn Glu Asp Asn Ser Asn Pro Ala Lys Arg Arg Gln
    610                 615                 620

Ala Ala Ser Val Ala Ala Ala Gly
625                 630

<210> SEQ ID NO 13
<211> LENGTH: 631
<212> TYPE: PRT
<213> ORGANISM: Cryptococcus depauperatus

<400> SEQUENCE: 13

Met Leu Gly Val Thr Pro Pro Ile Ser Ile Glu Ala Pro Lys Pro Gly
1               5                   10                  15

Asp Ile His Ser Ser Glu Ala Leu Met Thr Asp Leu Ile Ala Met Asn
                20                  25                  30

Gln Phe Glu Ser Asp Ser Glu Arg Lys Ile Arg Glu Lys Leu Leu Ser
            35                  40                  45

Asn Ile Ala Gln Leu Val Val Lys Phe Val His Asp Val Ser Leu Lys
        50                  55                  60

Ile Gly Met Ser Glu Lys Met Ala Ser Glu Ser Gly Gly Arg Ile Tyr
65                  70                  75                  80

Thr Ser Gly Ser Tyr Arg Leu Gly Val His Gly Pro Gly Ser Asp Ile
                85                  90                  95

Asp Thr Ile Cys Val Cys Pro Arg His Ile Tyr Arg Glu His Phe Phe
                100                 105                 110

Gly Glu Phe Gln Glu Met Leu Arg Ala Trp Pro Glu Val Thr Glu Ile
            115                 120                 125

Thr Ala Val Thr Gly Ala Phe Val Pro Val Met Lys Thr Val Ile Ser
        130                 135                 140

Gly Val Glu Val Asp Leu Leu Phe Ala Arg Val Asn Leu Pro Glu Ala
145                 150                 155                 160

Gly Asp Ser Leu Asp Ile Glu Lys Asp Glu Ile Leu Arg Gly Val Asp
                165                 170                 175

Asp Ala Ser Gln Arg Ser Leu Asn Gly Pro Arg Val Thr Asp Met Ile
            180                 185                 190

Leu Asn Leu Val Pro Asp Val Thr Thr Phe Arg Thr Ala Leu Arg Ser
        195                 200                 205

Ile Arg Leu Trp Ala Arg Arg Arg Gly Ile Tyr Ser Asn Val Leu Gly
    210                 215                 220

Phe Pro Gly Gly Val Ala Trp Ala Leu Leu Thr Ala Arg Ile Cys Gln
225                 230                 235                 240

Leu Tyr Pro Asn Ala Thr Pro Ser Ile Ile Val Gly Lys Phe Phe Pro
                245                 250                 255

Ile Tyr Tyr Gln Trp Asn Trp Pro Gln Pro Val Ile Leu Lys Lys Ile
            260                 265                 270

Glu Asn Gly Pro Pro Asn Met Gln His Ala Val Trp Asn Pro Lys Leu
        275                 280                 285
```

```
Asp Arg Arg Asp Met Ala His Arg Met Pro Val Ile Thr Pro Ala Tyr
    290             295             300

Pro Ser Met Cys Ser Thr His Asn Ile Thr Ala Ser Thr Met Ser Ile
305             310             315             320

Ile Ser Lys Glu Met Leu Arg Ala Met Gln Ile Thr Asp Asp Ile Leu
            325             330             335

Arg Glu Pro Gly Ala Ser Trp Ala Pro Leu Phe Glu Lys Val Asp Phe
            340             345             350

Phe Ser Met Tyr Lys Thr Tyr Val Gln Val Val Ala Ser Ala Ser Thr
            355             360             365

Ala Glu Gly Ile Lys Asp Trp Ser Gly Thr Val Glu Ala Arg Ile Arg
    370             375             380

Thr Leu Val Gln Asp Leu Glu Asn Thr Asp Ser Ile Leu Thr Ala His
385             390             395             400

Pro Leu Val Gly Gly Val Ser Arg Val Phe Tyr Cys Thr Thr Glu Glu
            405             410             415

Glu Gln Ala Ala Ala Ser Gln Gly Glu Leu Thr Ser Glu Met Ile Asp
            420             425             430

Arg Thr Glu Glu Glu Val Thr Asp Lys Glu His Arg Asn Ile Phe Thr
            435             440             445

Lys Ser Phe Phe Ile Gly Leu Glu Ile Glu Lys Lys Thr Lys Glu Gly
    450             455             460

Gly Gly Arg Val Leu Asn Leu Phe Tyr Pro Ser Lys Lys Phe Cys Ser
465             470             475             480

Met Cys Gln Ser Trp Asp Arg Tyr Asn Glu Met Glu Met Ser Val Ile
            485             490             495

Leu Arg Pro Ala Lys Arg Ser Asp Leu Pro Ser Phe Val Phe Pro Asp
            500             505             510

Gly Ile Pro Ile Ser Lys Lys Lys Ala Lys Arg Gln Gln Gln Asn Gly
            515             520             525

Ser Ala Asp Ala Ser Leu Ser Asp Ser Val Glu Gly Gln Gly Pro Ser
    530             535             540

Lys Arg Thr Lys Ala Ala Pro Pro Ser Pro Asn Gln Ala Ser Asn Pro
545             550             555             560

Arg Cys Asn Gly Leu Pro Val Gln Asn Gly Ser Asp Pro Val Ser Ser
            565             570             575

Lys Ile Gly Glu Glu Val Asp Ile Lys Pro Pro Pro Gly Ile Glu Asn
            580             585             590

Leu Pro Pro Leu Ser Asn Ala Ala Met Ser Ser Phe Ala Thr Ala Ala
            595             600             605

Lys Gly Val Ala Thr Thr Gln Asp Phe Asn Lys Glu Gly Leu Val Val
    610             615             620

Leu Asn Gln Gln Ser Thr Leu
625             630
```

<210> SEQ ID NO 14
<211> LENGTH: 571
<212> TYPE: PRT
<213> ORGANISM: Golovinomyces cichoracearum

<400> SEQUENCE: 14

```
Met Ala Glu Lys Ser Phe Gly Val Thr Ala Pro Leu Ser Val Thr Pro
1               5               10              15
```

-continued

```
Pro Thr Glu Ser Glu Asn Gln Ala Ser Ser Ala Leu Ile Glu Glu Leu
        20              25              30

Lys Arg Gln Asn Asn Tyr Glu Asn Ala Ile Glu Thr Ala Asn Arg Gln
        35              40              45

Lys Val Leu Asn Ser Leu Gln Leu Ile Thr Glu Glu Phe Val Arg Gln
        50              55              60

Val Ser Arg Ala Gln Gly Leu Pro Ala Asn Leu Ile Lys Ser Ala Gly
65              70              75              80

Gly Met Val Val Thr Phe Gly Ser Tyr Lys Leu Gly Val Ile Gly Pro
                85              90              95

Gly Ser Asp Ile Asp Thr Leu Ile Val Ala Pro Gln Asn Val Thr Lys
            100             105             110

Glu Asp Phe Phe Ser Arg Phe Pro Asp Leu Leu Arg Ser Met Ala Thr
            115             120             125

Glu Gly Asn Ile Thr Glu Leu Thr Ala Lys Pro Asp Ala Phe Ala Pro
        130             135             140

Cys Ile Thr Leu Lys Tyr Ala Gly Ile Asp Ile Asp Leu Leu Phe Gly
145             150             155             160

Arg Val Lys Leu Ser Gln Val Pro Arg Asn Leu Ser Leu Leu Asn Gln
                165             170             175

Asn Met Leu Arg Gly Leu Asn Asn Glu Glu Val Arg Ser Leu Asn Gly
            180             185             190

Val Arg Val Ala Asp Glu Ile Leu Asn Leu Val Pro Glu Pro Ala Ile
        195             200             205

Phe Arg Thr Ala Leu Arg Thr Ile Lys Leu Trp Gly Thr Arg Arg Ala
        210             215             220

Ile Ala Gly Asn Ile Tyr Gly Phe Pro Gly Gly Val Thr Trp Ala Ile
225             230             235             240

Leu Val Ala Arg Ile Cys Gln Leu Tyr Pro Lys Ala Thr Ser Ser Thr
                245             250             255

Ile Val Phe Lys Phe Phe Arg Ile Met Glu Lys Trp Arg Trp Pro Met
            260             265             270

Pro Val Leu Leu Lys Glu Ile Asp Asn Leu Asn Ala Leu Gly Leu Lys
        275             280             285

Val Trp Asn Pro Lys Ile Tyr Gly Ser Asp Lys Asn His Ile Met Pro
        290             295             300

Ile Ile Thr Pro Ala Tyr Pro Glu Met Cys Thr Thr His Asn Phe Ser
305             310             315             320

Leu Ser Thr Lys Ala Ile Leu Glu Lys Glu Leu Lys Arg Gly Gly Asp
                325             330             335

Ile Thr Asp Arg Val Met Ser Gly Lys Ala Ser Trp Lys Asp Leu Phe
            340             345             350

Ala Lys His Thr Phe Phe Thr Asn Gly Tyr Lys Tyr Tyr Leu Ser Val
            355             360             365

Val Ser Ala Ser Arg Asn Lys Glu Ser Gln Leu Phe Trp Ser Gly Phe
        370             375             380

Val Glu Ser Lys Val Arg Leu Leu Val Asn Lys Leu Glu Tyr His Pro
385             390             395             400

Ser Ile Ala Leu Ala His Pro Phe Asn Lys Gly Phe Thr Arg Val His
                405             410             415

Arg Cys Arg Thr Glu Glu Glu Val Asp Leu Val Lys Asn Gly Ser Leu
                420             425             430
```

-continued

```
Lys Phe His Ala Thr Asp Ile Ala Thr Ser Thr Thr Gly His Gly Leu
        435             440             445

Ser Val Glu Thr Thr Ser Lys Glu Lys Leu Asn Glu Thr Lys Asn Val
    450             455             460

Glu Gln Asp Glu Asn Leu Ile Met Val Tyr Thr Ala Thr His Tyr Ile
465             470             475             480

Gly Leu Glu Leu Ala Lys Gly Ala Lys Ser Leu Asp Leu Ser Tyr Glu
                485             490             495

Val Glu Glu Phe Lys Ser Ile Cys Thr Ser Ser Glu Ala Tyr Asn Gln
            500             505             510

Glu Glu Asn Ser Leu Gly Val Ala His Thr Lys Asn Cys Asp Leu Pro
        515             520             525

Asp Asp Val Phe Thr Glu Gly Glu Leu Lys Pro Thr Arg Pro Leu Lys
    530             535             540

Gln Lys Lys Lys Arg Pro Ala Thr Glu Asp Ser Asn Pro Val Pro Ser
545             550             555             560

Lys Arg Gln Gln Thr Ser Leu Ile Ala Val Gly
                565             570

<210> SEQ ID NO 15
<211> LENGTH: 600
<212> TYPE: PRT
<213> ORGANISM: Hortaea werneckii

<400> SEQUENCE: 15

Met Ala Glu Lys Gln Tyr Gly Val Thr Pro Ala Phe Ser Leu Glu Pro
1               5               10              15

Pro Ser Pro Lys Asp Leu Lys Leu Asn Asp Ala Leu Leu Ala Glu Phe
            20              25              30

Lys Ala Gln Asn Asn Phe Ala Pro Gln Ser Asp Thr Glu Lys Arg Glu
        35              40              45

Ala Ile Leu Lys Lys Leu Glu Gly Leu Leu Gln Arg Met Val Gln Glu
    50              55              60

Val Gly Arg Lys Lys Gly Leu Pro Gln Ser Ile Leu Glu Val Ala Gly
65              70              75              80

Gly Lys Val Phe Thr Tyr Gly Ser Tyr Arg Leu Gly Val Tyr Gly Pro
                85              90              95

Asn Ser Asp Val Asp Thr Leu Met Val Gly Pro Lys His Val Thr Arg
            100             105             110

Glu Asp Phe Phe Glu His Met Pro Pro Leu Ile Arg Ser Ala Trp Ala
        115             120             125

Glu Asp Gln Ile Gly Gly Leu Val Pro Val Pro Gly Ile Gly Thr Pro
    130             135             140

Ile Ile Lys Leu Glu Leu Glu Gly Val Asp Ile Asp Leu Ile Tyr Ser
145             150             155             160

Ser Leu Gln Leu Ser Ser Ile Pro Lys Asp Ile Glu Leu Lys Asp Asp
                165             170             175

Asn Leu Leu Arg Gly Leu Asp Asp Thr Asp Arg Arg Cys Val Asn Gly
            180             185             190

Thr Arg Val Thr Asn Arg Ile Leu Glu Leu Val Pro Gln Thr Lys Thr
        195             200             205

Phe Arg Leu Ala Leu Arg Ala Ile Lys Leu Trp Ser Ser Gln Arg Ala
    210             215             220

Ile Tyr Gly Asn Ile Val Gly Phe Pro Gly Gly Val Ala Trp Ala Ile
225             230             235             240
```

```
Leu Val Ala Arg Val Cys Gln Leu Tyr Pro Lys Ala Ala Ala Pro Leu
                245                 250                 255

Leu Ile Ser Lys Phe Phe Phe Ile Met Lys Arg Trp Asn Trp Pro Lys
                260                 265                 270

Pro Val Phe Leu Gln His Lys Glu Glu Thr Ser Leu Gln Leu Arg Glu
                275                 280                 285

Trp Asp Pro Ile Gln Tyr Arg Gly Asp Gly Phe His Leu Met Pro Ile
                290                 295                 300

Leu Thr Pro Ala Tyr Pro Ser Met Asn Thr Ala His Thr Val Gly Pro
305                 310                 315                 320

Ser Thr Lys Met Ile Ile Met Arg Glu Leu Glu Arg Gly Glu Asn Ile
                325                 330                 335

Val Asn Asp Ile Tyr Ala Asn Lys Arg Pro Trp Lys Asp Leu Phe Gln
                340                 345                 350

Arg His Thr Phe Phe Thr Asn Ala Tyr Lys His Tyr Ile Cys Val Val
                355                 360                 365

Val Ala Ala Lys Asn Lys Asp Ala His Asp Asn Trp Ser Gly Leu Val
                370                 375                 380

Asn Ser Lys Leu Lys Phe Leu Val Lys Gly Ile Glu Asp Ser Gly Gly
385                 390                 395                 400

Ser Ser Val Glu Leu Val Gln Pro Phe Asn Lys Gly Phe Ser Arg Val
                405                 410                 415

His Glu Cys Gln Thr Asn Glu Gln Val Glu Lys Val Leu Asp Gly Ser
                420                 425                 430

Leu Glu Cys Gln Val Lys Glu Thr Lys Thr Thr Glu Glu Gly Asn Asp
                435                 440                 445

Thr Ala Ile Ala Asn Gly Val Ala Gln Thr Asp Thr Glu Gly Leu Glu
        450                 455                 460

Val Pro Lys Ala Asp Ser Glu Ala Arg Ala Glu Gly Ser Gly Thr Thr
465                 470                 475                 480

Lys Leu Trp Thr Thr Thr Phe Tyr Leu Gly Ile Gly Leu Lys Lys Gly
                485                 490                 495

Ala Thr Asp Leu Asp Ile Ser Val Pro Val Arg Asn Leu Gln Gly Asp
                500                 505                 510

Cys Thr Ala Trp Ala Asp Tyr Asn Pro Asp Leu His Ser Ile Lys Ile
                515                 520                 525

Lys His Ile Arg Asn Phe Asn Leu Pro Asp Asp Val Phe Lys Glu Gly
        530                 535                 540

Glu Val Lys Pro Gln Arg Pro Lys Lys Lys Thr Asn Ala Ala Lys Ala
545                 550                 555                 560

Ala Glu Ala Thr Ser Asn Lys Arg Ser Phe Ser Asp Thr Gly Leu Asp
                565                 570                 575

Pro Asn Ala Asp Pro Ala Lys Arg Arg Gln Ser Gly Asn Val Pro Thr
                580                 585                 590

Pro Val Ala Asn Gly Ser Val Gly
                595                 600
```

<210> SEQ ID NO 16
<211> LENGTH: 589
<212> TYPE: PRT
<213> ORGANISM: Valsa sordida

```
<400> SEQUENCE: 16

Met Ala Glu Ile Gln Tyr Gly Met Thr Pro Pro Leu Ser Thr Glu Leu
1               5                   10                  15

Pro Lys Asp Pro Glu Lys Arg Ala Asn Asp Ala Leu Phe Ala Glu Leu
            20                  25                  30

Lys Ala Gln Asn Thr Tyr Glu His Ala Thr Glu Thr Gln Lys Arg Glu
        35                  40                  45

Lys Val Leu Lys Ser Leu Gln Ser Ile Ala Asp Val Phe Val Gln Lys
        50                  55                  60

Val Ala Gln Arg Val His Lys Glu Ser Pro Ala Ile Gln Lys Ser Ala
65                  70                  75                  80

Arg Gly Arg Val Phe Thr Tyr Gly Ser Tyr Arg Leu Gly Val Phe Gly
                85                  90                  95

Pro Gly Ser Asp Ile Asp Thr Leu Val Val Ala Pro Lys Tyr Val Thr
            100                 105                 110

Arg Glu Asp Phe Phe Glu Leu Phe Pro Gly Leu Leu Lys Glu Leu Ala
            115                 120                 125

Pro Ala Gly Ser Ile Thr Asp Leu Thr Ala Val Thr Asp Ala Phe Val
        130                 135                 140

Pro Ile Ile Lys Phe Glu Tyr Ser Asp Ile Ser Ile Asp Leu Ile Phe
145                 150                 155                 160

Ser Arg Ile Ala Thr Leu Thr Glu Ile Pro Ala Leu Thr Thr Lys Trp
                165                 170                 175

Asp Leu Leu Asp Asn Asn Leu Leu Arg Gly Leu Asp Asp Ala Glu Leu
            180                 185                 190

Arg Ser Leu Asn Gly Thr Arg Val Thr Asp Asp Ile Leu Lys Leu Val
            195                 200                 205

Pro Glu Gln Thr Ser Phe Arg Leu Ala Leu Arg Ala Ile Lys Leu Trp
        210                 215                 220

Ala Gln Arg Arg Ala Ile Tyr Ala Asn Ile Met Gly Phe Pro Gly Gly
225                 230                 235                 240

Val Ala Trp Ala Met Leu Val Ala Arg Ile Cys Gln Leu Tyr Pro Lys
                245                 250                 255

Ala Asn Gly Ala Val Ile Val Asp Lys Phe Phe His Ile Ile Arg Arg
            260                 265                 270

Trp Pro Trp Pro Gln Pro Val Leu Leu Lys Asn Pro Glu Asp Gly Pro
        275                 280                 285

Leu Gln Val Arg Val Trp Asn Pro Lys Val Tyr Lys Gly Asp Ser Tyr
        290                 295                 300

His Leu Met Pro Val Ile Thr Pro Ala Tyr Pro Ser Met Cys Ser Thr
305                 310                 315                 320

Phe Asn Val Thr His Ser Asn Lys Ala Val Ile Gln Lys Glu Leu Asp
            325                 330                 335

His Phe Ala Asp Val Val Gln Gln Ile Met Met Gly Lys Leu Pro Trp
            340                 345                 350

Lys Ser Leu Phe Val Lys His Thr Phe Phe Thr Lys Asp Tyr Lys Tyr
        355                 360                 365

Tyr Ile Ala Val Ile Ala Ala Ser Thr Thr Lys Glu Asn Ser Lys Ile
        370                 375                 380

Trp Gly Gly Phe Val Glu Ser Lys Ile Arg Leu Leu Val Gln Gly Leu
385                 390                 395                 400
```

```
Glu Arg His Ser Ser Ile Arg Leu Ala Arg Pro Phe Asn Lys Gly Tyr
            405                 410                 415

Glu Arg Lys His Arg Thr Val Ser Gly Met Asn Glu Trp His Asp Ile
            420                 425                 430

Leu Asp Gly Ser Leu Asp Tyr Val Val Lys Asp Glu Gln Val Ala Asp
            435                 440                 445

Glu Lys Ala Lys Thr Glu Pro Gly Asn Asp Ala Val Lys Thr Glu Pro
    450                 455                 460

Thr Ser Pro Ala Lys Val Lys Gln Glu Glu Gly Ile Glu Ser Leu Glu
465                 470                 475                 480

Ile Lys Asp Asp Ala Lys Glu Thr Asp Gly Lys Asn Glu Gln Asp Glu
                485                 490                 495

Glu Asp Ala Glu Val Lys Pro Glu Thr Glu Asp Pro Asp Ser Pro Lys
            500                 505                 510

Asp Val Tyr Thr Ser Thr His Tyr Ile Gly Ile Glu Leu His Asp Glu
            515                 520                 525

His Tyr Ser Trp Ser Leu Pro Asp Asp Val Phe Glu Ala Gly Glu Thr
            530                 535                 540

Lys Pro Thr Arg Pro Leu Lys Lys Lys Ala Ala Gln Pro Pro Asn Gly
545                 550                 555                 560

Ala Lys Arg Lys Thr Pro Thr Glu Gly Ala Leu Asn Ser Ala Ile Asp
                565                 570                 575

Ala Ala Lys Arg Gln Lys Thr Ser Thr Val Ser Ala Gly
            580                 585
```

```
<210> SEQ ID NO 17
<211> LENGTH: 588
<212> TYPE: PRT
<213> ORGANISM: Wallemia mellicola

<400> SEQUENCE: 17

Met Ala Glu Lys Gln Trp Gly Ile Thr Pro Pro Ile Ser Leu Ala Ser
1               5                   10                  15

Pro Thr Asp Leu Glu Lys Gln Val Asp Ala Gly Leu Ile Gln Glu Leu
            20                  25                  30

Lys Asp Gln Asn Thr Ile Glu Ser Glu Gln Glu Ser Leu Asn Arg Glu
            35                  40                  45

Lys Val Leu Ala Leu Val Gln Ser Leu Val Lys Glu Phe Val Lys Arg
    50                  55                  60

Val Ser Ile Arg Asn Gly Met Ser Glu Ser Leu Ala Asp Gln Ala Gly
65                  70                  75                  80

Gly Lys Ile Phe Thr Phe Gly Ser Tyr Arg Leu Gly Val Asn Gln Pro
                85                  90                  95

Gly Ala Asp Ile Asp Thr Leu Cys Val Val Pro Lys His Val Ser Arg
            100                 105                 110

Glu Asp Phe Phe Asp Val Phe Glu Pro Leu Leu Lys Thr Arg Glu Glu
            115                 120                 125

Val Ser Val Cys Ala Gly Val Pro Asp Ala Tyr Val Pro Ile Ile Lys
            130                 135                 140

Thr Thr Ile Ser Gly Ile Glu Ile Asp Phe Leu Val Ala Arg Leu Ala
145                 150                 155                 160

Leu Ala Thr Ile Pro Asp Asp Leu Glu Leu Ala Asp Asp Asn Leu Leu
                165                 170                 175
```

-continued

```
Lys Asn Leu Asp Glu Arg Cys Val Arg Ser Leu Asn Gly Ser Arg Val
        180                 185                 190

Thr Asp Glu Ile Leu Arg Val Val Pro Asn Val Gln Val Phe Arg Glu
        195                 200                 205

Ser Leu Arg Cys Ile Lys Leu Trp Ala Gln Arg Ala Ile Tyr Ser
        210                 215                 220

Asn Val Asn Gly Phe Leu Gly Gly Val Ala Trp Ala Met Leu Val Ala
225                 230                 235                 240

Arg Ile Cys Gln Leu Tyr Pro Asn Glu Asn Ala Gly Ala Val Ile Ala
                245                 250                 255

Lys Phe Phe Thr Ile Leu Tyr Gln Trp Lys Trp Pro His Pro Val Leu
                260                 265                 270

Leu Lys Glu Ile Glu Asp Gly Pro Leu Lys Val Arg Val Trp Asn Pro
        275                 280                 285

Lys Val Gly Ser Ser Thr Leu Leu Ile Tyr Pro Ser Asp Arg Ala His
        290                 295                 300

Arg Met Pro Ile Ile Thr Pro Ala Tyr Pro Ser Met Cys Ser Thr His
305                 310                 315                 320

Asn Val Gly Pro Ser Thr Gln Glu Val Met Arg Gln Glu Phe Lys Arg
                325                 330                 335

Gly Met Asp Ile Leu Asp Gly Ile His Lys Gly Thr Thr Thr Trp Ser
                340                 345                 350

Gln Leu Phe Asn Lys His Glu Phe Phe Ser Lys Tyr Lys His Tyr Leu
        355                 360                 365

Gln Ile Ile Ala Ser Gly Gln Thr Ala Glu Ser Gln Lys Lys Trp Ser
        370                 375                 380

Gly Ala Val Glu Ser Lys Val Arg Gln Leu Val Ser Lys Leu Glu Leu
385                 390                 395                 400

Val Asp Gly Ile Glu Leu Ala His Pro Phe Val Lys Gly Phe Ser Glu
                405                 410                 415

Val Phe Ile Cys Leu Asn Asp Glu Glu Val Gln His Ala Ala Glu Tyr
                420                 425                 430

Asn Pro Ser Glu Glu Val Lys Glu Arg Ser Lys Lys Pro Glu Glu Tyr
        435                 440                 445

Glu Asn Lys Glu Ala Glu Asp Gly Ile His Arg Val Tyr Ile Ser Thr
        450                 455                 460

Phe Tyr Ile Gly Leu Ala Ile Gln Pro Arg Asn Pro Glu Thr Asn Glu
465                 470                 475                 480

Lys Arg Thr Leu Asn Leu Thr Tyr Pro Thr Asn Glu Phe Met Lys Leu
                485                 490                 495

Thr Lys Leu Trp Asp Gln Phe Val Glu Gly Glu Met Lys Ile Phe Val
                500                 505                 510

Lys Asn Ile Lys Ala Ser Ala Leu Pro Asp Val Val Phe Glu Gly Gly
        515                 520                 525

Ile Arg Thr Ser Ser Ser Lys Ser Ser Lys Lys Lys Ser Lys Arg Pro
        530                 535                 540

Ser Asn Val Met Asp Glu Ser Asn Gly Glu Asn Glu Gln Asn Lys Arg
545                 550                 555                 560

Leu Lys Pro Asp Asn Thr Ser Asn Asn Glu Gln Lys Ser Glu Ala Thr
                565                 570                 575

Ala Leu Ala Pro Ser Ala Val Pro Thr Glu Ser Thr
                580                 585
```

<210> SEQ ID NO 18
<211> LENGTH: 587
<212> TYPE: PRT
<213> ORGANISM: Xylaria flabelliformis

<400> SEQUENCE: 18

```
Met Ala Glu Lys Thr Trp Gly Ile Thr Lys Pro Ile Ser Ser Ala Pro
1               5                   10                  15

Pro Thr Pro Ala Glu Ser His Ala Thr Ala Leu Leu Leu Glu Glu Leu
            20                  25                  30

Arg Arg Gln Asn Thr Phe Glu Thr Ala Ser Glu Ile Lys Lys Arg Glu
        35                  40                  45

Lys Val Val Asn Asp Leu Gln Arg Ile Ala Asp Glu Phe Val Arg Lys
    50                  55                  60

Val Ala Arg Ala Lys Glu Pro His Asn Glu Val Leu Ile Arg Asp Ala
65                  70                  75                  80

Arg Gly Glu Val Phe Thr Tyr Gly Ser Tyr Cys Leu Gly Val Tyr Gly
                85                  90                  95

Pro Gly Ser Asp Ile Asp Thr Leu Val Thr Ala Pro Arg Tyr Val Thr
            100                 105                 110

Arg Asp Asp Tyr Phe Lys Tyr Phe Pro Asp Leu Leu Thr Glu Met Ala
        115                 120                 125

Pro Pro Gly Ala Ile Thr Asn Leu Thr Ala Val Glu Asp Ala Phe Val
    130                 135                 140

Pro Ile Ile Lys Phe Glu Tyr Trp Gly Ile Ser Ile Asp Leu Ile Phe
145                 150                 155                 160

Ser Arg Ile Ala Thr Leu Thr Gln Phe Pro Pro His Lys Gln Leu Glu
                165                 170                 175

Leu Thr Ser Asn Glu His Leu Arg Gly Leu Asp Asp Arg Glu Leu Arg
            180                 185                 190

Ser Leu Asn Gly Thr Arg Val Thr Lys Glu Ile Leu Asn Leu Val Pro
        195                 200                 205

Glu Gln Ser Thr Phe Arg Thr Ala Leu Arg Ala Ile Lys Leu Trp Ala
    210                 215                 220

Gln Arg Arg Ala Ile Tyr Ala Asn Ile Ile Gly Phe Pro Gly Gly Val
225                 230                 235                 240

Val Trp Ala Met Met Val Ala Arg Val Cys Gln Leu Tyr Pro Lys Ala
                245                 250                 255

Thr Ser Ala Thr Ile Val Gly Lys Phe Phe Leu Val Met Lys Gly Trp
            260                 265                 270

Pro Trp Pro Ile Pro Val Gln Leu Lys His Met Glu Asp Gly Pro Leu
        275                 280                 285

Asn Val Arg Val Trp Asn Pro Lys Ile Tyr Lys Ser Asp Ser Phe His
    290                 295                 300

Leu Met Pro Val Ile Thr Pro Ala Tyr Pro Gln Met Cys Ala Thr Phe
305                 310                 315                 320

Asn Ile Thr Lys Ser Thr Lys Thr Ile Ile Gln Arg Glu Leu Glu Arg
                325                 330                 335

Gly Val Glu Leu Thr Asp Lys Ile Leu Gly Ser Glu Arg Pro Trp Lys
            340                 345                 350

Asp Leu Phe Val Lys His Thr Phe Phe Thr Gln Asp His Lys Tyr Tyr
        355                 360                 365

Leu Ala Val Ile Ala Thr Ser Thr Thr Lys Glu Ala His Lys Ile Trp
    370                 375                 380
```

-continued

```
Ser Gly Phe Val Glu Ser Lys Val Arg Ile Leu Val Gly Glu Leu Glu
385                 390                 395                 400

Arg His Ser Ser Ile Ala Leu Ala Arg Pro Phe Asn Lys Gly Phe Glu
                405                 410                 415

Arg Gln His Leu Thr Lys Thr Asp Gln Gln Ala Ala Glu Val Gln Ser
            420                 425                 430

Gly Ser Leu Ala Tyr Val Thr Glu Asp Glu Asp Asn Ser Asp Asp Ala
            435                 440                 445

Thr Val Thr Lys Ala Glu Asn Gly Thr Asp Gly Asn Ala Asp Ser Ser
        450                 455                 460

Asp Gln Lys Val Thr Ala Glu Asn Thr Thr Gln Pro Arg Arg Thr Tyr
465                 470                 475                 480

Thr Thr Thr His Tyr Ile Gly Leu Glu Leu Ala Glu Gly Ser Lys Ser
                485                 490                 495

Leu Asp Leu Ser Tyr Gln Val Asn Ala Phe Lys Gln Leu Cys Ser Glu
            500                 505                 510

Trp Glu Lys Tyr Ser Ala Glu Phe Asn Ser Leu Ser Val Gln His Val
            515                 520                 525

Lys Asn Ile Asn Leu Pro Glu Asp Val Phe Glu Pro Gly Glu Thr Lys
        530                 535                 540

Pro Ala Arg Pro Leu Lys Lys Pro Thr Ala Asn Gly Thr Ala Pro Thr
545                 550                 555                 560

Thr Gln Arg Lys Arg Asn Ala Pro Thr Glu Gly His Pro Pro Pro Ala
                565                 570                 575

Lys Arg Gln Gln Ser Ser Ala Ala Ala Ala Gly
            580                 585

<210> SEQ ID NO 19
<211> LENGTH: 592
<212> TYPE: PRT
<213> ORGANISM: Chaetomium globosum

<400> SEQUENCE: 19

Met Ser Glu Ile Ile Tyr Gly Val Thr Pro Pro Ile Ser Thr Thr Leu
1               5                   10                  15

Pro Thr Glu Pro Glu Lys Arg Leu Asn His Ala Leu His Gln Glu Leu
            20                  25                  30

Arg Ala Gln Gly Thr Phe Glu Ser Pro Gln Glu Thr Glu Lys Arg Lys
        35                  40                  45

Glu Val Leu Arg Gln Leu Glu Lys Ile Thr Thr Val Phe Val Gln Arg
    50                  55                  60

Ala Ala Ala Gln Lys Glu Pro Lys Asn Thr Phe Met Ile Arg Asp Ala
65                  70                  75                  80

Ile Gly Arg Val Phe Thr Tyr Gly Ser Tyr Arg Leu Gly Val Tyr Gly
                85                  90                  95

Pro Gly Ser Asp Met Asp Thr Leu Val Val Ala Pro Lys Tyr Val Thr
            100                 105                 110

Val Glu Gln Tyr Phe Glu Ile Phe Pro Glu Val Leu Val Glu Met Ala
            115                 120                 125

Pro Pro Gly Ala Ile Thr Asp Leu Thr Pro Val Pro Glu Ala Phe Val
        130                 135                 140

Pro Ile Ile Lys Phe Glu Phe Ser Gly Ile Ser Ile Asp Leu Ile Phe
145                 150                 155                 160
```

```
Cys Ser Ile Gln Thr Leu Lys Gln Leu Pro Asp Glu Lys Asn Trp Ser
            165                 170                 175

Leu Ala Asp Asn Asn Leu Leu Arg Gly Leu Ser Glu Asn Glu Val Arg
            180                 185                 190

Ser Leu Asn Gly Thr Arg Val Thr Asp Asp Ile Leu His Leu Val Pro
            195                 200                 205

Glu Pro Ala Thr Phe Lys Leu Ala Leu Arg Ala Ile Lys Leu Trp Ala
        210                 215                 220

Gln Arg Lys Ala Ile Tyr Ala Asn Ile Met Gly Tyr Pro Gly Gly Val
225                 230                 235                 240

Ala Trp Ala Met Leu Val Ala Arg Val Cys Gln Leu Tyr Pro Lys Ala
                245                 250                 255

Thr Ser Ala Val Val Val Asn Lys Phe Phe His Ile Met Phe Lys Trp
                260                 265                 270

Pro Trp Pro Leu Pro Val Leu Leu Lys Asp Ile Glu Tyr Gly Ser Pro
            275                 280                 285

Val Thr Arg Val Pro Val Trp Asn Pro Lys Ser Ser Arg Arg Ala Gly
        290                 295                 300

Pro Lys Arg His Arg Thr Ser Met Arg Ala Ser Ser Asn Arg Gly Cys
305                 310                 315                 320

Gly Cys Trp Leu Thr Asp Leu Arg Gly Thr Ile Leu Leu Pro Trp Pro
                325                 330                 335

Gly Pro Ser Thr Arg Val Thr Thr Glu Asn Thr Asp Ala Arg Thr Ile
            340                 345                 350

Gly Ser Trp Glu Glu Val Val Ser Val Gly Ser Leu Ala Tyr Val Tyr
            355                 360                 365

Lys Pro Pro Ala Asp Ser Glu Glu Lys Ala Lys Ala Glu Pro Lys Val
        370                 375                 380

Glu Pro Lys Arg Glu Val Lys Gln Glu Ile Lys Ala Glu Asn Arg Glu
385                 390                 395                 400

Pro Ala Ala Ala Glu Glu Lys Leu Glu Thr Arg Gly Glu Asp Gly Met
                405                 410                 415

Arg Ile Lys Gln Glu His Ser Glu Ser Thr Gln Pro Pro Pro Pro Ser
            420                 425                 430

Asn Val Lys Pro Glu Pro His His Asp Thr Asn Ser Glu Val Lys Leu
            435                 440                 445

Glu Asp Ile Pro Gln Lys Lys Lys Asp Glu Pro Asp Glu Met Glu Ile
        450                 455                 460

Tyr Thr Thr Asn His Tyr Ile Gly Leu Gln Leu Val Glu Gly Ala Lys
465                 470                 475                 480

Ser Leu Asp Leu Ser Arg Glu Val Asn Asp Trp Lys Ser Met Cys Thr
                485                 490                 495

Ser Asn Glu Leu Phe Asp Glu Gly Leu Met Phe Leu Ser Ile Gln His
            500                 505                 510

Leu Lys Asn Thr Asn Leu Pro Asp Asp Val Phe Glu Pro Gly Glu Thr
            515                 520                 525

Lys Pro Arg Pro Val Lys Lys Asn Leu Lys Arg Ala Ala Ser Glu Gly
        530                 535                 540

Pro Gly Asn Met Gln Pro Gln Pro Val Lys Arg His Ala Pro Gly
545                 550                 555                 560

Lys Pro Ser Ser His Ser Ala Gln Gln Gln Gln Gln Gln Gln Lys
            565                 570                 575
```

```
Gln Arg Gln Gln Arg Pro Ala Ser Thr Ala Ala Ala Ala Val Ala Gly
            580                 585                 590

<210> SEQ ID NO 20
<211> LENGTH: 591
<212> TYPE: PRT
<213> ORGANISM: Lachancea thermotolerans

<400> SEQUENCE: 20

Met Asn Gln Gln Lys Thr Tyr Gly Val Thr Gly Pro Ile Ser Thr Ala
1               5                   10                  15

Gly Pro Thr Ala Ala Glu Asn Gln Leu Asn Asp Ala Leu Ile Gln Glu
            20                  25                  30

Leu Lys Lys Glu Lys Ser Phe Glu Ser Glu Glu Asp Thr Lys Lys Arg
        35                  40                  45

Val Glu Val Leu Arg Ile Leu Gln Asn Leu Ala Gln Glu Phe Val Tyr
    50                  55                  60

Gln Val Ser Lys Lys Arg Asn Met Ser Asp Gly Met Ala Lys Asp Ala
65                  70                  75                  80

Gly Gly Lys Ile Phe Thr Tyr Gly Ser Tyr Arg Leu Gly Val His Gly
                85                  90                  95

Pro Gly Ser Asp Ile Asp Thr Leu Val Val Val Pro Lys His Val Thr
            100                 105                 110

Arg Glu Asp Phe Phe Thr Val Phe Asp Gln Ile Leu Arg Thr Arg Ser
            115                 120                 125

Glu Leu Glu Glu Ile Ala Pro Val Pro Asp Ala Phe Val Pro Ile Ile
    130                 135                 140

Lys Ile Lys Phe Ser Gly Ile Ser Ile Asp Leu Ile Cys Ala Arg Leu
145                 150                 155                 160

Asp Ile Ala Gln Val Pro Val Asn Leu Thr Leu Ala Asp Lys Asn Leu
                165                 170                 175

Leu Arg Asn Leu Asp Glu Lys Asp Leu Arg Ala Leu Asn Gly Thr Arg
            180                 185                 190

Val Thr Asp Glu Ile Leu Gln Leu Val Pro Lys Pro Thr Ser Phe Lys
            195                 200                 205

Ile Ala Leu Arg Ala Ile Lys Leu Trp Ala Gln Arg Arg Ala Val Tyr
    210                 215                 220

Ala Asn Ile Phe Gly Phe Pro Gly Gly Val Ala Trp Ala Met Leu Val
225                 230                 235                 240

Ala Arg Ile Cys Gln Leu Tyr Pro Asn Ala Cys Ser Ala Val Ile Leu
                245                 250                 255

Thr Arg Phe Phe His Ile Leu Thr Lys Trp Asn Trp Pro Gln Pro Val
            260                 265                 270

Leu Leu Lys Pro Ile Glu Asp Gly Pro Leu Gln Val Arg Val Trp Asn
            275                 280                 285

Pro Arg Ile Tyr Ala Gln Asp Arg Ser His Lys Met Pro Val Ile Thr
    290                 295                 300

Pro Ala Tyr Pro Ser Met Cys Ala Thr His Asn Ile Ser Glu Ser Thr
305                 310                 315                 320

Lys Lys Val Ile Leu Ala Glu Leu Glu Arg Gly Ala Gln Ile Ser Ser
                325                 330                 335

Glu Ile Phe Ser Asn Lys Lys Thr Trp Ser Asp Leu Phe Gln Lys His
            340                 345                 350

Asp Phe Phe Tyr Lys Tyr Lys Phe Tyr Leu Thr Val Met Ala Ser Thr
            355                 360                 365
```

-continued

```
Ser Gly Ser Ser Glu Gln His Leu Lys Trp Ser Gly Leu Val Glu Ser
    370             375             380

Lys Leu Arg Leu Leu Val Gln Lys Leu Glu Thr Leu Gly Gly Ile Asn
385             390             395             400

Leu Ala His Pro Phe Thr Lys Pro Phe Glu Ala Ser Tyr Val Tyr Asp
                405             410             415

Asn Glu Ala Gln Cys Lys Asp Ile Ile Asp Asn Tyr Gly Thr His Lys
            420             425             430

Ala Gln Asp Ile Leu Ala Gln Tyr Thr Glu Val Thr Asp Asp Asn Lys
        435             440             445

Asp Thr Asp Gly Val Lys Asp Lys Ala Gln Val His Ile Thr Thr Met
    450             455             460

Tyr Ile Gly Leu Asp Val Ala Leu Asp Gly Lys Lys Gln Val Asp Ile
465             470             475             480

His Val Pro Cys Ser Asp Phe Phe Asn Leu Cys Arg Ser Phe Ser Glu
                485             490             495

Tyr Asp Asp Thr Asp Met Phe Ser Leu Met Ile Lys Tyr Val Lys Leu
            500             505             510

Tyr Asp Leu Pro Asp Asn Val Tyr Val Glu Gly Glu Glu Arg Pro Val
        515             520             525

Lys His Ser Lys Arg Lys Lys Leu Gly Lys Asp Ser Lys Lys Ser Lys
    530             535             540

Arg Pro Lys Ser Asn Ser Leu Lys Ala Glu Glu Pro Thr Ser Gly Thr
545             550             555             560

Thr Asn Ser Glu Lys Asn Asn Ser Gln Gly Pro Asn Lys Pro Val Lys
                565             570             575

His Glu Pro Pro Met Gln Thr Ser Pro Asn Pro Leu Ala Gly Ser
            580             585             590

<210> SEQ ID NO 21
<211> LENGTH: 558
<212> TYPE: PRT
<213> ORGANISM: Schizosaccharomyces octosporus

<400> SEQUENCE: 21

Met Ser Val Lys Gln Trp Gly Ile Thr Pro Pro Ile Ser Thr Ala Pro
1               5               10              15

Ala Thr Glu Gln Glu Asn Ala Leu Asn Thr Ala Leu Ile Asp Glu Leu
            20              25              30

Lys Arg Gln Asn Leu Phe Glu Ser Ser Ala Glu Ser Glu Arg Arg Ile
        35              40              45

Lys Val Leu Asp Asp Leu Gln Arg Ile Ala Thr Glu Phe Val Lys Lys
    50              55              60

Val Ser Leu Ala Lys His Met Asn Glu Lys Met Ala Asn Glu Ala Gly
65              70              75              80

Gly Lys Ile Phe Thr Tyr Gly Ser Tyr Arg Leu Gly Val Tyr Gly Pro
                85              90              95

Gly Ser Asp Ile Asp Thr Leu Leu Val Val Pro Lys His Val Ser Arg
            100             105             110

Glu Asn Phe Phe Gln Asp Leu Glu Pro Met Leu Arg Glu Arg Glu Glu
        115             120             125

Ile Thr Glu Leu Ala Ser Val Pro Asp Ala Tyr Val Pro Ile Ile Lys
    130             135             140
```

-continued

```
Phe Lys Tyr Phe Asp Ile Ser Ile Asp Leu Ile Phe Ala Arg Leu Ser
145                 150                 155                 160

Val Pro Lys Val Pro Arg Thr Leu Glu Leu Ser Asp Asn Asn Leu Leu
                165                 170                 175

Lys Gly Val Glu Glu Arg Cys Ile Leu Ser Leu Asn Gly Thr Arg Val
                180                 185                 190

Thr Asp Gln Ile Leu Gln Leu Val Pro Asn Arg Ala Val Phe Lys His
                195                 200                 205

Ala Leu Arg Ala Val Lys Phe Trp Ala Gln Arg Arg Ala Ile Tyr Ala
        210                 215                 220

Asn Val Ile Gly Phe Pro Gly Gly Val Ala Trp Ala Met Met Val Ala
225                 230                 235                 240

Arg Ile Cys Gln Leu Tyr Pro Asn Ala Val Ser Ser Val Ile Val Ala
                245                 250                 255

Lys Phe Phe Arg Ile Leu His Gln Trp Asn Trp Pro Gln Pro Ile Leu
                260                 265                 270

Leu Lys Pro Ile Glu Asp Gly Pro Leu Gln Val Arg Ile Trp Asn Pro
        275                 280                 285

Lys Leu Tyr Pro Ser Asp Lys Ala His Arg Met Pro Ile Ile Thr Pro
        290                 295                 300

Ala Tyr Pro Ser Met Cys Ala Thr His Asn Ile Thr Pro Ser Thr Gln
305                 310                 315                 320

Ala Ile Ile Leu Ser Glu Met Val Arg Ala Gly Glu Ile Ala Asp Gln
                325                 330                 335

Ile Met Val Gly Ser Val Gly Trp Ser Ala Leu Phe Gln Lys His Asp
                340                 345                 350

Phe Phe His Arg Tyr Lys His Tyr Leu Met Ile Thr Ala Ala Ser Lys
        355                 360                 365

Thr Ala Glu Gly Gln Leu Lys Trp Ser Gly Leu Val Glu Ser Lys Leu
        370                 375                 380

Arg His Leu Val Thr Arg Leu Glu Leu Val Glu Ala Ile Ala Leu Ala
385                 390                 395                 400

His Pro Phe Asn Lys Gly Phe Asp Lys Ile His Asn Cys Lys Ser Glu
                405                 410                 415

Glu Glu Ala His Gln Leu Ala Ser Gly Ile Ser Leu Asp Val Ala Ser
                420                 425                 430

Gln Thr Ala Asp Leu Glu Arg Leu Ala Ala Asp Ala Asn Gly Gln Asn
        435                 440                 445

Glu Asn Glu Asp Glu Lys Glu Glu Lys Lys Ile Tyr Pro Val Tyr Thr
        450                 455                 460

Thr Thr Phe Tyr Ile Gly Leu Glu Leu Glu Lys Lys Lys Gly Gln Pro
465                 470                 475                 480

Ile Lys Lys Leu Asp Ile Ser Trp Pro Ala Gln Glu Phe Tyr Glu Leu
                485                 490                 495

Cys Lys Lys Trp Asp Arg Tyr Asp Glu Thr Gln Val Asn Val Phe Ile
                500                 505                 510

Lys Asn Thr Arg Asn Val Asn Leu Pro Asp Glu Val Phe Glu Pro Gly
        515                 520                 525

Glu Glu Lys Pro Lys Ser Ser Lys Lys Arg Ser Tyr Asn Asp Ala Gly
        530                 535                 540

Asn Asn Asn Glu Thr Met Lys Arg Gln Lys Ile Ser Thr Ala
545                 550                 555
```

-continued

<210> SEQ ID NO 22
<211> LENGTH: 608
<212> TYPE: PRT
<213> ORGANISM: Exophiala spinifera

<400> SEQUENCE: 22

Met Ala Glu Lys Gln Trp Gly Met Thr Pro Pro Met Ser Thr Ala Leu
1               5                   10                  15

Pro Glu Pro Ile Asp Thr Glu Lys Thr Ala Asp Leu Ile Glu Glu Leu
            20                  25                  30

Lys Lys Glu Asn Asn Tyr Glu Pro Leu Glu Ala Thr Gln Lys Arg Met
        35                  40                  45

Ala Thr Leu Gly Leu Leu Asn Arg Val Thr Gln Glu Phe Val Arg Glu
    50                  55                  60

Val Ser Arg Arg Arg Arg Met Pro Pro Ser Gln Ile Glu Gln Phe Gly
65                  70                  75                  80

Gly Lys Ile Phe Pro Tyr Gly Ser Tyr Arg Leu Gly Val Phe Gly Pro
                85                  90                  95

Gly Ser Asp Ile Asp Thr Leu Ala Val Ala Pro Arg His Val Thr Arg
            100                 105                 110

Glu Asp Phe Phe Glu Tyr Phe Pro Thr Val Leu Lys Arg Met Thr Ala
        115                 120                 125

Glu Gly Asp Ile Ser Ser Leu Thr Pro Val Pro Asp Ser Tyr Val Pro
    130                 135                 140

Ile Ile Lys Leu Val Leu Asn Asp Ile Glu Ile Asp Leu Ile Phe Ala
145                 150                 155                 160

Ser Ile Ala Ser Leu Gln Thr Ile Pro Lys Asn Leu Thr Leu Asn Asp
                165                 170                 175

Asn Asn Leu Leu Thr Gly Leu Asp Gln Ala Thr Ile Arg Ala Val Thr
            180                 185                 190

Gly Pro Arg Val Thr Asp Glu Ile Leu Ser Leu Val Pro Glu Gln Lys
        195                 200                 205

Thr Phe Arg Thr Ala Leu Arg Ala Ile Lys Leu Trp Ala Gln Arg Arg
    210                 215                 220

Ala Val Tyr Ala Asn Ile Val Gly Tyr Pro Gly Gly Val Ala Trp Ala
225                 230                 235                 240

Met Leu Val Ala Arg Val Cys Gln Leu Tyr Pro His Ala Val Gly Ala
                245                 250                 255

Thr Leu Val Asp Lys Phe Phe Phe Val Met Lys Asn Trp Asp Trp Pro
            260                 265                 270

Thr Pro Val Met Leu Lys Asp Ile Glu Gln Pro Lys Pro Ser Gln Ala
        275                 280                 285

Asn Glu Phe Lys Val Trp Asn Pro Ala Leu Tyr Lys Gly Asp Lys Lys
    290                 295                 300

Met Leu Met Pro Ile Ile Thr Pro Ala Phe Pro Ser Met Ser Ala Thr
305                 310                 315                 320

Tyr Asn Ile Ser Lys Ser Gly Lys Thr Val Ile Leu Arg Glu Leu Glu
                325                 330                 335

Arg Ala Ser Gln Ile Thr Asn Asn Ile Phe Ala Gly Lys Ala Arg Trp
            340                 345                 350

Ser Asp Leu Phe Lys Lys His Ser Phe Phe Thr Ala Asp His Lys Tyr
        355                 360                 365

Tyr Leu Gly Val Thr Ala Ser Thr Leu Asn Ala Asp Ser Ala Lys Gln
    370                 375                 380

-continued

```
Trp Ala Gly Leu Val Glu Ser Lys Val Arg Ile Phe Val Met Leu Leu
385                 390                 395                 400

Glu Gly Ile Pro Asp Ile Thr Leu Ala Arg Pro Phe Thr Lys Gly Phe
                405                 410                 415

Lys Arg Val His Lys Cys Ala Asp Glu Thr Gln Ile Arg Glu Val Gln
            420                 425                 430

Lys Gly Ser Met Lys Tyr Lys Phe Glu Glu Thr Lys Thr Val Glu Thr
            435                 440                 445

Thr Asp Pro Glu Leu Val Thr Ser Asn Gly Asp Gly Ala Ala Val Pro
        450                 455                 460

Ala Ala Asn Gly Ala Lys Pro Glu Thr Asp Gln Gly Ala His Thr Val
465                 470                 475                 480

Tyr Thr Tyr Thr Phe Tyr Ile Gly Ile Asp Thr Thr Ala Lys Gly Ser
                485                 490                 495

Leu Asn Ile Ala Pro Ser Phe Gln Asn Phe Lys Asp Ile Cys Glu Gly
            500                 505                 510

Trp Ala Ser Phe Asn Arg Asp Ser His Phe Leu Thr Leu Ala Ser Val
            515                 520                 525

Lys Cys Trp Asp Leu Pro Asp Asp Val Phe Asp Ala Lys Ala Gly Glu
        530                 535                 540

Val Lys Pro Ser Arg Pro Val Lys Lys Val Ala Lys Gln Val Lys Ala
545                 550                 555                 560

Glu Ala Lys Ser Gly Val Arg Arg Ser Ile Asn Glu Val Glu Ala Thr
                565                 570                 575

Glu Thr Asn Gly Asp Ala Ala Lys Arg Gln Lys Leu Met Thr Pro Thr
            580                 585                 590

Pro Thr Pro Thr Pro Thr Pro Ala Pro Lys Pro Thr Ala Ala Pro Ala
        595                 600                 605

<210> SEQ ID NO 23
<211> LENGTH: 626
<212> TYPE: PRT
<213> ORGANISM: Scedosporium apiospermum

<400> SEQUENCE: 23

Met Ala Asp Arg Gln Leu Gly Val Thr Pro Pro Ile Ser Met Ala Leu
1               5                   10                  15

Pro Thr Pro Ala Glu Ile Glu Ala Asn Asn Ala Met Val Glu Glu Leu
            20                  25                  30

Arg Lys Gln Gly Ile Phe Glu Ser Lys Glu Glu Thr Asp Lys Arg Asn
        35                  40                  45

Leu Val Leu Glu Ser Leu Gln Lys Met Cys Asp Glu Phe Val Thr Arg
        50                  55                  60

Val Ala Gln Glu Lys Asp Gln Gly Leu Ala Arg Asp Ala Arg Gly Lys
65                  70                  75                  80

Ile Phe Thr Tyr Gly Gly Phe Arg Leu Gly Val Phe Gly Pro Gly Ser
                85                  90                  95

Asp Ile Asp Thr Leu Val Val Ala Pro Lys Tyr Val Thr Arg Asp Asp
            100                 105                 110

Tyr Phe Ala Ile Phe Pro Asp Leu Leu Leu Glu Met Ala Pro Lys Gly
        115                 120                 125

Ala Ile Thr Gly Leu Ala Val Val Thr Asp Ala Phe Val Pro Ile Ile
    130                 135                 140
```

-continued

```
Lys Phe Glu Tyr Trp Gly Ile Ser Ile Asp Met Ile Phe Ser Arg Ile
145                 150                 155                 160

Ala Met Leu Lys Lys Leu Pro Thr Asn Thr Ser Gln Phe Asn Leu Thr
                165                 170                 175

Asp Thr Ala Leu Leu Arg Gly Leu Asp Glu Thr Glu Ile Arg Ser Leu
                180                 185                 190

Asn Gly Thr Arg Val Ala His Glu Ile Leu Asp Leu Val Pro Glu Gln
                195                 200                 205

Ser Thr Phe Gln Met Ala Leu Arg Ala Ile Lys Leu Trp Ala Gln Arg
        210                 215                 220

Arg Ala Ile Tyr Ala Asn Val Met Gly Tyr Pro Gly Gly Val Ala Trp
225                 230                 235                 240

Ala Met Leu Val Ala Arg Val Cys Gln Leu Tyr Pro Arg Ala Thr Ala
                245                 250                 255

Ala Thr Ile Val Ser Lys Phe Phe Cys Ile Met Arg Gln Trp Pro Trp
                260                 265                 270

Pro Gln Pro Val Leu Leu Lys His Ile Glu Arg Ala Pro Leu Gly Tyr
        275                 280                 285

Arg Ile Trp Asn Pro Val Val Tyr Pro Ser Asp Lys His His Leu Met
        290                 295                 300

Pro Ile Ile Thr Pro Ala Tyr Pro Ser Met Asn Ala Ala Tyr Asn Ile
305                 310                 315                 320

Asn Arg Ser Ser Met Ser Ile Ile Gln Thr Glu Leu Ser Arg Ala Asp
                325                 330                 335

Gly Ile Thr Asp Gly Ile Val Val Gly Gln Arg Pro Trp Ser Asp Leu
                340                 345                 350

Phe Glu Lys His Thr Phe Phe Thr Ala Asp Tyr Lys Tyr Tyr Leu Ala
        355                 360                 365

Ile Val Ser Ser Gly Ile Thr Lys Asp Ala His Lys Lys Trp Ser Gly
        370                 375                 380

Phe Val Glu Ser Lys Val Arg Met Leu Val Leu Ala Leu Asp Arg His
385                 390                 395                 400

Asp Thr Ile Ala Leu Ala Gln Ala Phe Val Lys Gly Tyr Asp Arg Val
                405                 410                 415

His Lys Cys Asn Ala Asp Ser Glu Ile Gln Lys Val Gln Gln Gly Asp
                420                 425                 430

Leu Ala Tyr Met Ile Lys Glu Glu Asp Ala Pro Lys Glu Glu Gln Thr
        435                 440                 445

Ser Pro Val Lys Ser Glu Thr Lys Pro Asp Pro Gly Ala Asn Glu Lys
        450                 455                 460

Asn Ser Ala Gly Gly Ser Asn Ser Asn Gly Asp Val Ala Gly Ser Ala
465                 470                 475                 480

Asp Ala Val Lys Asn Glu Glu Gly Ala Asn Gly Val Lys Ala Gly Asp
                485                 490                 495

Glu Asn Val Tyr Ile Tyr Thr Thr Thr His Tyr Ile Gly Leu Ala Leu
                500                 505                 510

Arg Pro Gly Gln Lys Ser Ile Asn Leu Ala Asn Glu Val Gly Glu Phe
        515                 520                 525

Lys Lys Leu Cys Lys Gly Trp Glu Lys Phe Asp His Gln Leu Asn Ala
        530                 535                 540

Ile Thr Val Gln His Leu Arg Asn Ser Asp Leu Pro Asp Asp Val Phe
545                 550                 555                 560
```

-continued

```
Ala Glu Gly Glu Val Lys Pro Arg Lys Arg Val Val Arg Lys Ala Asn
            565             570             575

Gly Thr Gly Pro Ser Pro Pro Val Asp Ala Lys Gln Ala Thr Asn Gly
            580             585             590

Thr Thr Ser Gln Val Asp Ser Lys Lys Arg Ala Ala Ala Glu Thr Gly
            595             600             605

Ala Ala Ala Pro Ala Ala Lys Arg Arg Gln Pro Ala Ser Val Val Ala
            610             615             620

Ala Gly
625

<210> SEQ ID NO 24
<211> LENGTH: 613
<212> TYPE: PRT
<213> ORGANISM: Trichoderma citrinoviride

<400> SEQUENCE: 24

Met Ala Glu Gln Asn Tyr Gly Val Thr Pro Pro Ile Ser Val Thr Leu
1               5               10              15

Pro Thr Glu Ala Glu Asn Arg Ala Ser Asp Ala Leu Leu Glu Glu Leu
            20              25              30

Arg Arg Gln Lys Thr Phe Glu Ser Pro Ser Asp Thr Glu Lys Arg His
            35              40              45

Glu Ile Cys Asn Glu Phe Val Arg Lys Val Ala Arg Glu Arg Glu Pro
        50              55              60

Lys Asn Glu Ile Leu Ile Lys Asn Ala Arg Gly Lys Val Phe Thr Tyr
65              70              75              80

Gly Ser Phe Arg Leu Gly Val Phe Gly Pro Gly Ser Asp Ile Asp Thr
            85              90              95

Leu Ile Val Ala Pro Lys Tyr Val Thr Arg Glu Asp Tyr Phe Asn Tyr
            100             105             110

Phe Pro Asp Leu Leu Val Ser Met Ala Pro Pro Gly Ala Ile Thr Asp
            115             120             125

Leu Thr Val Val Lys Asp Ala Phe Val Pro Ile Ile Lys Phe Glu Tyr
            130             135             140

Ser Gly Ile Ser Ile Asp Leu Ile Phe Ser Arg Ile Ile Gln Lys Gln
145             150             155             160

Ile Ala Pro Asp Phe His Ser Leu Lys Asp Ser Ser Leu Leu Arg Gly
            165             170             175

Leu Asp Glu Ala Glu Leu Arg Ser Leu Asn Gly Thr Arg Val Thr Asp
            180             185             190

Glu Ile Leu Glu Leu Val Pro Glu Lys Ser Thr Phe Lys Leu Ala Leu
            195             200             205

Arg Ala Ile Lys Leu Trp Ala Gln Arg Arg Ala Val Tyr Ala Asn Ile
            210             215             220

Met Gly Phe Pro Gly Gly Val Ala Trp Ala Met Leu Val Ala Arg Val
225             230             235             240

Cys Gln Leu Tyr Pro Lys Ala Thr Met Ser Val Ile Val Asn Lys Phe
            245             250             255

Phe Leu Val Ile Gly Gln Trp Arg Trp Pro Gln Pro Val Leu Leu Lys
            260             265             270

Pro Ile Glu Gly Gly Pro Leu Pro Val Arg Val Trp Asn Pro Lys Val
            275             280             285

Tyr Lys Gly Asp Ser Phe His Leu Met Pro Val Ile Thr Pro Ala Tyr
            290             295             300
```

-continued

```
Pro Ser Met Cys Ala Thr Phe Asn Ile Thr Arg Ser Ser Met Thr Ile
305                 310                 315                 320

Ile Gln Arg Glu Leu Arg Arg Gly Leu Glu Ile Ser Glu Gln Ile Met
                325                 330                 335

Val Gly Lys Arg Pro Trp Ser Asp Leu Phe Val Lys His Thr Phe Phe
                340                 345                 350

Thr Ser Gly Tyr Arg Tyr Tyr Ile Ser Val Val Ser Ala Ser Lys Asp
                355                 360                 365

Lys Glu Ala His Lys Val Trp Ser Gly Tyr Val Glu Ser Lys Ile Arg
                370                 375                 380

Met Leu Val Gln Lys Leu Glu Gln His Pro Ser Ile Ala Leu Ala His
385                 390                 395                 400

Ala Phe Asn Lys Gly Tyr Asp Arg Arg His Leu Cys Arg Asn Glu Gln
                405                 410                 415

Glu Ile Gly Gln Val Gln Glu Gly Ser Leu Glu Phe Met Ile Lys Asp
                420                 425                 430

Trp Asp Asp Asn Lys Leu Asn Gly Ala Ala Ile Lys Pro Glu Lys Val
                435                 440                 445

Glu Gly Asp Ser Lys Pro Asn Gly Ala Asp Ile Ile Gln Pro Glu Lys
                450                 455                 460

Val Glu Gly Glu Ser Lys Leu Ser Asp Ile Pro Val Lys Pro Glu Met
465                 470                 475                 480

Asp Glu Ala Glu Ser Lys Leu Ser Glu Val Ala Ile Lys Thr Glu Thr
                485                 490                 495

Lys Asp Gly Ser Thr Glu Ser Val Phe Pro Val Glu Val Tyr Thr Thr
                500                 505                 510

Thr His Tyr Ile Gly Leu Glu Leu Glu Glu Gly Ala Lys Ser Leu Asp
                515                 520                 525

Leu Ser Tyr Gln Val Asp Glu Phe Lys Val Leu Cys Thr Ser Trp Lys
                530                 535                 540

Lys Tyr Gln Glu Asp Leu Glu His Leu Val Ser Leu Gly Val Gln His
545                 550                 555                 560

Val Arg Asn Phe Asn Leu Pro Asp Asp Val Phe Glu Pro Gly Glu Gln
                565                 570                 575

Lys Pro Gln Lys Lys Ser Ser Ala Lys Ser Leu Ala Asn Lys Lys Arg
                580                 585                 590

Gly Ala Pro Glu Asp Asn Thr Pro Pro Ala Lys Arg Gln Gln Ala Ser
                595                 600                 605

Val Ala Ala Ala Gly
    610
```

```
<210> SEQ ID NO 25
<211> LENGTH: 598
<212> TYPE: PRT
<213> ORGANISM: Aspergillus thermomutatus

<400> SEQUENCE: 25

Met Ser Ala Pro Pro Val Arg Gln Trp Gly Val Thr Pro Pro Ile Ser
1               5                   10                  15

Thr Ala Leu Pro Thr Pro Asp Glu Leu Ala Ala Asn Asp Asp Leu Ile
                20                  25                  30

Ser Glu Leu Lys Ala Gln Asn Asn Phe Glu Ser Pro Ala Glu Thr Glu
                35                  40                  45
```

-continued

```
Arg Arg Lys Gln Val Leu Gln Leu Ile Gln Arg Val Thr His Glu Phe
    50              55              60

Val Lys Val Val Ser Arg Lys Lys Gly Leu Ser Pro Ala Ala Val Glu
65              70              75              80

Ala Ala Gly Gly Lys Ile Phe Thr Tyr Gly Ser Tyr Arg Leu Gly Val
                85              90              95

Tyr Gly Pro Gly Ser Asp Ile Asp Thr Leu Val Val Gly Pro Lys His
            100             105             110

Val Leu Ile Asp Asp Phe Phe Ser Asp Phe Pro Pro Val Leu Glu Lys
        115             120             125

Met Ala Pro Pro Gly Ala Ile Glu Lys Met Thr Pro Val Pro Asp Ala
    130             135             140

Phe Val Pro Ile Ile Lys Leu Glu Leu Ser Gly Ile Ser Ile Asp Leu
145             150             155             160

Ile Phe Ala Arg Leu Ile Val Ser Ser Val Pro Leu Asn Leu Asp Leu
            165             170             175

Lys Asn Asn Asp Tyr Leu Arg Gly Leu Asp Glu Lys Glu Val Arg Ser
            180             185             190

Leu Asn Gly Thr Arg Val Thr Asp Glu Ile Leu Glu Leu Val Pro Gln
        195             200             205

Gln Lys Thr Phe Arg Leu Ala Leu Arg Ala Ile Lys Leu Trp Ala Gln
    210             215             220

Arg Arg Ala Ile Tyr Ser Asn Ile Val Gly Phe Pro Gly Gly Val Ala
225             230             235             240

Trp Ala Met Leu Val Ala Arg Val Cys Gln Leu Tyr Pro His Ala Thr
            245             250             255

Gly Ser Val Ile Val Gly Lys Phe Phe Arg Ile Met Asn Lys Trp Ala
            260             265             270

Trp Pro Gln Pro Val Leu Leu Lys Pro Ile Glu Asp Gly Pro Leu Gln
    275             280             285

Ile Lys Val Trp Asn Pro Lys Ile Tyr His Gly Asp Arg Phe His Leu
    290             295             300

Met Pro Ile Ile Thr Pro Ala Tyr Pro Ser Met Cys Ala Thr His Asn
305             310             315             320

Ile Ser Met Ser Thr Lys Ala Val Ile Leu Arg Glu Leu Gln Arg Gly
            325             330             335

Gly Asp Ile Val Asp Lys Ile Phe Leu Lys Gln Leu Thr Trp Asn Asp
            340             345             350

Leu Phe Ala Arg His Ser Phe Phe Thr His Asp Tyr Lys Tyr Tyr Leu
        355             360             365

Ser Ile Thr Ala Ser Ser Arg Thr Lys Glu Ala Glu Ser Val Trp Ser
    370             375             380

Gly Leu Val Glu Ser Lys Ile Arg His Leu Val Gly Ala Leu Asp Arg
385             390             395             400

Lys Pro Thr Ile Ala Val Ala His Pro Phe Pro Lys Gly Phe Glu Arg
            405             410             415

Val His Ile Ile Ser Asn Glu Glu Glu Ala Glu Ala Val Lys Asn Gly
            420             425             430

Ser Thr Lys Tyr Gln Asp Lys Gly Thr Lys Thr Glu Thr Thr Asp Glu
        435             440             445

Thr Lys Asp Ala Ala His Gln Ala Ala Ala Gln Ser Gly Val Glu Asn
    450             455             460
```

-continued

```
Ala Glu Val Glu Pro Val Gly Glu Asn Ala Asn Gly Asp Ser Arg Ile
465                 470                 475                 480

Ile Tyr Thr Thr Thr Tyr Tyr Ile Gly Leu Glu Leu Lys Pro Leu Glu
                485                 490                 495

Pro Gly Ala Ser Arg Ser Leu Asp Ile Ser Thr Asp Ala Gln Ile Phe
            500                 505                 510

Lys Ser Thr Cys Thr Ser Trp Ala Gly Tyr Gln Pro Gly Ile Asn Asp
        515                 520                 525

Leu Ser Ile Thr His Val Arg Asn Phe Asp Leu Pro Glu Asp Val Phe
        530                 535                 540

Gln Pro Gly Glu Ala Arg Pro Thr Arg Pro Lys Lys Lys Val Ile Lys
545                 550                 555                 560

Lys Pro Glu Ala Gly Ala Gln Lys Arg Gly Ile Asp Ser Leu Asp Asp
            565                 570                 575

Ala Ser Leu Pro Ala Ala Lys Arg Gln Val Thr Ser Asn Gly Ile Ser
            580                 585                 590

Ser Thr Pro Thr Pro Ala
        595
```

```
<210> SEQ ID NO 26
<211> LENGTH: 579
<212> TYPE: PRT
<213> ORGANISM: Sodiomyces alkalinus

<400> SEQUENCE: 26
```

```
Met Gln Asp Arg Pro Leu Gly Val Thr Pro Pro Ile Ser Thr Ser Leu
1               5                   10                  15

Pro Thr Asp Ala Glu His Ala Val Asn Glu Ser Leu Leu Glu Glu Leu
            20                  25                  30

Lys Arg Gln Asn Thr Phe Glu Ser Pro Ala Glu Thr Ala Lys Arg Glu
        35                  40                  45

Lys Val Leu Glu Gln Leu Gln Leu Ile Cys Asn Glu Phe Val Arg Arg
        50                  55                  60

Val Ala Arg Glu Arg Glu Ala Gly Ser Glu Ala Leu Ile Lys Glu Ala
65                  70                  75                  80

Arg Gly Arg Ile Phe Thr Tyr Gly Ser Phe Arg Leu Gly Val Tyr Gly
                85                  90                  95

Pro Gly Ser Asp Ile Asp Ala Leu Val Val Ala Pro Lys Tyr Val Thr
            100                 105                 110

Arg Asp Asp Tyr Phe Lys Leu Phe Pro Gly Leu Leu Gln Glu Ile Pro
        115                 120                 125

Pro Thr Gly Ala Ile Thr Asp Leu Ala Val Val Ser Asp Ala Phe Val
        130                 135                 140

Pro Ile Ile Lys Phe Asp Phe Leu Gly Ile Ser Ile Asp Leu Ile Phe
145                 150                 155                 160

Ser Arg Ile Ala Ser Leu Lys Gln Leu Pro Lys Asp Lys Asp Trp Asn
                165                 170                 175

Leu Lys Asp Ser Asn Ile Leu Arg Gly Leu Asp Glu Ala Glu Leu Arg
            180                 185                 190

Ser Leu Asn Gly Thr Arg Val Thr Asp Glu Ile Ile Ser Leu Val Pro
        195                 200                 205

Glu Pro Ser Thr Phe Arg Leu Ala Leu Arg Ala Ile Lys Leu Trp Ala
        210                 215                 220

Gln Arg Arg Ala Val Tyr Ala Asn Ile Met Gly Phe Pro Gly Gly Val
225                 230                 235                 240
```

```
Ala Trp Ala Met Leu Val Ala Arg Val Cys Gln Leu Tyr Pro Lys Ala
            245                 250                 255

Thr Ser Ser Val Val Val Asn Lys Phe Phe His Ile Met Arg Arg Trp
            260                 265                 270

Pro Trp Pro Gln Pro Val Leu Leu Lys Ala Val Glu Ser Gly Pro Leu
            275                 280                 285

Gln Val Arg Val Trp Asn Pro Lys Leu Tyr Lys Gly Asp Gln Phe His
        290                 295                 300

Leu Met Pro Ile Ile Thr Pro Ala Tyr Pro Ser Met Cys Ala Thr Tyr
305                 310                 315                 320

Asn Ile Thr Lys Ser Ala Met Thr Val Ile Gln Arg Glu Leu Gln Arg
                325                 330                 335

Gly Cys Glu Ile Thr Asp Ser Val Met Met Ser Lys Gln Pro Trp Ser
            340                 345                 350

Asp Leu Phe Val Lys His Ala Phe Phe Thr Ser Asp Tyr Lys His Tyr
            355                 360                 365

Ile Ser Val Ile Thr Thr Ser Thr Thr Lys Glu Ala His Lys Ile Trp
    370                 375                 380

Ser Gly Tyr Val Glu Ser Lys Val Arg Val Leu Val Gln Gly Leu Glu
385                 390                 395                 400

Gln His Pro Ser Ile Ala Leu Ala His Ala Phe Asn Lys Gly Tyr Asp
                405                 410                 415

Arg Arg His Lys Cys Ser Ser Glu Gln Glu Ile Asn Gln Val Gln Glu
            420                 425                 430

Gly Ser Leu Asp Tyr Leu Leu Lys Ala Gly Asp Ser Ser Ala Gly Asp
        435                 440                 445

Pro Ala Glu Gly Asn Lys Ser Pro Arg Arg Pro Ala Asp Gly Glu His
        450                 455                 460

Pro Glu Ile Thr Pro Glu Ala Thr Glu Thr Ile Val Phe Thr Thr Thr
465                 470                 475                 480

His Tyr Ile Gly Leu Glu Leu Val Glu Gly Ala Lys Ser Leu Asp Leu
                485                 490                 495

Ser Tyr Gln Val Asp Ser Phe Lys Gln Leu Cys Gly Gln Trp Glu Lys
            500                 505                 510

Phe Asn Ser Asn Leu Asn Tyr Leu Ser Val Gln His Val Arg Asn Val
            515                 520                 525

Lys Leu Pro Asp Asp Val Phe Glu Pro Cys Glu Thr Arg Pro Gln Lys
        530                 535                 540

Lys Ser Ala Thr Asn Gly Ser Leu Gln Lys Lys Lys Arg Gly Ala Ser
545                 550                 555                 560

Glu Val Asp Met His Pro Pro Ala Lys Arg Gln Gln Ser Ser Val Thr
                565                 570                 575

Ala Ala Gly
```

<210> SEQ ID NO 27
<211> LENGTH: 606
<212> TYPE: PRT
<213> ORGANISM: Neohortaea acidophila

<400> SEQUENCE: 27

```
Met Asp Pro Lys Leu Gly Val Ser Gly Thr Met Ser Met Glu Pro Pro
1               5                   10                  15

Ser Pro Lys Asp Ile Lys Leu Asp Asp Ala Leu Leu Gln Glu Leu Lys
            20                  25                  30
```

-continued

```
Ser Arg Asn Glu Phe Glu Ala Pro Glu Glu Thr Gln Arg Arg His Ser
        35              40              45

Val Leu Asp Arg Leu Glu Ser Val Leu Lys Arg Leu Val Ala Met Val
    50              55              60

Gly Lys Gln Gln Gly Leu Pro Pro Gly Ile Leu Asn Glu Ala Gly Gly
65              70              75              80

Lys Ile Phe Thr Phe Gly Ser Phe Glu Leu Gly Val Tyr Gly Pro Lys
            85              90              95

Ser Asp Met Asp Thr Leu Met Ala Ala Pro Lys His Val Ser Arg Glu
            100             105             110

Asp Phe Phe Gln Tyr Met Pro Asp Leu Leu Arg Lys Glu Phe Lys Pro
            115             120             125

Glu Glu Ile Ala Glu Leu Thr Pro Val Pro Gly Ile Ser Val Pro Ile
    130             135             140

Ile Lys Leu Glu Leu Cys Gly Val Ser Val Asp Leu Ile Phe Cys Arg
145             150             155             160

Leu His Leu Gln Ser Val Pro Lys Ser Gln Glu Leu Ser Asn Leu Asp
            165             170             175

Leu Leu Arg Gly Leu Asp Asp Thr Asp Leu Lys Cys Val Asn Gly Thr
            180             185             190

Arg Val Thr Arg Arg Ile Leu Glu Leu Val Pro Gln Thr Lys Val Phe
            195             200             205

Arg Met Ala Leu Arg Ala Val Lys Leu Trp Ala Lys Gln Arg Ala Leu
    210             215             220

Tyr Gly Asn Ile Val Gly Tyr Pro Gly Gly Val Ala Tyr Ala Met Met
225             230             235             240

Val Ala Arg Ile Cys Gln Leu Tyr Pro Arg Ala Ala Ala Pro Leu Val
            245             250             255

Ile Trp Lys Phe Phe Tyr Leu Met Arg Lys Trp Asn Trp Pro Ser Pro
            260             265             270

Val Leu Leu Gln Asn His Glu Glu Gly Ser Ile Asn Leu Arg Glu Trp
            275             280             285

Asp Pro Ser Ile Tyr Pro Gly Asp Lys Arg His Leu Met Pro Ile Ile
    290             295             300

Thr Pro Ala Phe Pro Arg Met Asn Ala Cys His Thr Ile Gly Pro Ser
305             310             315             320

Thr Lys Lys Val Leu Leu Gln Glu Met Glu Arg Ala Glu Gly Ile Val
            325             330             335

Arg Ser Ile Tyr Glu Ser Gly Arg Pro Trp Arg Asp Leu Phe Gln Arg
            340             345             350

His Ser Phe Phe Thr Asp Ala Tyr Arg His Tyr Ile Cys Val Ile Thr
            355             360             365

Ala Gly Arg Thr Lys Glu Ala Gln Gln Ala Trp Ser Gly Leu Val Glu
    370             375             380

Ser Lys Val Lys Trp Leu Ile Val Gly Ile Glu His Ser Asp Ala Lys
385             390             395             400

Ser Val Glu Leu Val Gln Pro Tyr Asn Lys Gly Phe Asn Arg Val His
            405             410             415

Glu Cys Lys Gly Asp Ala Asp Ile Asp Lys Thr Leu Asp Gly Asn Leu
            420             425             430

Asp Cys Gln Val Lys Glu Ile Lys Thr Val Thr Thr Glu Gln Ala Gly
            435             440             445
```

-continued

```
Asp Val Gln Phe Gln Ala Ala Ala Gln Thr Asp Thr Asp Gly Gln Glu
    450             455             460

Val Pro Ala Pro Asn Gly Glu Ala Glu Val Pro Pro Gln Thr Asp Gly
465             470             475             480

Pro Gln Thr Ile Trp Thr Thr Thr Phe Tyr Leu Gly Ile Gly Leu Thr
                485             490             495

Lys Gly Ala Asn Ser Leu Asp Ile Ser Ser Pro Ile Arg Asp Phe Thr
                500             505             510

Gln Gln Cys Lys Glu Trp Gln Asn Tyr Asp Glu Asn Leu His Ser Ile
            515             520             525

Arg Val Lys His Met Arg Asn Tyr Asp Leu Pro Ala Asp Val Phe Ala
    530             535             540

Glu Gly Glu Thr Arg Pro Thr Arg Thr Lys Lys Lys Ser Ala Pro Lys
545             550             555             560

Thr Thr Asp Pro Thr Ala Met Asp Ala Ala Asn Lys Lys Arg Ser Phe
                565             570             575

Asn Asn Ser Gly Leu Asp Thr Leu Asp Asp Pro Ala Lys Arg Arg Ala
            580             585             590

Ser Ala Asn Gly Thr Ala Thr Pro Asn Gly Val Pro Pro Arg
            595             600             605

<210> SEQ ID NO 28
<211> LENGTH: 333
<212> TYPE: PRT
<213> ORGANISM: Trypanosoma brucei

<400> SEQUENCE: 28

Met Pro Pro Ser Pro Ala Val Val Gly Arg Ser Leu Val Asn Ser Phe
1               5               10              15

Lys Gln Phe Val Ser Lys Asp Leu His Thr Arg His Val Asp Ala Thr
                20              25              30

Tyr Arg Leu Val Leu Asp Cys Val Ala Ala Val Asp Pro Leu Met Arg
            35              40              45

Leu Tyr Thr Phe Gly Ser Thr Val Val Tyr Gly Val His Glu Lys Gly
    50              55              60

Ser Asp Val Asp Phe Val Val Leu Asn Lys Thr Asp Val Glu Asp Gly
65              70              75              80

Lys Gly Gly Asp Ala Ala Thr Gln Val Ala Lys Gly Leu Gln Ala Asp
                85              90              95

Ile Leu Ala Lys Leu Ala Arg Val Ile Arg Gln Lys His Leu Ser Trp
            100             105             110

Asn Val Glu Glu Val Arg Arg Thr Arg Val Pro Val Val Arg Val Lys
    115             120             125

Gly Gly Gly Ala Val Asp Phe Asp Ile Thr Ala Tyr Arg Arg Asn Gly
    130             135             140

Val Arg Asn Ser Ala Leu Leu Arg Ala Tyr Phe Glu Gln Asn Pro Pro
145             150             155             160

Cys Arg Trp Leu Ser Met Ser Ile Lys Arg Trp Ser Lys Gln Thr Gly
                165             170             175

Leu Asn Ala Ser Val Ile Gly Gly Ser Ile Thr Ser Tyr Gly Phe Asn
            180             185             190

Leu Met Val Val Tyr Tyr Leu Leu Gln Arg Asn His Leu Gln Phe Val
            195             200             205

Pro Pro Ser Thr Ile Asp Val Ser Arg Val Glu Pro Leu Pro Pro His
    210             215             220
```

-continued

Leu Pro Leu Glu Glu Pro Ala Asp Glu Gly Leu Glu Leu Gly Thr Gln
225                 230                 235                 240

Val Leu Asp Phe Leu His Phe Phe Leu His Glu Phe Asp Ser Asp Lys
                245                 250                 255

Gln Val Ile Ser Leu Asn Arg Pro Gly Ile Thr Thr Lys Glu Glu Leu
                260                 265                 270

Asp Trp Thr Lys Ser Ala Glu Asp Phe Ala Arg Met Asn Gly Glu Lys
            275                 280                 285

Val His Tyr Gln Trp Cys Ile Glu Asp Pro Tyr Glu Leu Asn Leu Asn
        290                 295                 300

Val Gly Arg Asn Val Thr Pro Leu Lys Arg Asp Phe Leu Arg Arg His
305                 310                 315                 320

Leu Glu Lys Ala Arg Asp Thr Ala Leu Leu Thr Ile Val
                325                 330

<210> SEQ ID NO 29
<211> LENGTH: 349
<212> TYPE: PRT
<213> ORGANISM: Schizosaccharomyces pombe

<400> SEQUENCE: 29

Gly Ser His Met Ser Tyr Gln Lys Val Pro Asn Ser His Lys Glu Phe
1               5                   10                  15

Thr Lys Phe Cys Tyr Glu Val Tyr Asn Glu Ile Lys Ile Ser Asp Lys
                20                  25                  30

Glu Phe Lys Glu Lys Arg Ala Ala Leu Asp Thr Leu Arg Leu Cys Leu
            35                  40                  45

Lys Arg Ile Ser Pro Asp Ala Glu Leu Val Ala Phe Gly Ser Leu Glu
        50                  55                  60

Ser Gly Leu Ala Leu Lys Asn Ser Asp Met Asp Leu Cys Val Leu Met
65                  70                  75                  80

Asp Ser Arg Val Gln Ser Asp Thr Ile Ala Leu Gln Phe Tyr Glu Glu
                85                  90                  95

Leu Ile Ala Glu Gly Phe Glu Gly Lys Phe Leu Gln Arg Ala Arg Ile
                100                 105                 110

Pro Ile Ile Lys Leu Thr Ser Asp Thr Lys Asn Gly Phe Gly Ala Ser
            115                 120                 125

Phe Gln Cys Asp Ile Gly Phe Asn Asn Arg Leu Ala Ile His Asn Thr
        130                 135                 140

Leu Leu Leu Ser Ser Tyr Thr Lys Leu Asp Ala Arg Leu Lys Pro Met
145                 150                 155                 160

Val Leu Leu Val Lys His Trp Ala Lys Arg Lys Gln Ile Asn Ser Pro
                165                 170                 175

Tyr Phe Gly Thr Leu Ser Ser Tyr Gly Tyr Val Leu Met Val Leu Tyr
            180                 185                 190

Tyr Leu Ile His Val Ile Lys Pro Pro Val Phe Pro Asn Leu Leu Leu
        195                 200                 205

Ser Pro Leu Lys Gln Glu Lys Ile Val Asp Gly Phe Asp Val Gly Phe
    210                 215                 220

Asp Asp Lys Leu Glu Asp Ile Pro Pro Ser Gln Asn Tyr Ser Ser Leu
225                 230                 235                 240

Gly Ser Leu Leu His Gly Phe Phe Arg Phe Tyr Ala Tyr Lys Phe Glu
            245                 250                 255

```
Pro Arg Glu Lys Val Val Thr Phe Arg Arg Pro Asp Gly Tyr Leu Thr
            260                 265             270

Lys Gln Glu Lys Gly Trp Thr Ser Ala Thr Glu His Thr Gly Ser Ala
            275             280             285

Asp Gln Ile Ile Lys Asp Arg Tyr Ile Leu Ala Ile Glu Asp Pro Phe
            290             295             300

Glu Ile Ser His Asn Val Gly Arg Thr Val Ser Ser Ser Gly Leu Tyr
305             310             315             320

Arg Ile Arg Gly Glu Phe Met Ala Ala Ser Arg Leu Leu Asn Ser Arg
            325             330             335

Ser Tyr Pro Ile Pro Tyr Asp Ser Leu Phe Glu Glu Ala
            340             345
```

```
<210> SEQ ID NO 30
<211> LENGTH: 480
<212> TYPE: PRT
<213> ORGANISM: Terfezia boudieri

<400> SEQUENCE: 30
```

```
Met Ser Gly Pro Pro Ser Gly Pro Pro Ser Gly Pro Arg Tyr Arg Gly
1               5               10              15

Gly His Arg Asn Phe Gly Pro Arg His Leu Gln Ser Gln Glu Arg Gln
            20              25              30

Gln Gln Gln Gln Gln Gln Gln Gln Gln Gln Gln Pro Tyr Gln Pro
            35              40              45

Ser Pro Gln Glu Leu Ala Val Leu Ala Glu Val Val Ile Glu Gln Ile
    50              55              60

Ala Leu Ala Thr Pro Ser Ala Glu Glu Leu Glu Arg Lys Thr Lys Leu
65              70              75              80

Arg Glu Arg Leu Arg Lys Leu Cys Thr Asn Val Ser Pro Thr Ala Glu
            85              90              95

Leu Glu Ala Phe Gly Ser Leu Val Ser Gly Phe Ala Thr Val Gly Ser
            100             105             110

Asp Leu Asp Leu Val Leu Val Asp Lys Gly Gly Ser Thr Asn Arg Pro
            115             120             125

Phe Phe Glu Val Pro Leu Leu Leu Glu Gln Glu Leu Lys Asp Asn Gly
            130             135             140

Leu Glu Ala Gln Leu Leu Ala Lys Thr Arg Val Pro Ile Leu Lys Ile
145             150             155             160

Lys Gln Pro Ala Thr Glu Glu Tyr Pro Lys Glu Val Ala Ala Asp Ile
            165             170             175

Gly Phe Ala Asn Pro Leu Ala Ile Arg Asn Thr Asp Met Leu Ser Met
            180             185             190

Tyr Ser Lys Cys Asp Pro Arg Val Ile Asp Met Val Arg Phe Ile Lys
            195             200             205

Arg Trp Ala Lys Arg Arg Lys Ile Asn Asn Pro Tyr Lys Gly Thr Leu
            210             215             220

Ser Ser Tyr Gly Tyr Val Leu Met Val Leu His Tyr Leu Ile Asn Ile
225             230             235             240

Val Glu Pro Pro Val Leu Pro Asn Leu Gln Leu Tyr Pro Ile Pro Ala
            245             250             255

Glu Thr Pro Lys Asp Glu Ile Thr Thr Glu Glu Gly His Asn Val Trp
            260             265             270
```

-continued

```
Tyr Tyr Lys Asp Val Ala Glu Ile Gln Arg Arg Val Ala Glu Gly Thr
    275                 280                 285

Met Thr Thr Asn Thr Met Asp Leu Pro Leu Leu Leu Leu Gly Phe Phe
    290                 295                 300

Glu Phe Tyr Ala Tyr Arg Phe Gly Trp Val Lys Asp Ile Ile Ser Ile
305                 310                 315                 320

Arg Thr Lys Gly Gly Leu Ile Ser Lys Val Asp Lys Gly Trp Thr Val
                325                 330                 335

Val Ala Val Arg Val Gly Lys Cys Glu Ala Glu Tyr Lys Asp Arg Tyr
                340                 345                 350

Leu Phe Ala Ile Glu Asp Pro Phe Glu Thr Asn His Asn Val Ser Arg
                355                 360                 365

Thr Cys Asn Ile Tyr Gly Val Arg Lys Ile Arg Asp Glu Phe Lys Arg
    370                 375                 380

Ala Asn Arg Ile Met Arg Met Arg Glu Gly Val Gly Ala Leu Arg Tyr
385                 390                 395                 400

Lys Leu Phe Glu Glu Ala Pro Glu Asp Val Arg Pro Gln His His Gln
                405                 410                 415

Lys Gln Ser Ile Ala Gly Glu Glu His Val Asn Gly Ala Pro Glu Ser
                420                 425                 430

Gly Arg Glu Asp Arg Glu Gly Asn Gln Leu Val Glu Glu Leu Glu Gly
                435                 440                 445

His Ser Asn Gly Asn Gly Ile His Pro Ser Glu Gly Tyr Pro Gly Pro
    450                 455                 460

Gly Leu Ala Ala Val Val Glu Gly Val Gln Arg Leu Ser Val Asp Ala
465                 470                 475                 480

<210> SEQ ID NO 31
<211> LENGTH: 761
<212> TYPE: PRT
<213> ORGANISM: Drechslerella stenobrocha

<400> SEQUENCE: 31

Met Glu Leu Thr Thr Gly Asp Phe Gly Gly Pro Pro Gly Ala Ser Asn
1               5                   10                  15

Ala Thr Gly Pro Gly Gln Lys Pro Glu Asp Pro Arg Thr Met Asp Pro
                20                  25                  30

Val Gly Glu Gln Thr Leu Glu Ser Arg Leu Arg Gly Met Leu Leu His
                35                  40                  45

Gly Gly Pro Pro Pro Val Asp Pro Arg Thr Gln Leu Arg His Pro Ser
    50                  55                  60

Gly Leu Ala Gln Gln Ala Gln Gln Ala Gln Gln Gln Pro Ile Gly Ile
65                  70                  75                  80

Asp Pro Ala Val Pro Gly His Leu His Gln Leu Gln Thr Ala Ala Ala
                85                  90                  95

Pro Pro Gln Gln Ser Arg Leu Pro Pro Ser Pro Asn Ile His His Gln
                100                 105                 110

His Leu Gln Pro Arg Leu Leu Gln Arg Ser Asn Thr Leu Pro Pro Pro
    115                 120                 125

Gly Gly Leu Thr Gln Pro Pro Pro Gly Leu Glu Arg Ala Gly Thr Phe
    130                 135                 140

His Gly Pro Val Pro Val Ala Gln Phe Gly Tyr His Gly Ser Tyr Pro
145                 150                 155                 160
```

-continued

```
Thr Ala His Ser Gln Arg Gly Arg Tyr Gly Asn Arg Arg Asn Gly Phe
                165                 170                 175

Gln Asn Ala Pro Val Pro Gln Met Asn Asn Asn Leu His Phe Pro Pro
                180                 185                 190

Leu Gly Thr Val Pro Ser Gln Pro Pro Pro Leu Ser Glu Arg Ser
                195                 200                 205

Ser Leu Ser Asn Met Asn Asn Pro Arg Arg His Ser Gly Pro Gly His
        210                 215                 220

Tyr His Thr Asp Asn Asn His Ser Pro Pro Tyr Lys Arg Tyr Glu Ala
225                 230                 235                 240

Phe His Gly Ala Pro Gly Ser Pro Gln Gly Tyr Ser Gly Ser Pro Pro
                245                 250                 255

Gln Asn Arg Gln Gly Arg Pro Tyr His Ser Ser Arg Gly Ser His Gly
                260                 265                 270

Gly Arg Asn Asn Arg Asn Phe Trp Pro Leu Asp Tyr Asp Gly Leu Thr
                275                 280                 285

Asn Tyr Ala Lys Tyr Ile Val Glu Ser Val Ser Pro Thr Pro Glu Glu
        290                 295                 300

Ile Ala Met Lys Asp Asn Met Leu Arg Arg Ile Ser Glu Ile Cys Asp
305                 310                 315                 320

Lys Leu Val Pro Gly Ser Arg Ile Ile Pro Phe Gly Ser Leu Val Ser
                325                 330                 335

Gly Phe Ala Thr Lys Gly Ala Asp Met Asp Val Ile Phe Ala His Asp
                340                 345                 350

Thr Ile Asp Pro Ala Pro Ser Ser His Glu Ser Asn Ile Pro Val Arg
                355                 360                 365

Leu Ala Asn Glu Phe Leu Lys Arg Gly Phe Glu Val Asp Leu Leu Ile
        370                 375                 380

Lys Thr Arg Val Pro Ile Leu Lys Leu Lys Thr Pro Gly Glu Pro Val
385                 390                 395                 400

Ser Arg Pro Gly Ser Pro Val Ser Glu Gly Asp Gly Asp Ser Ser Glu
                405                 410                 415

Glu Pro Trp Pro Glu Asn Val Ser Cys Asp Ile Gly Phe Lys Ala His
                420                 425                 430

Leu Gly Ile Thr Asn Ser His Phe Phe Arg Thr Tyr Ser His Cys Asp
                435                 440                 445

His Arg Phe Arg Glu Met Val Leu Phe Val Lys Gln Trp Ser Lys Asn
        450                 455                 460

Arg Asp Leu Asn Ser Pro Tyr Phe Gly Thr Leu Ser Ser Tyr Gly Tyr
465                 470                 475                 480

Val Leu Met Val Ala His Phe Leu Ile Asn Val Val Gln Pro Pro Val
                485                 490                 495

Leu Pro Asn Leu Gln Leu Ile Pro Pro Ala Ala Glu Thr Ala Glu Ser
                500                 505                 510

Glu Leu Met Gln Glu Gly Phe Asn Ile Trp Tyr Phe Lys Asp Leu Glu
                515                 520                 525

Arg Ile Ala Ser Gly Glu Phe Leu Pro Gly Gly Arg Asn Glu Met Ser
        530                 535                 540

Leu Gly Gln Leu Val His Glu Phe Phe Gln Tyr Tyr Thr Thr Asn Phe
545                 550                 555                 560

Asn Phe Val Ser Glu Cys Val Thr Ile Arg Thr Pro Gly Gly Val Met
                565                 570                 575
```

-continued

```
Tyr Lys Gln Glu Lys Gly Trp Thr Ser Ala Arg Glu Arg Val Gly Glu
            580                 585                 590

Met Asn Asn Thr Tyr Gln Asp Arg Tyr Leu Leu Ala Leu Glu Asp Pro
            595                 600                 605

Phe Glu Val Ser His Asn Val Gly Arg Thr Cys Gly Gly Ala Gly Val
        610                 615                 620

Arg Arg Ile Arg Ala Glu Met Gln Arg Ala Ala His Ile Ile Arg Lys
625                 630                 635                 640

Val Ser Ala Lys Glu Gly Gly Thr Pro Arg Ser Ala Gly Trp Glu Met
                645                 650                 655

Pro Leu Val Val Glu Asp Leu Met Thr Thr Val Arg Glu Thr Asn Arg
            660                 665                 670

Gly Phe Arg Asn Arg Arg Val Asn Gln Lys Asn Leu Met Glu Trp Ile
            675                 680                 685

Arg Asn Asp Trp Thr Val Gly Lys Cys Leu Val Gln Ile Asp Ala Ala
            690                 695                 700

Ala Glu Glu Leu Arg Lys Lys Arg Glu Leu Gly Leu Pro Asp Asp Ala
705                 710                 715                 720

Glu Leu Pro Pro Glu Ser Glu Glu Asp Ser Glu Gly Asp Glu Asp Ala
                725                 730                 735

Ser Glu Glu Glu Glu Glu Ser Ser Ser Asp Asp Gly Ala Val Arg Val
            740                 745                 750

Val Gly Gly Gly Ser Arg Gly Gly Val
            755                 760
```

```
<210> SEQ ID NO 32
<211> LENGTH: 337
<212> TYPE: PRT
<213> ORGANISM: Phytomonas sp.

<400> SEQUENCE: 32
```

```
Met Thr Ser Leu Ser Ala Val Asn Val Gly Lys Leu Val Cys Asp Ser
1               5                   10                  15

Phe Gly Lys Leu Leu Ser Lys Asn Leu Asp Ile Lys Pro Ile Val Gln
            20                  25                  30

Thr His Glu Ile Val Ser Gln Ser Met Gln Thr Val Asp Pro Ser Met
            35                  40                  45

Ala Leu Tyr Val Phe Gly Ser Thr Ala Val Tyr Gly Phe His Glu Ser
        50                  55                  60

Gly Cys Asp Val Asp Phe Val Ala Leu Asn Gln Lys Asp Val Ser Asp
65                  70                  75                  80

Gly Lys Ala Ala Asp Pro Ser Ser Glu Ile Ala Lys Gly Leu Gln Val
                85                  90                  95

Asp Phe Leu Ser Arg Leu Glu Ala Ser Leu Arg Glu Met His Asn Leu
            100                 105                 110

Ala Trp Lys Met Asp Leu Val Arg Arg Thr Arg Val Pro Val Leu Arg
            115                 120                 125

Val Lys Gly Asp Pro Cys Gly Ile Asp Phe Asp Val Thr Ala Arg Arg
        130                 135                 140

Arg Asn Gly Val Arg Asn Ser Ala Leu Leu Ser Ala Tyr Phe Lys Gln
145                 150                 155                 160

Lys Pro Glu Thr Arg Trp Leu Ser Met Ala Ile Lys Gln Trp Ser Lys
                165                 170                 175

Arg Ala Gly Phe Asn Met Ser Val Asp Gly Gly Cys Leu Thr Ser Tyr
            180                 185                 190
```

```
Gly Cys Asn Leu Met Val Val Tyr Tyr Leu Leu Gln Arg Gln Leu Val
        195                 200                 205

Lys Phe Val Asp Pro Glu Arg Cys Asp Val Ala His Ile Pro Ser Leu
    210                 215                 220

Pro Ser Tyr Leu Pro Leu Glu His Pro Ala Gln Asn Gly Ser Glu Leu
225                 230                 235                 240

Gly Asp Met Val Leu Asp Phe Leu Asn Tyr Tyr Leu His Glu Phe Asn
                245                 250                 255

Pro Glu Thr Glu Val Ile Ser Leu Ser Arg Ala Asp Lys Thr Thr Lys
                260                 265                 270

Glu Met Ile Tyr Trp Thr Lys Gln Ala Glu Asp Met Ala Arg Ile Ser
                275                 280                 285

Gly Glu Lys Val Ser Tyr Arg Trp Cys Ile Glu Asp Pro Phe Glu His
        290                 295                 300

Asn Leu Asn Val Gly Arg Tyr Val Thr Pro Phe Lys Leu Thr Leu Leu
305                 310                 315                 320

Arg Lys His Met Glu Arg Ala Lys Glu Thr Ala Leu Leu Leu Ser Ile
                325                 330                 335

Ser
```

```
<210> SEQ ID NO 33
<211> LENGTH: 355
<212> TYPE: PRT
<213> ORGANISM: Bodo saltans

<400> SEQUENCE: 33
```

```
Met Leu Ser Pro Ala Ala Ile Gly Lys Ala Ile Leu Asp His His Ala
1                   5                   10                  15

Ser Leu Ile Gly Ala Asp Leu Ser Val Lys Arg Val His Asp Ala His
                20                  25                  30

Ser Leu Val Lys Asn Ser Leu Asp Ser Val Ala Pro Asp Leu Lys Leu
            35                  40                  45

Tyr Thr Phe Gly Ser Ser Thr Val Phe Gly Phe His Glu Pro Lys Ser
    50                  55                  60

Asp Val Asp Phe Val Ala Leu Arg Gln Glu Asp Ile Val Asp Gly Lys
65                  70                  75                  80

Gly Gly Asp Ser Thr Ser Gln Leu Ala Lys Gly Leu Gln Thr Gln Val
                85                  90                  95

Leu Ala Lys Leu Ala Ala Ser Val Arg Gln Lys Asn Val Gln Trp Ala
            100                 105                 110

Val Glu Glu Val Arg Arg Ala Arg Val Pro Val Val Lys Val Lys Ala
        115                 120                 125

Pro His Ile Asp Phe Asp Ile Thr Ala His Arg Arg Asn Gly Val Arg
    130                 135                 140

Asn Ser Ala Leu Leu Arg His Tyr Leu Thr Gln Val Pro Glu Asn Arg
145                 150                 155                 160

Trp Leu Ser Ile Ala Ile Lys Ser Trp Ser Lys Arg Val Gly Met Asn
                165                 170                 175

Gly Pro Val Gly Gly Tyr Leu Thr Ser Tyr Gly Phe Asn Ile Leu Val
            180                 185                 190

Val Tyr Tyr Leu Leu His Arg Arg Arg His Glu Gln Pro Glu Val Glu
        195                 200                 205

Gln Lys Glu Gly Gln Asp Gly Ala Ala Ser Ala Ser Val Asp Gly Lys
    210                 215                 220
```

Gln Gln Lys Glu Leu Thr Phe Ile Asp Lys Asp Thr Leu Asp Val Ser
225                 230                 235                 240

Leu Ile Pro Pro Ile Pro Glu Tyr Leu Ala Leu Glu Pro Pro Asn Pro
                245                 250                 255

Glu Thr Leu Gly Glu Gln Val Leu Asp Phe Phe Asp Phe Tyr Leu Ser
            260                 265                 270

Arg Phe Pro Met Glu Ser His Val Ile Ser Leu Ser His Lys Glu Pro
            275                 280                 285

Ile Thr Lys Gln Ser Leu Asn Trp Thr Lys Thr Ala Glu Asp Met Lys
        290                 295                 300

Asn Asn Thr Ser Met Glu Lys Val Phe Tyr Arg Leu Cys Ile Glu Asp
305                 310                 315                 320

Pro Tyr Glu Val Asn Leu Asn Val Gly Arg Asn Val Ser Pro Phe Lys
                325                 330                 335

Phe Asp Leu Met Lys Lys His Phe Val Lys Gly Arg Ala Thr Ala Leu
            340                 345                 350

Gly Leu Leu
        355

<210> SEQ ID NO 34
<211> LENGTH: 425
<212> TYPE: PRT
<213> ORGANISM: Angomonas deanei

<400> SEQUENCE: 34

Met Pro Pro Asn Pro Arg Gln Leu Gly Ala Ala Met Ile Glu Gln Phe
1               5                   10                  15

Arg Pro Leu Leu Gln Ala Pro Gln Gln Ser Gln Leu Thr Val Leu Ser
            20                  25                  30

Glu Ala Pro Leu Phe Gln Arg Ile Gln Arg Glu Val His Glu Leu Asp
        35                  40                  45

Pro Gly Ala Arg Val Tyr Ile Phe Gly Ser Thr Arg Val Tyr Gly Phe
    50                  55                  60

His Asp Ser Gly Ala Tyr Gln Gln Gln Ser Ala Gln Val Pro Pro Ser
65              70                  75                  80

Asp Val Asp Met Ala Val Leu Arg Arg Glu Asp Leu Leu Asp Gly Ser
                85                  90                  95

Gly Val Asp Pro Ser Ser Glu Leu Thr Arg Asn Val Gln Ala Glu Phe
            100                 105                 110

Leu Glu Lys Leu Leu Asn Arg Leu Gln Gln Ser Glu Gly Ser Ala Ser
        115                 120                 125

Ile Arg Ser Asn Cys Ser Ser Leu Val Lys Arg Thr Arg Val Pro Val
    130                 135                 140

Leu Arg Val Lys His Leu Val Ser Asn His Ser Pro Pro His Asp Lys
145                 150                 155                 160

Glu Asp Asn Ile Ser Val Gln Val Pro Phe Asp Phe Asp Ile Thr Cys
                165                 170                 175

Gly Arg Arg Cys Gly Ile Arg Asn Ser Ala Leu Phe Phe His Tyr Val
            180                 185                 190

Gln Gln Met Pro Met Ile Arg Phe Leu Leu Leu Ser Val Lys Lys Trp
        195                 200                 205

Ser Lys Gln Thr Gly Leu Asn Ser Ala Ile Lys Ala Pro Tyr Ser Asn
    210                 215                 220

-continued

```
Asn Asn Asn Gln Asn His Asn Leu Thr Ser Val Met Gly Gly Ser Leu
225             230             235             240

Thr Ser Tyr Gly Phe His Val Leu Leu Leu Tyr Tyr Leu Leu Arg Arg
                245             250             255

Gly Val Val Gln Tyr Ile Pro Met Thr Val Ser Ser Ala Ala Gly Ser
                260             265             270

Thr Asp Arg Ile Pro Asn Pro Gln Leu Asp Val Asn Ala Ile Pro Pro
            275             280             285

Val Pro Thr Phe Leu Pro Leu Leu Asp Pro Ala Leu Glu Pro His Gly
            290             295             300

Pro Gln Gly Asp Pro Val Arg Tyr Leu Gly Glu Leu Ala Leu Asp Trp
305             310             315             320

Cys His Phe Tyr Leu His Glu Phe Asp Val Glu Lys Glu Val Val Ser
                325             330             335

Leu Ser Arg Phe Asp Asp Tyr Phe Ala Asp Ser Pro Pro Ser Gly Pro
                340             345             350

Phe Pro Val Ile Thr Lys Asp Val Leu Gly Trp Thr Lys Gln Arg Glu
                355             360             365

Asp Gln Gly Arg Leu Arg Gly Glu Lys Val His Tyr Thr Leu Cys Ile
            370             375             380

Glu Asp Pro Tyr Glu Val Asn Leu Asn Val Gly Arg Asn Val Thr Ser
385             390             395             400

Leu Lys Trp Met Leu Phe Arg Lys His Leu Glu Lys Ala Ile Gln Thr
                405             410             415

Gly Leu Leu Leu Cys Pro Pro Ser Lys
                420             425

<210> SEQ ID NO 35
<211> LENGTH: 432
<212> TYPE: PRT
<213> ORGANISM: Protomyces lactucae-debilis

<400> SEQUENCE: 35

Met Pro Ser Ser Ser Pro Leu Gly Ala Thr Leu Pro Asn Ser Ser Ser
1               5               10              15

Leu Ala Val Ser Ala Ala Ala Ala Val Val Pro Asp Pro Leu Phe Ala
                20              25              30

Phe Thr Gln Phe Ala Val Asp Ala Val Arg Asn Asn Thr Val Ser His
            35              40              45

Ala Glu Leu Val Glu Lys Glu Arg Leu Arg Gln Glu Leu Glu Ala Val
        50              55              60

Leu Gln Ala Leu Gln Pro Thr Ala Arg Leu Val Val Tyr Gly Ser Leu
65              70              75              80

Ala Asn Asn Leu Ala Ile Ala Asn Cys Asp Met Asp Leu Met Asp Ala
                85              90              95

Leu His Asp Val Ser Val Asp Leu Pro Ala Leu Tyr Thr Glu Ala Leu
                100             105             110

Asn Ser Gln Gly Tyr Ser Val Lys Leu Leu Ser Lys Thr Arg Thr Pro
            115             120             125

Ile Val Lys Val Ser Leu Glu His Met Ala Val Pro Tyr Cys Val Asp
        130             135             140

Ile Ser Phe Asp Asn Ala Leu Ala Leu His Asn Thr Lys Leu Ile Ala
145             150             155             160
```

-continued

```
Thr Tyr Ala Ala Cys Asp Ser Arg Val Pro Ile Leu Leu Met Phe Val
            165                 170                 175

Lys Leu Trp Thr Ala Val Arg Arg Ile Asn Asp Pro His Ser Gly Thr
            180                 185                 190

Leu Ser Ser Tyr Gly Tyr Ala Leu Leu Leu Ile Phe Tyr Leu Gln Asn
            195                 200                 205

Arg Cys Asn Ser Pro Pro Val Leu Pro Asn Leu Gln Leu Ile Ser Ala
    210                 215                 220

Met Gly Thr Arg Ser Ala Asp Glu Leu Glu Cys Ser Gly Tyr Asp Ile
225                 230                 235                 240

Trp Phe Phe Lys Asp Val Glu Lys Ile Gln Gln Ala Gln Val Val Lys
            245                 250                 255

Asn Thr Ser Ser Ile Gly Thr Leu Leu Glu Gly Phe Phe Ser Tyr Phe
            260                 265                 270

Ala Tyr Glu Phe Asp Phe Arg Asp Leu Cys Ile Ser Ile Arg Thr Pro
            275                 280                 285

Gly Gly Ile Val Thr Lys Thr Ala Lys Thr Trp Thr Gln Met Val Glu
    290                 295                 300

His Leu Asn Asp Arg Gly Asp Ala Lys Val Lys Asp Arg Tyr Ile Leu
305                 310                 315                 320

Ser Ile Glu Asp Pro Phe Glu Ile Val His Asn Val Gly Arg Ser Val
            325                 330                 335

Thr Arg Ala Gly Leu Tyr Glu Ile Arg Gly Glu Phe Met Ala Ala Thr
            340                 345                 350

Arg Tyr Val Arg Gly Asn Lys Leu Asp Glu Ile Leu Asn Pro His Arg
            355                 360                 365

Arg Glu Ile Val Ala Pro Thr Ser Ser Thr Ala Met His Ser Pro Gln
    370                 375                 380

Gln Gln His Gly Thr Gln Gln Val Ser Pro Gly Glu Gly Ser Ser Pro
385                 390                 395                 400

Thr Pro Pro Ala Val His Ala Glu Ala Arg Pro Ser Thr Gly Thr Ala
            405                 410                 415

Thr Ser Thr Lys Thr Ser Gln Gln Ala Glu Thr Val Val Lys Ala Glu
            420                 425                 430
```

```
<210> SEQ ID NO 36
<211> LENGTH: 437
<212> TYPE: PRT
<213> ORGANISM: Strigomonas culicis

<400> SEQUENCE: 36
```

```
Met Pro Pro Pro Thr Pro Met Gln Leu Gly Arg Ala Ile Leu Arg His
1               5                   10                  15

Tyr Ala Pro Ser Ile Val Val Pro Thr Ala Ala Thr Ser Gly Pro Ile
            20                  25                  30

Ser Ser Ala Ala Ala Ser Thr Ala Ser Leu Ala Ser Ile His Pro Leu
            35                  40                  45

Phe Glu Phe Ile Gln Gly Cys Ala Arg Arg Val Asp Pro Gln Thr His
    50                  55                  60

Leu Tyr Val Phe Gly Ser Thr Arg Val Tyr Gly Phe Ser Glu Val Ser
65                  70                  75                  80

Ala Pro Thr Ser Val Gly Pro Pro Ala Ala Leu Ala Arg Pro Val Lys
            85                  90                  95
```

-continued

```
Asn Asp Val Asp Ile Ala Ala Leu Ser Ala Ala Asp Val Ala Thr Thr
            100                 105                 110

Pro Ser Pro His Ser Ala Asp Ala Val Val Asp Lys Gly Ser Glu Leu
            115                 120                 125

Ala Lys Ser Leu Gln Ile Asp Phe Leu Glu Lys Leu Lys Met Gln Leu
            130                 135                 140

Gln Thr Gln Arg Gln His Gln Gly Asp Gly Ala Pro Pro Ala Ala Ser
145                 150                 155                 160

Leu Ser Trp Glu Met Glu Val Val Lys Arg Ala Arg Val Pro Val Leu
                165                 170                 175

Arg Leu Gln Pro Arg Pro Ala Tyr Thr Thr Ser Ala Ala Gly Gly Val
            180                 185                 190

Pro Thr Tyr Asn Val Asp Val Thr Tyr Gly Arg Arg Cys Gly Val Leu
            195                 200                 205

Asn Ser Ala Leu Leu Arg Arg Tyr Met Asp Gln Gln Pro Asp Leu Arg
            210                 215                 220

Tyr Leu Cys Leu Ala Val Lys Arg Trp Ser Lys Leu Thr Gly Leu Asn
225                 230                 235                 240

Thr Ala Thr Ser Pro Asp Gly Gly Leu Thr Ser Tyr Gly Phe His
                245                 250                 255

Leu Leu Leu Val Tyr Tyr Ala Leu Arg Arg Arg Leu Val Ala Tyr Val
            260                 265                 270

Ala Pro Glu Asn Ile Gln Trp Gly Asp Ile Ala Pro Val Pro Ala Ala
            275                 280                 285

Leu Pro Leu Arg Phe Pro Gly Asp Ala Asp Gly Ala Asp Ala Trp Arg
            290                 295                 300

Gly Arg Ser Leu Gly Glu Arg Ile Ala Gln Asp Asp Ala Ala Ala Ala
305                 310                 315                 320

Arg Val Gly Glu Trp Ala Leu Asp Phe Val Arg Phe Tyr Leu His Glu
                325                 330                 335

Phe Asp Tyr Glu Arg Asp Val Ala Ser Leu Ser Arg Gly Ala Ala Ala
            340                 345                 350

Ala Gly Leu Val Thr Thr Glu Ala Leu Gln Trp Thr Arg Gln Glu Glu
            355                 360                 365

Tyr Ala Ala Arg Gly Arg Gly Glu Tyr Leu Phe Tyr Arg Phe Cys Ile
            370                 375                 380

Glu Asp Pro Tyr Glu Ile Asn Leu Asn Val Gly Arg His Met Ser Ser
385                 390                 395                 400

Val Lys Leu Met Ile Phe Lys Lys His Leu Glu Lys Ala Leu Glu Thr
                405                 410                 415

Gly Leu Ala Phe Ile Pro Ala Asp Glu Lys Ala Lys Gln Arg Val Lys
            420                 425                 430

Pro Lys Gly Lys Glu
            435
```

<210> SEQ ID NO 37
<211> LENGTH: 467
<212> TYPE: PRT
<213> ORGANISM: Basidiobolus meristosporus

<400> SEQUENCE: 37

```
Met Ser Leu Glu Thr Asp Arg Ile Val Ser Glu Phe Lys Asp Leu Ala
1               5                   10                  15
```

-continued

```
Ile Ser Gln Thr Ser Glu Thr Asn Gln Pro Val Pro Asp Val Lys Val
        20              25              30

Ser Ser Val Glu Asp Ser Gln His His Ser Lys Ala His Pro Pro Lys
        35              40              45

Asn Glu Asn Gly Asn Asn Gln Gly His Arg His Gly Lys Lys Pro Phe
        50              55              60

His Arg Gly Ser Thr Phe Gly Glu Gln Gly Lys Ser Asp Arg Ser Tyr
65              70              75              80

Gly Ala Arg Ser Phe His Pro Asn Arg Gly Thr Gly Gln Tyr Glu Gly
                85              90              95

Lys Arg Val Leu Asp Lys Ser Asp Pro Arg Tyr Leu Lys Ala Arg Ala
            100             105             110

Arg Phe Ile Ser Val Leu Thr Glu Gln Val Ser Glu Leu Tyr Leu Lys
            115             120             125

Leu Thr Pro Ser Val Glu Glu Val Ser Arg Arg Glu Gln Leu Tyr Phe
        130             135             140

Arg Ile His Ser Ile Cys Glu Glu Leu Phe Pro Asp Ala Gln Leu Phe
145             150             155             160

Gln Phe Gly Ser Thr Ala Asn Gly Phe Gly Leu Lys Asn Ala Asp Val
                165             170             175

Asp Phe Cys Leu Cys Thr Ala Glu Asn Ser Ser Leu Thr Ala Val Ala
            180             185             190

Phe Val Glu Gln Leu Gly Ser Val Leu Lys Glu Arg Gly Met Glu Asn
            195             200             205

Val Met Leu Leu Thr Arg Thr Arg Ile Pro Ile Ile Lys Leu Lys Asp
        210             215             220

Pro Val Ser Glu Leu Asn Cys Asp Ile Gly Phe Asn Asn Arg Leu Ala
225             230             235             240

Val Tyr Asn Thr Arg Leu Leu Arg Met Tyr Ala Glu Val Asp Ser Arg
                245             250             255

Val Lys Glu Ile Val Ala Ile Val Lys His Trp Ala Lys Ser Arg Gln
            260             265             270

Ile Asn Glu Pro Tyr Leu Gly Thr Leu Ser Ser Tyr Ala Tyr Val Leu
            275             280             285

Met Ile Ile Phe Val Leu Gln Gln Arg Gly Val Leu Pro Cys Leu Gln
        290             295             300

Gln Ile Cys Glu Gly Glu Lys Lys Glu Val Leu Val Asp Asn Tyr Asp
305             310             315             320

Ala Tyr Phe Phe Asp Asn Ile Thr Asp Leu Pro Lys Tyr Trp Lys Ser
                325             330             335

Gln Asn Asn Glu Ser Leu Gly Glu Leu Leu Tyr Glu Phe Phe Arg Phe
            340             345             350

Tyr Ala Ser Asp Phe Ser Tyr Tyr Gly Ser Val Val Ser Val Arg Thr
            355             360             365

Gly Gln Val Met Ser Lys Glu Glu Lys Gly Trp Thr Ala Glu Ala Thr
        370             375             380

Arg Glu Ser Gly Ala Ser His Val Gln Asp Arg Tyr Trp Val Cys Ile
385             390             395             400

Glu Asp Pro Phe Glu Val Thr His Asn Leu Gly Arg Pro Val Asn Lys
                405             410             415

Asn Ser Leu Tyr Thr Ile Arg Gly Glu Phe Met Arg Ala Ala Asn Ile
            420             425             430
```

-continued

```
Leu Gly Gly Thr Arg Thr Ser Thr Ile Leu Glu Arg Leu Cys Gln Val
        435                 440                 445

Tyr Val Pro Glu Glu Glu Pro Pro Arg Ala Pro Pro Ala Pro His Glu
        450                 455                 460

Arg Ser Asn
465

<210> SEQ ID NO 38
<211> LENGTH: 354
<212> TYPE: PRT
<213> ORGANISM: Neocallimastix californiae

<400> SEQUENCE: 38

Met Lys Thr Thr Glu Arg Thr Cys Thr Phe Glu Phe Tyr Asp Glu Leu
1               5                   10                  15

Thr Glu Glu Ile Asn Lys Ile Val Asn Lys Ile Lys Ala Lys Pro Asn
                20                  25                  30

Asp Leu Lys Lys Arg Glu Asn Leu Phe Asn Tyr Ile Lys Leu Val Ala
        35                  40                  45

Lys Lys Ile Phe Pro Asn Ser Lys Ala Tyr Lys Tyr Gly Ser Ile Glu
    50                  55                  60

Asn Gly Phe Ser Leu Thr Asn Gly Asp Ile Asp Ile Cys Ile Leu Asn
65                  70                  75                  80

Asn Lys Glu Phe Asn Asn Thr Pro Ala Glu Cys Val Glu Ile Leu Gly
                85                  90                  95

Glu Lys Leu Lys Glu Asp Gly Ile Asn Asp Ile Lys Leu Leu Ile Arg
            100                 105                 110

Ala Arg Val Pro Ile Ile Lys Met Lys Asp Asn Lys Ser Gly Ile Ser
        115                 120                 125

Cys Asp Ile Gly Phe Gln Asn Lys Leu Ala Ile Gln Asn Thr Lys Leu
        130                 135                 140

Ile Asn Ala Tyr Ser Lys Ile Asp Asp Arg Phe Lys Gln Met Val Phe
145                 150                 155                 160

Ile Ile Lys Tyr Trp Ser Lys Met Lys Asn Ile Asn Glu Pro Tyr Met
                165                 170                 175

Gly Thr Leu Ser Ser Tyr Cys Phe Ile Leu Met Ile Ile His Phe Leu
            180                 185                 190

Gln Ile Lys Glu Pro Pro Val Leu Pro Asn Leu Gln Lys Ile Tyr Leu
        195                 200                 205

Asp Asn Phe Ile Glu Tyr Glu Tyr Ile Asp Asp Phe Asn Val Ser Phe
        210                 215                 220

Phe Glu Asn Ile Asp Glu Leu His Lys Tyr Trp Asn Ser Lys Asn Asn
225                 230                 235                 240

Glu Ser Leu Gly Glu Leu Leu Val Glu Phe Phe Lys Tyr Tyr Ala Asn
                245                 250                 255

Asp Phe Pro Tyr Ile Thr Gly Val Ala Ser Ile Arg Val Gly Asn Ile
            260                 265                 270

Ile Thr Lys Glu Glu Lys Lys Trp Thr Arg Glu His Gln Phe Glu Ile
        275                 280                 285

Asn Lys Ser Asn Ser Val Lys Asp Arg Tyr Trp Phe Cys Val Glu Asp
        290                 295                 300

Pro Phe Glu Ile Thr His Asn Leu Gly Arg Pro Val Asp Arg Lys Ser
305                 310                 315                 320

Leu Phe Arg Ile Arg Gly Glu Phe Leu Lys Ala Val Lys Ile Ile Asn
                325                 330                 335
```

-continued

Asn Lys Asn Leu Thr Ala Leu Gln Val Leu Glu Lys Leu Leu Glu Lys
              340                     345                     350

Asn Ile

<210> SEQ ID NO 39
<211> LENGTH: 344
<212> TYPE: PRT
<213> ORGANISM: Perkinsela sp.

<400> SEQUENCE: 39

Met Leu Asp Pro Ser Glu Thr Cys Met Gly Arg Ile Lys Asn Ile His
1                   5                   10                  15

Ala Ile Ile Thr Ser Lys Leu Met Gly Leu Leu Val Glu Lys Asn Ala
              20                  25                  30

Gln Ile Tyr Cys Phe Gly Ser Ser Met Val Asn Gly Val Val Glu Lys
              35                  40                  45

Lys Ser Asp Val Asp Val Val Tyr Leu Thr Arg Glu Asp Leu Gln Lys
              50                  55                  60

Pro Leu Ser Ile Gly Asp Val Cys Asn Pro Gln Ser Arg Ser Glu Gln
65                  70                  75                  80

Thr Ser Ile Leu Ser Ala Ile Ser Lys Ile Leu Met Lys Asp Ser Glu
              85                  90                  95

Leu Phe Ser Thr Val Gln Glu Lys Pro Arg Ala Arg Val Pro Tyr Val
              100                 105                 110

Arg Gly Val Leu Lys Asn Gly Leu Glu Ile Asp Ile Ser Ala His Arg
              115                 120                 125

Arg Asn Gly Val Arg Asn Ser Leu Leu Leu Arg Ser Tyr Phe Ser Gln
              130                 135                 140

Ile Pro Pro Thr Arg Pro Ser Leu Pro Asn Ala Thr Thr Ser Val Tyr
145                 150                 155                 160

Arg Met Leu Ser Leu Ala Leu Lys Phe Trp Gly Lys Arg Thr Gly Leu
              165                 170                 175

Val Asp Pro Val Gln Thr Phe Leu Thr Ser Tyr Ala Phe Asn Val Leu
              180                 185                 190

Ile Cys Tyr Tyr Leu Gln Gln Arg Gly Gly Met Asp Phe Ile His Pro
              195                 200                 205

Glu Ser Ile Leu Ile Pro Lys Gly His Pro Thr Val Pro Asp Tyr Arg
              210                 215                 220

Glu Ile Ala Leu Ala Gly Thr Gln Gly His Thr Cys Leu Gly Trp Tyr
225                 230                 235                 240

Met Arg Asp Phe Leu Lys Phe Tyr Asn His Glu Phe Asp Tyr Asn Asn
              245                 250                 255

Thr Val Val Ser Leu Ser Arg Lys Gly Ile Thr Thr Lys Glu Tyr Leu
              260                 265                 270

Gly Trp Gly Leu Arg Asp Glu Glu Arg Met His Gly Thr Asp Gly Asn
              275                 280                 285

Ala Phe Phe Tyr Arg Phe Cys Val Glu Asp Pro Tyr Glu Asn Arg Leu
              290                 295                 300

Asn Leu Gly Arg Phe Val Thr Pro Leu Arg Tyr Ser Met Phe Arg Met
305                 310                 315                 320

Ala Leu His Gln Ala Gln Leu Asn Gly Phe Gly Tyr Leu Asn Leu Lys
              325                 330                 335

Asn Tyr Gly Ala Lys Ile Val Asp
              340

```
<210> SEQ ID NO 40
<211> LENGTH: 352
<212> TYPE: PRT
<213> ORGANISM: Saitoella complicata

<400> SEQUENCE: 40

Met Met Ala His Pro Ser Gln Gly Gly Ala His Pro Leu Ser Ala Gly
1               5                   10                  15

Pro Thr Asn Pro Gln Pro Tyr Gln Asp Ala Tyr Ser Gly Phe Thr Glu
            20                  25                  30

Tyr Val Leu Ser Ile Asn Arg Pro Gln Tyr Pro Ser Ala Asn Glu Met
        35                  40                  45

Tyr Leu Lys Glu Gln Leu Arg Ser Leu Ile Asp Val Glu Ile Val Gln
    50                  55                  60

Arg Ile Gln Pro Ser Ala Arg Val Ile Pro Phe Gly Ser Leu Val Asn
65                  70                  75                  80

Gly Phe Ala Thr Ala Asn Ser Asp Leu Asp Leu Cys Ile Leu Asp Asp
                85                  90                  95

Ser Pro Asn Pro Arg Tyr Lys Ile Lys Thr Glu Leu Pro Glu Val Leu
            100                 105                 110

Ala Ala Glu Phe Glu Arg Tyr Gly Phe Glu Val Lys Leu Leu Thr Lys
        115                 120                 125

Thr Arg Ile Pro Ile Ile Lys Leu Val Gln Gly Pro Thr Ala Gln Phe
    130                 135                 140

Pro Leu Gly Leu Ala Met Asp Ile Gly Phe Glu Asn Arg Leu Ala Leu
145                 150                 155                 160

His Asn Thr Arg Leu Leu Ala Thr Tyr Ser Arg Ile Asp Ser Arg Leu
                165                 170                 175

Arg Glu Met Val Leu Phe Val Lys His Trp Ala Lys Val Arg Gly Ile
            180                 185                 190

Asn Ser Ser Tyr His Gly Thr Leu Ser Ser Tyr Gly Tyr Val Leu Thr
        195                 200                 205

Ile Leu His Phe Leu Ile Asn Val Ala Ser Pro Ser Cys Leu Pro Asn
    210                 215                 220

Leu Gln His Ile Gly Ala Gln Val Pro Val Pro Phe Glu Glu Leu Glu
225                 230                 235                 240

Cys Glu Gly Tyr Asn Ile Trp Phe Phe Lys Asp Leu Thr Asn Ile Pro
                245                 250                 255

Pro Ser Leu Asn Arg Arg Ser Ile Gly Glu Leu Met Ala Glu Tyr Phe
            260                 265                 270

Ser Tyr Tyr Ala Gln Phe Asp Phe Arg Asn Met Val Ile Ser Ile Arg
        275                 280                 285

Thr Pro Gly Gly Leu Leu Thr Lys Thr Ser Lys Gly Trp Thr Gln Ala
    290                 295                 300

Leu Asp Arg Val Gly Pro Glu Asp Gln Lys Val Arg Ser Arg Asn Phe
305                 310                 315                 320

Leu Cys Ile Glu Asp Pro Phe Glu Ile Thr His Asn Val Gly Arg Thr
                325                 330                 335

Val Gly Lys Asn Gly Leu Tyr Asp Val Trp Pro Phe Val Ser Phe Ala
            340                 345                 350

<210> SEQ ID NO 41
<211> LENGTH: 388
<212> TYPE: PRT
```

<213> ORGANISM: Steccherinum ochraceum

<400> SEQUENCE: 41

```
Met Ala Thr Val Phe Ala Gln Ser His Ser Leu Leu Asn Thr Arg Gln
1                   5                   10                  15

Pro His Gln His Val Gln Gln Pro Ala Gln Gln Pro Pro Gln Gln Gln
                20                  25                  30

Gln Gln Gln Gln Ser Thr Arg Pro Lys Gln Leu Ser Lys Pro Arg Phe
            35                  40                  45

Tyr Ala Glu Phe Ser Gln Cys Leu Phe Asp Phe Val Ile Gln Leu Leu
        50                  55                  60

Pro Thr Pro Glu Glu Leu Ala Ile Lys Glu Asp Val Arg Lys Leu Leu
65                  70                  75                  80

Glu Arg Leu Ile Arg Thr Leu Glu Pro Asp Ser Arg Leu Leu Ser Phe
                85                  90                  95

Gly Ser Thr Ala Asn Gly Phe Ser Leu Arg Asn Ser Asp Met Asp Leu
                100                 105                 110

Cys Cys Leu Ile Asp Ser Asp Asp Arg Leu Ala Ala Ser Asp Leu Val
            115                 120                 125

Thr Met Leu Gly Asp Leu Leu Glu Arg Glu Thr Lys Phe His Val Lys
        130                 135                 140

Pro Leu Pro Tyr Ala Arg Ile Pro Ile Val Lys Leu Ser Leu Asp Pro
145                 150                 155                 160

Ser Pro Gly Leu Pro Phe Gly Ile Ala Cys Asp Ile Gly Phe Glu Asn
                165                 170                 175

Arg Leu Ala Leu Glu Asn Thr Arg Leu Leu Met Cys Tyr Ala Met Ile
                180                 185                 190

Asp Pro Ala Arg Val Arg Thr Met Val Leu Phe Leu Lys Val Trp Cys
            195                 200                 205

Lys Arg Arg Lys Ile Asn Ser Pro Tyr Lys Gly Thr Leu Ser Ser Tyr
        210                 215                 220

Gly Tyr Val Leu Leu Val Ile Phe Phe Leu Val His Val Lys Asn Pro
225                 230                 235                 240

Pro Val Leu Pro Asn Leu Gln Ser Met Pro Pro Leu Arg Pro Met Asp
                245                 250                 255

Lys Glu Glu Ser Thr Leu Asn Gly His Asn Val Trp Phe Phe Asp Asp
                260                 265                 270

Ile Asn Leu Leu Arg Gln Arg Trp Gln Ser Thr Asn Thr Glu Ser Val
        275                 280                 285

Ala Glu Leu Leu Val Asp Phe Phe Lys Phe Tyr Ser Arg Glu Phe Pro
        290                 295                 300

Tyr Asn Ser Gly Val Val Ser Ile Arg Ala Gly Gly Ile Lys Lys Asp
305                 310                 315                 320

Ser Lys Gly Trp Phe Ser Glu Ala Glu Arg Gly Ser Ala Arg Glu Arg
                325                 330                 335

Asn Arg Leu Cys Ile Glu Asp Pro Phe Glu Thr Asp Phe Asn Val Ala
                340                 345                 350

Arg Cys Val Thr Arg Asp Gly Leu Tyr Thr Ile Arg Gly Glu Leu Met
            355                 360                 365

Arg Ala Ser Arg Ile Leu Ala Ala Arg Pro Glu Arg Pro Ile Val Ala
        370                 375                 380

Leu Ala Gln Leu
385
```

-continued

<210> SEQ ID NO 42
<211> LENGTH: 421
<212> TYPE: PRT
<213> ORGANISM: Gymnopus androsaceus

<400> SEQUENCE: 42

Met Ala Ala Tyr Ser Pro Thr Met Ser Ser Asn Gln His Tyr His Glu
1               5                   10                  15

Leu Asn Ser Ala Ser Pro Pro Ala Arg Arg Lys Trp Leu Ala Asp Phe
            20                  25                  30

Ser Glu Cys Leu Phe Ser Phe Val Ile Gln Leu Leu Pro Thr Gln Glu
        35                  40                  45

Glu Leu Ala Val Lys Glu Asp Val Arg Lys Leu Leu Glu Arg Leu Ile
    50                  55                  60

Arg Thr Ile Glu Pro Glu Ser Arg Leu Leu Ser Phe Gly Ser Thr Ala
65                  70                  75                  80

Asn Gly Tyr Gly Leu Arg Asn Ser Asp Met Asp Leu Cys Cys Leu Ile
                85                  90                  95

Asp Ser Glu Glu Arg Leu Ala Ala Ser Asp Leu Val Thr Met Leu Gly
            100                 105                 110

Asp Leu Leu Glu Arg Glu Thr Lys Phe His Val Lys Pro Leu Pro His
        115                 120                 125

Ala Arg Ile Pro Ile Val Lys Leu Ser Leu Asp Pro Ser Pro Gly Leu
    130                 135                 140

Pro Leu Gly Ile Ala Cys Asp Ile Gly Phe Glu Asn Arg Leu Ala Leu
145                 150                 155                 160

Glu Asn Thr Arg Leu Leu Met Cys Tyr Ala Met Ile Asp Pro Thr Arg
                165                 170                 175

Val Arg Thr Met Val Leu Phe Leu Lys Val Trp Ser Lys Arg Arg Lys
            180                 185                 190

Ile Asn Ser Pro Tyr Lys Gly Thr Leu Ser Ser Tyr Gly Tyr Val Leu
        195                 200                 205

Leu Val Ile Tyr Phe Leu Val His Val Lys Asn Pro Pro Val Leu Pro
    210                 215                 220

Asn Leu Gln Gln Met Pro Pro Leu Arg Pro Ile Pro Lys Glu Glu Thr
225                 230                 235                 240

Tyr Leu Gly Gly Phe Asn Thr Trp Phe Phe Asp Asp Ile Glu Leu Leu
                245                 250                 255

Arg Gln Arg Trp His Ser Glu Asn Thr Glu Thr Val Ala Glu Leu Leu
            260                 265                 270

Ile Asp Phe Phe Arg Tyr Phe Ser Arg Asp Phe Pro Tyr Gly Val Gly
        275                 280                 285

Val Ala Ser Ile Arg Ala Gly Leu Leu Lys Lys Asp Ser Lys Gly Trp
    290                 295                 300

Gln Asn Asp Leu Ser Ala Ser Arg Tyr Asn Asp Ala Arg Glu Arg Asn
305                 310                 315                 320

Arg Phe Cys Ile Glu Asp Pro Phe Glu Thr Asp Tyr Asn Val Ala Arg
                325                 330                 335

Cys Val Thr Lys Asp Gly Leu Tyr Thr Ile Arg Gly Glu Phe Met Arg
            340                 345                 350

Ala Ser Arg Val Leu Ala Ala Arg Pro Glu Arg Ala Ile Leu Ala Leu
        355                 360                 365

Ala Asp Leu Cys Asp Glu Arg Lys Asp Glu Asp Pro Cys Arg Arg Ala
    370                 375                 380

-continued

```
Ser Leu Tyr Ser Phe Ser Ser Ser Ala Pro Thr Asn Thr Val Phe Gly
385                 390                 395                 400

Gly Lys Ser Ile Asn Ala Phe Gln Arg Asn Thr Asp Tyr Ser Leu Ser
                405                 410                 415

Phe Asp Gln Thr Pro
            420

<210> SEQ ID NO 43
<211> LENGTH: 512
<212> TYPE: PRT
<213> ORGANISM: Trypanosoma equiperdum

<400> SEQUENCE: 43

Met Gly Val Arg Leu Tyr Ser Cys Asp Ala Cys Pro His Ala Val Phe
1               5                   10                  15

Thr Thr His Ala Ala Leu Leu Ala His Ala Glu Glu His His Ala Asp
                20                  25                  30

Leu Leu Pro Asp His Ala Arg Leu Arg Ile Ala Gln Lys Leu Asn
            35                  40                  45

Pro Val Trp Asn Arg Ala Leu Asn Ala Arg Arg Asn Thr Ile Thr Ser
        50                  55                  60

Trp Gly Lys Lys Ile Phe His Val Ala Ala Gln Arg Asp Ala Gly Glu
65                  70                  75                  80

Ser Lys Met Gln Glu Ala His Arg Ala Arg Ala Gln Leu Glu Cys Val
                85                  90                  95

Val Arg Arg Trp His Asp Lys Ala Arg Val Phe Ile Phe Gly Ser Ser
                100                 105                 110

Val Ala Met Gly Val Trp Asp Gly Thr Ala Asp Ile Asp Phe Ala Val
                115                 120                 125

Val Asp Val Asp Ala Met Glu Arg Gly Ser Trp Pro Pro Leu Glu Lys
            130                 135                 140

Asn Ala Val Arg Ser Ile Thr Glu Leu Leu Arg Arg Val Gly Phe Ser
145                 150                 155                 160

Phe Val Asn Leu Glu Pro Ile Ser His Ala Arg Val Pro Ile Ile Lys
                165                 170                 175

His His Ala Ser Ser Pro Ile Leu Thr Val Ala Arg Arg Asp Ala Glu
            180                 185                 190

Asp Val Val Ala Arg Ser Ile Arg Phe Ile Leu Asn Gly Pro Ala Thr
            195                 200                 205

Arg Glu Asp Arg Leu Leu Leu Glu Gly Ser Val Arg Asp Ala Val Gly
        210                 215                 220

Pro Thr Gly Val Gln Gln Val Trp Trp Asn Arg Thr Ser Asp Met Met
225                 230                 235                 240

Ser Ala Thr Leu Glu Ser Thr Thr Ala Ala Val Arg Ala Ala Met Cys
                245                 250                 255

Ser Pro Ala Leu Ala Ser Ala Ser Leu Arg Thr Lys Val Gln Pro Ala
            260                 265                 270

His Asp Glu Cys Arg Pro Glu Leu Tyr Asn Ile Asp Phe Ala Leu Ser
            275                 280                 285

Phe Arg Ala Phe Gly Ile Arg Asn Ser Thr Leu Leu Arg Lys Tyr Leu
        290                 295                 300

Leu Ser His Pro Cys Ala Arg Pro Gly Ala Ile Val Leu Lys Asp Trp
305                 310                 315                 320
```

```
Ser Lys Thr Ser Gly Val Asn Asn Ser Val Asn Gly Tyr Phe Thr Ser
            325                 330                 335

Tyr Ala Ile Asn Ile Met Trp Ile Tyr Tyr Leu Val Gln Lys Gly Tyr
            340                 345                 350

Val Pro Tyr Val Asp Pro Leu Glu Ile Pro Glu Ser Leu Val Asn Tyr
            355                 360                 365

Thr Asp Phe Asp Pro Arg Tyr Thr Pro Met Ile Asp Pro Glu Ile Thr
    370                 375                 380

Asn Thr Glu Arg Glu Glu Leu Tyr Lys Ala Ala Gly Asp Met Leu Val
385                 390                 395                 400

Gly Phe Phe Tyr Phe Tyr Ser Phe Glu Phe Asp Trp Gly His Asn Val
            405                 410                 415

Ile Ser Leu Asn Arg Pro Gly Ile Thr Thr Lys Arg Met Leu Gly Trp
            420                 425                 430

His Val Glu Asp Val Val Pro Val Ala Ser Thr Ser Val Ser Ser Gly
            435                 440                 445

Gly Gly Gly Ser Asn Val Lys Arg His Pro Thr Arg Tyr Glu Leu Cys
    450                 455                 460

Ile Glu Asp Pro Tyr Glu Glu Asn Leu Asn Leu Gly Arg His Ile Gly
465                 470                 475                 480

Val Thr Lys Ser Leu Arg Val Arg Thr Glu Leu Tyr Arg Gly Leu Leu
            485                 490                 495

Ser Leu Leu Lys Glu Gly Glu Thr Arg Ser Cys Val Phe Ala Ala Ala
            500                 505                 510

<210> SEQ ID NO 44
<211> LENGTH: 531
<212> TYPE: PRT
<213> ORGANISM: Morchella conica

<400> SEQUENCE: 44

Met Thr Ala Gly Arg Asp Ile Arg Ser Pro Pro Arg Gly Gln Arg Gly
1               5                   10                  15

Gln Gly Phe Asn Lys Ser Gln Asn Ser Pro Arg Ala Leu Pro Leu Asn
            20                  25                  30

Ala Leu Asp His Phe Pro Pro Leu Gly Thr Gln Pro Thr Lys Ala Lys
            35                  40                  45

Thr Pro Pro Pro Asn Tyr Ser Gln Gln Gln Ser Thr Thr Ala Lys
    50                  55                  60

Pro Gln Gln Arg Thr Gln Tyr Gln Pro Leu Pro Ile Asp Thr Arg Asn
65                  70                  75                  80

Thr Asn Pro His His Ala Arg Gly Glu Val His Gly Arg Arg Asn Phe
            85                  90                  95

Arg Gly Asp Tyr Asn Gln Arg Gln Leu Arg Arg Asp Ile Gly Pro Glu
            100                 105                 110

Val Cys Gln Tyr Leu Ser Glu Leu Ser Lys Lys Val Ile Ala Glu Ala
            115                 120                 125

Ala Pro Pro Glu Ser Glu Ile Leu Val Lys Arg Ala Leu Leu Glu Arg
    130                 135                 140

Leu Glu Ala Ile Ser Lys Thr Ile Val Pro Asp Ala Lys Leu Ile Ala
145                 150                 155                 160

Phe Gly Ser Leu Val Thr Gly Phe Ala Thr Ala Asn Ser Asp Leu Asp
            165                 170                 175
```

-continued

```
Val Ile Phe Thr Gly Gly Asp Arg Val Asp Ile Leu Asn Glu Ser Ser
            180             185             190

Asp Asp Pro Ser Ser Asn Phe Arg Ile Pro Met Leu Leu Glu Ser Lys
            195             200             205

Leu Gln Glu Glu Gly Phe Gly Thr Thr Leu Leu Thr Lys Thr Arg Val
    210             215             220

Pro Ile Leu Lys Leu Val Gln Lys Ala Thr Glu Gln Ser Pro Tyr Glu
225             230             235             240

Leu Gln Cys Asp Ile Gly Phe Ser Asn His Leu Ala Leu Tyr Asn Thr
            245             250             255

Gln Met Leu Leu Thr Tyr Ser Lys Cys Asp Pro Arg Val Lys Glu Met
            260             265             270

Met Ile Phe Ile Lys Trp Trp Ala Lys Arg Arg His Ile Asn Asn Pro
            275             280             285

Tyr Arg Gly Thr Leu Ser Ser Tyr Gly Tyr Ala Leu Ile Val Leu His
    290             295             300

Tyr Leu Ile Asn Val Val Lys Pro Pro Val Leu Pro Asn Leu Gln Thr
305             310             315             320

Phe Pro Val Pro Asp Ser Ala Pro Thr Asn Glu Ile Ile Phe Glu Gly
            325             330             335

Asp Ser Asp Asp Thr Phe Glu Ile Trp Phe Tyr Lys Asp Ile Glu Lys
            340             345             350

Leu Pro Lys Ser Asp Asn Ala Met Asp Ile Gly Glu Leu Leu Lys Gly
            355             360             365

Phe Phe Glu Tyr Tyr Ala His Asn Phe Gln Trp Gly Arg Glu Val Val
    370             375             380

Ser Ile Arg Thr Lys Gly Gly Leu Met Thr Lys Gln Glu Lys Gly Trp
385             390             395             400

Val Ala Ala Val Ile Lys Pro Gly Arg Thr Glu Asn Ser Glu Val Lys
            405             410             415

Asn Arg Tyr Leu Phe Ala Val Glu Asp Pro Phe Glu Thr Glu His Asn
            420             425             430

Val Ser Arg Thr Cys Asn Gly Pro Gly Val Asn Arg Ile Lys Asp Glu
            435             440             445

Phe Lys Arg Ala Val Trp Leu Ile Arg Val Arg Asp Gly Gly Lys Thr
    450             455             460

Leu Phe Gln Asn Leu Cys Met Glu Ala Pro Pro Glu Arg Val Trp Val
465             470             475             480

Arg Arg Glu Asp Arg Asp Arg Arg Gly Ile Glu Glu Ala Gly Gly His
            485             490             495

Gly Ser Lys Asp His Gln Gly Ala Glu Gly Glu Ala Gly Asp Gly Val
            500             505             510

Lys His Glu Ser Val Val Leu Ser Glu Asp Gly Arg Asn Ala Leu Glu
            515             520             525

Ser Leu Val
    530
```

<210> SEQ ID NO 45
<211> LENGTH: 474
<212> TYPE: PRT
<213> ORGANISM: Pneumocystis murina -continued

<400> SEQUENCE: 45

```
Met Asp Ser Val Lys Gly Phe Glu Gly Val Glu Ser Val Val Phe Gln
1               5                   10                  15

Lys Glu Met Lys Lys Leu Thr Lys Ile Ser Asp Phe Ser Gly Lys Asn
            20                  25                  30

Tyr Gly Ser Gly Asn Glu Ile Glu Asp Leu Lys Lys Ser Leu Glu Lys
        35                  40                  45

Met Met Leu Glu Ser Val Asn Ile Gln Glu Lys Gly Val Phe Leu Arg
    50                  55                  60

Glu Lys Gly Ser Glu Gly Ser Tyr Glu Ala Asn Leu Asn Asp Lys Asp
65                  70                  75                  80

Val Leu Lys Asn Asn Lys Lys Asp Ser Asn Phe Arg Asn Ile Lys Tyr
                85                  90                  95

Tyr Glu Pro Lys Asp Tyr Gly Leu Tyr Val Asn Gly Lys Ala Val Trp
            100                 105                 110

Arg Lys Asn Tyr Asp Glu Tyr Phe Val Leu Ser Thr Phe Ile Ser His
            115                 120                 125

Thr Leu Lys His Ile Met Pro Thr Asn Glu Glu Ile Ser Gln Lys Glu
    130                 135                 140

Arg Phe Arg Phe Phe Leu Ser Glu Ile Leu Asn Thr Cys Arg Pro Ser
145                 150                 155                 160

Ala Lys Leu Val Leu Phe Gly Ser Val Ala Ser Gly Leu Ala Ile Val
            165                 170                 175

Asn Ser Asp Met Asp Phe Cys Val Met Asp Asp Ser Leu Asp Leu His
            180                 185                 190

Thr Asp Glu Phe Leu Lys Ile Phe Ser Glu Glu Ile Lys Lys Tyr Gly
        195                 200                 205

Met Glu Thr Thr Leu Leu Phe Arg Thr Arg Val Ser Ile Ile Lys Val
    210                 215                 220

Asn Ser Lys Gly Ser Phe Asn Phe Pro Gln Gly Ile Ser Cys Asp Ile
225                 230                 235                 240

Gly Phe Asn Asn Lys Leu Ala Ile Tyr Asn Thr Lys Leu Leu Ala Thr
            245                 250                 255

Tyr Ser Lys Cys Asp His Arg Val Arg Lys Ile Ile Leu Phe Val Lys
            260                 265                 270

Tyr Trp Ala Lys Arg Arg Lys Ile Asn Asp Pro Tyr His Gly Thr Leu
            275                 280                 285

Ser Ser Tyr Gly Tyr Val Leu Leu Ile Leu His Tyr Leu Ile Asn Ile
    290                 295                 300

Val Pro Ile Pro Leu Leu Pro Asn Leu Gln Gln Met Lys Val Ala Ser
305                 310                 315                 320

Trp Arg Ser Ile Pro Gln Ser Glu Ile Glu Cys Asp Gly Tyr Asn Val
            325                 330                 335

Trp Phe Tyr Lys Asp Ile Asp Ile Ser Cys Ser Phe Ser Asn Asn Thr
            340                 345                 350

Asp Ser Leu Gly Lys Leu Val Tyr Gly Phe Phe Tyr Tyr Tyr Ala Tyr
        355                 360                 365

Gln Phe Asn Trp Lys Asp His Val Val Ser Ile Arg Thr Gln Thr Gly
    370                 375                 380

Leu Leu Thr Lys Gln Glu Lys Gly Trp Thr Gln Ala Met Glu Arg Val
385                 390                 395                 400
```

-continued

```
Phe Val Ser Asp Lys Ile Phe Lys Asp Arg Tyr Ile Leu Ala Ile Glu
            405             410             415

Asp Pro Phe Glu Ile Thr His Asn Val Gly Arg Thr Val Asn Lys Gln
            420             425             430

Ser Ser His Ile Ile Arg Gly Glu Phe Phe Arg Ala Ser Lys Leu Ser
            435             440             445

Ser Ser Lys Leu Arg Lys Lys Ile Phe Asn Glu Leu Cys Glu Glu Arg
            450             455             460

Ile Ile Ile Asn Asn Phe Ser Asn Val Ile
465             470

<210> SEQ ID NO 46
<211> LENGTH: 445
<212> TYPE: PRT
<213> ORGANISM: Schizosaccharomyces japonicus

<400> SEQUENCE: 46

Met Ser Gly Asn Gly Asn Gly His Phe Ile Pro Gly Val His Thr Val
1               5               10              15

Glu Glu Ile Glu Arg Gln Phe Val Asn Leu Ala Leu Gln Lys Arg Asn
            20              25              30

Gln Ala Ala Ala Ala Ala Ala Ala Ala Glu Arg Glu Leu Asp Pro
            35              40              45

Val Thr Cys Phe Leu Leu Ser Thr Tyr Asp Asp Val Arg Val Ser Asp
            50              55              60

Asp Glu Leu Arg Glu Lys Asp Ala Ile Met Asn Leu Leu Lys His Val
65              70              75              80

Val His Ser Val Arg Pro Glu Ala Asp Ile Val Ala Phe Gly Ser Ile
                85              90              95

Gln Ser Gly Leu Ala Leu Lys Asn Ser Asp Ile Asp Ala Cys Ile Leu
            100             105             110

Leu Pro Asp Ile Gly Glu Glu Met Glu Glu Phe Ala Ser Glu Cys Phe
            115             120             125

Glu Arg Phe Thr Ala Leu Gly Phe Glu Gly Lys Tyr Leu Arg Lys Ala
            130             135             140

Arg Ile Pro Ile Ile Lys Leu Leu Ser Asp Thr Lys Asn Arg Tyr Tyr
145             150             155             160

Tyr Gly Phe Gln Cys Asp Ile Gly Phe Asn Asn Gln Leu Ala Ile Tyr
                165             170             175

Asn Thr Ser Leu Leu His Gln Tyr Ser Leu Ile Asp Pro Arg Cys Lys
            180             185             190

Gln Leu Ala Ile Leu Val Lys Tyr Trp Ala Lys Gln Lys Arg Ile Asn
            195             200             205

Ser Pro Tyr Tyr Gly Thr Leu Ser Ser Tyr Gly Tyr Val Leu Met Val
            210             215             220

Leu Phe Tyr Leu Ile His Val Val Arg Pro Ala Val Leu Pro Asn Leu
225             230             235             240

Gln Asp Ser Pro His Lys Gln Asp Leu Tyr Val Glu Gly Phe Asn Val
            245             250             255

Gly Phe Val Arg Gly Thr Thr Val Ala Arg Arg Asn Thr Glu Ser Leu
            260             265             270

Pro Gln Leu Leu Ala Gly Phe Tyr Gly Phe Phe Ala His Glu Phe Asn
            275             280             285
```

```
Tyr Arg Glu Ser Val Ile Ser Ile Arg Gln Pro Gly Gly Leu Leu Lys
    290                 295                 300

Lys Val Asp Lys Asp Trp Thr Leu Ala Lys Glu His Thr Gly Ser Ala
305                 310                 315                 320

Asp Gln Val Ile Lys Asp Arg Tyr Val Leu Ala Ile Glu Asp Pro Phe
                325                 330                 335

Glu Ile Thr His Asn Val Gly Arg Thr Val Ser Lys Ala Gly Leu Phe
                340                 345                 350

Glu Ile Arg Gly Glu Phe Met Gln Ala Thr Arg Leu Leu Asn Ala Ala
            355                 360                 365

Thr Leu His Ser Thr Ser Ala Ile Arg Lys Leu Arg Ala Ser Leu Phe
    370                 375                 380

Lys Glu Arg Leu Glu Pro Lys Ser His Leu Lys Tyr Gln Lys Ala Leu
385                 390                 395                 400

Arg Gln Lys Arg Met Gly Thr Glu Gly Lys Ala Ala Ala Glu Gly Lys
                405                 410                 415

Thr Asn Asn Pro Thr Ala Ala Ser Gly Ser Asp Ser Ala Pro Ser Glu
                420                 425                 430

Ser Ala Ser Arg Thr Ala Thr Val Glu Ser Arg Glu Pro
        435                 440                 445

<210> SEQ ID NO 47
<211> LENGTH: 620
<212> TYPE: PRT
<213> ORGANISM: Acanthosis nigricans

<400> SEQUENCE: 47

Met Asn Pro Pro Gln Gln Thr Thr Gly Leu Glu Asp His Leu Arg Ser
1               5                   10                  15

Leu Ile Ile Asn Asn Gln Thr Pro Pro Asn His Ser Ile Ser Pro Ala
                20                  25                  30

Ala Lys Ile Pro His Lys His His Pro Arg Thr Ser Thr Asp Ser Arg
            35                  40                  45

Gly Phe Val Arg Ser Gln Thr Ile His Arg Pro Gly Pro Ala Ala Ser
    50                  55                  60

Gln Pro Pro Ser Asn Gly Pro Asn Arg Arg Phe Pro Gly Glu Ala Gln
65                  70                  75                  80

Arg Pro Asp His Arg Pro Pro His Leu Arg Gly Pro Ser Gln Asn Arg
                85                  90                  95

Asn Tyr Trp His Gly Ala Pro Pro Pro Arg Gln Val Val Pro Gln
            100                 105                 110

Gly Leu Ser Pro Pro Ala Ala Thr Asn Leu His His Phe Pro Pro Leu
        115                 120                 125

Gly Ala Lys Val Ala Pro Pro Pro Ser Leu Pro Ser Tyr His Ser
    130                 135                 140

Val Pro Thr Ala Pro Cys His Arg Pro Glu Asn Gln Arg Pro Val Tyr
145                 150                 155                 160

Gln Asn Asp Asn Arg Asp Ser Tyr His Tyr Lys Gln Arg Gly Leu Tyr
                165                 170                 175

Asp Gly Tyr Leu Ala Glu Gln Trp Arg Glu Leu Asp Lys Met Ala Lys
            180                 185                 190

Glu Val Leu Leu Thr Ala Thr Pro Val Asp Gly Glu Lys Glu Ala Lys
        195                 200                 205
```

-continued

```
Glu Lys Phe Met Gln Asp Leu Glu Ala Val Cys Gln Lys Val Glu Pro
    210             215             220

Thr Ala Lys Leu Ile Pro Phe Gly Ser Ile Val Thr Gly Phe Ala Thr
225             230             235             240

Arg Gly Ser Asp Ile Asp Cys Val Phe Thr Ser Asn Thr Asp Ser Ala
                245             250             255

Leu Gln Asn Asp Lys Ile Thr Glu Pro Glu Thr Pro Phe Asp Arg His
                260             265             270

Asp Glu Leu Val Thr Gln Leu Gln Glu Ser Gly Tyr Asn Ala Gln Leu
    275             280             285

Leu Thr Arg Thr Arg Val Pro Ile Ile Lys Leu Val Arg Pro Ala Thr
    290             295             300

Pro Asp Val Pro Asp Ser Val Ser Cys Asp Ile Gly Phe Asn Asn Phe
305             310             315             320

Leu Ala Ile His Asn Thr Arg Leu Leu Arg Thr Tyr Ala Ala Cys Asp
                325             330             335

Glu Arg Leu Val Gln Met Val Leu Phe Ile Lys Trp Trp Ala Lys Arg
                340             345             350

Arg His Ile Asn Ser Pro Tyr Arg Gly Thr Leu Ser Ser Tyr Gly Tyr
                355             360             365

Ala Leu Leu Ile Val His Tyr Leu Ile Asn Ile Ala Gln Pro Pro Val
    370             375             380

Leu Pro Asn Leu Gln Leu Phe His Pro Pro Ala Thr Gln Thr Ser Thr
385             390             395             400

Glu Leu Gln Tyr Glu His Asn Gly Asn Val Cys Asn Ile Trp Tyr Leu
                405             410             415

Lys Asp Thr Ser Thr Leu Pro Arg Ser Ala Asn Lys Ala Ser Ile Gly
                420             425             430

Glu Leu Leu Arg Gly Phe Phe Glu Tyr Tyr Ala Phe Thr Phe Arg Trp
    435             440             445

Gln Asn Asp Val Val Ser Ile Arg Thr Ala Gly Gly Ile Leu Thr Lys
    450             455             460

Met Glu Lys Asn Trp Cys Ala Ala Arg Ser Arg Pro Gly Gly Arg Glu
465             470             475             480

Glu Gly Gln Val Trp Glu Val Lys Asp Arg Val Asp Val Gln His Arg
                485             490             495

Tyr Leu Leu Ala Ile Glu Asp Pro Phe Glu Thr Thr His Asn Val Ala
                500             505             510

Arg Thr Cys Thr Phe Asn Gly Val Gly Arg Ile Lys Ser Glu Leu Lys
    515             520             525

Arg Ala Met Tyr Leu Ile Lys Ser Arg Asp Pro Gly His His Arg Leu
    530             535             540

Arg Thr Glu Leu Phe Glu Glu Ala Pro Pro Glu Arg Pro Phe Val Arg
545             550             555             560

Asn Gly Lys Glu Val Val Asp Lys Leu Glu Lys Val Glu Ile Val Glu
                565             570             575

Glu Arg Ala Gly Val Ala Val Glu Ile Val Glu Glu Arg Ala Gly Val
                580             585             590

Ala Val Glu Ile Val Glu Glu Arg Ala Gly Val Ala Leu Glu Val Val
    595             600             605

Glu Glu Arg Ala Gly Ala Ala Val Glu Val Asp Val
    610             615             620
```